(12) United States Patent
Popejoy et al.

(10) Patent No.: US 11,911,016 B2
(45) Date of Patent: Feb. 27, 2024

(54) LATERAL ACCESS RETRACTOR AND CORE INSERTION

(71) Applicant: Stryker European Operations Holdings LLC, Kalamazoo, MI (US)

(72) Inventors: Spencer Popejoy, Ringwood, NJ (US); Charles L. Bush, Jr., Wayne, NJ (US); Steven F. Krause, Oakland, NJ (US)

(73) Assignee: STRYKER EUROPEAN OPERATIONS HOLDINGS LLC, Kalamazoo, MI (US)

( * ) Notice: Subject to any disclaimer, the term of this patent is extended or adjusted under 35 U.S.C. 154(b) by 180 days.

(21) Appl. No.: 17/512,930

(22) Filed: Oct. 28, 2021

(65) Prior Publication Data

US 2022/0047256 A1 Feb. 17, 2022

Related U.S. Application Data

(63) Continuation of application No. 16/369,139, filed on Mar. 29, 2019, now Pat. No. 11,191,532.
(Continued)

(51) Int. Cl.
*A61B 1/32* (2006.01)
*A61B 17/02* (2006.01)
*A61B 17/00* (2006.01)

(52) U.S. Cl.
CPC ............ *A61B 17/0206* (2013.01); *A61B 1/32* (2013.01); *A61B 17/0293* (2013.01); *A61B 2017/0046* (2013.01); *A61B 2017/00477* (2013.01)

(58) Field of Classification Search
CPC ... A61B 17/02; A61B 17/0206; A61B 17/025; A61B 17/0293; A61B 1/32
(Continued)

(56) References Cited

U.S. PATENT DOCUMENTS

| 380,745 A | 4/1888 | Chamberlin |
| 447,761 A | 3/1891 | Clough |

(Continued)

FOREIGN PATENT DOCUMENTS

| FR | 2807313 A1 | 10/2001 |
| WO | 9609013 A1 | 3/1996 |

(Continued)

OTHER PUBLICATIONS

Krause et al., U.S. Appl. No. 62/546,780, filed Aug. 17, 2017, titled "Lateral Access Alignment Guide and Rigid Arm".
(Continued)

*Primary Examiner* — Eduardo C Robert
*Assistant Examiner* — Christina Negrellirodriguez
(74) *Attorney, Agent, or Firm* — Duane Morris LLP

(57) ABSTRACT

In one embodiment, the present disclosure relates to a retractor apparatus that includes a retractor frame, five arms attached to the retractor frame and five rods each attached to one of the five arms. Each rod includes a convex surface facing a center of the retractor frame. At least two of the five rods are movable independently from one another. A first rod of the five rods includes a longitudinal axis and is translatable along the longitudinal axis. Further, the first rod is attached to a first arm of the five arms and is pivotable relative to the first arm. The axis of pivot is offset from the longitudinal axis through which the first rod translates.

19 Claims, 40 Drawing Sheets

Related U.S. Application Data

(60) Provisional application No. 62/650,671, filed on Mar. 30, 2018.

(58) Field of Classification Search
USPC .................................. 600/201, 214, 235
See application file for complete search history.

(56) References Cited

U.S. PATENT DOCUMENTS

| | | |
|---|---|---|
| 832,201 A | 10/1906 | Fistler |
| 1,157,202 A | 10/1915 | Bates et al. |
| 1,428,653 A | 9/1922 | Nick |
| 1,618,261 A | 2/1927 | Arbogast |
| 1,827,497 A | 10/1931 | Varney |
| 1,839,726 A | 1/1932 | Amold |
| 1,863,057 A | 6/1932 | Innes |
| 1,944,009 A | 1/1934 | Homer |
| 2,313,164 A | 3/1943 | Nelson |
| 2,586,488 A | 2/1952 | Smith |
| 2,812,758 A | 11/1957 | Blumenschein |
| 2,854,983 A | 10/1958 | Baskin |
| 3,070,088 A | 12/1962 | Brahos |
| 3,087,486 A | 4/1963 | Kilpatrick |
| 3,221,743 A | 12/1965 | Thompson et al. |
| 3,394,700 A | 7/1968 | Yamamoto |
| 3,397,699 A | 8/1968 | Kohl |
| 3,417,746 A | 12/1968 | Moore et al. |
| 3,509,883 A | 5/1970 | Dibelius |
| 3,522,799 A | 8/1970 | Gauthier |
| 3,731,673 A | 5/1973 | Halloran |
| 3,749,088 A | 7/1973 | Kohlmann |
| 3,770,342 A | 11/1973 | Dudragne |
| 3,782,370 A | 1/1974 | McDonald |
| 3,788,318 A | 1/1974 | Kim et al. |
| 3,789,852 A | 2/1974 | Kim et al. |
| 3,796,214 A | 3/1974 | Davis |
| 3,807,393 A | 4/1974 | McDonald |
| 3,944,341 A | 3/1976 | Pomerantzeff |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,141,364 A | 2/1979 | Schultze |
| 4,226,228 A | 10/1980 | Shin et al. |
| 4,254,763 A | 3/1981 | McCready et al. |
| 4,312,353 A | 1/1982 | Shahbabian |
| 4,337,763 A | 7/1982 | Petrassevich |
| 4,545,374 A | 10/1985 | Jacobson |
| 4,589,868 A | 5/1986 | Dretler |
| 4,616,635 A | 10/1986 | Caspar et al. |
| 4,617,916 A | 10/1986 | LeVahn et al. |
| 4,716,901 A | 1/1988 | Jackson et al. |
| 4,718,151 A | 1/1988 | LeVahn et al. |
| 4,739,762 A | 4/1988 | Palmaz |
| 4,779,611 A | 10/1988 | Grooters et al. |
| 4,813,401 A | 3/1989 | Grieshaber |
| 4,817,587 A | 4/1989 | Janese |
| 4,896,669 A | 1/1990 | Bhate et al. |
| 4,949,707 A | 8/1990 | LeVahn et al. |
| 4,971,037 A | 11/1990 | Pelta |
| 4,971,038 A | 11/1990 | Farley |
| 5,032,113 A | 7/1991 | Burns |
| 5,052,373 A | 10/1991 | Michelson |
| 5,092,314 A | 3/1992 | Zeitels |
| 5,116,318 A | 5/1992 | Hillstead |
| 5,139,511 A | 8/1992 | Gill et al. |
| 5,183,464 A | 2/1993 | Dubrul et al. |
| 5,312,417 A | 5/1994 | Wilk |
| 5,320,611 A | 6/1994 | Bonutti et al. |
| 5,351,679 A | 10/1994 | Mayzels et al. |
| 5,377,667 A | 1/1995 | Patton et al. |
| 5,383,889 A | 1/1995 | Warner et al. |
| 5,391,156 A | 2/1995 | Hildwein et al. |
| 5,391,178 A | 2/1995 | Yapor |
| 5,425,730 A | 6/1995 | Luloh |
| 5,431,676 A | 7/1995 | Dubrul et al. |
| 5,452,732 A | 9/1995 | Bircoll |
| 5,460,170 A | 10/1995 | Hammerslag |
| 5,474,057 A | 12/1995 | Makower et al. |
| 5,496,345 A | 3/1996 | Kieturakis et al. |
| 5,505,690 A | 4/1996 | Patton et al. |
| 5,512,038 A | 4/1996 | O'Neal et al. |
| 5,514,153 A | 5/1996 | Bonutti |
| 5,520,611 A | 5/1996 | Rao et al. |
| 5,522,790 A | 6/1996 | Moll et al. |
| 5,580,344 A | 12/1996 | Hasson |
| 5,607,441 A | 3/1997 | Sierocuk et al. |
| 5,653,726 A | 8/1997 | Kieturakis |
| 5,678,572 A | 10/1997 | Shaw et al. |
| 5,685,826 A | 11/1997 | Bonutti |
| 5,688,223 A | 11/1997 | Rosendahl |
| 5,702,417 A | 12/1997 | Hermann |
| 5,707,362 A | 1/1998 | Yoon |
| 5,728,046 A | 3/1998 | Mayer et al. |
| 5,755,661 A | 5/1998 | Schwartzman |
| 5,772,661 A | 6/1998 | Michelson |
| 5,772,681 A | 6/1998 | Leoni |
| 5,782,854 A | 7/1998 | Hermann |
| 5,827,318 A | 10/1998 | Bonutti |
| 5,827,319 A | 10/1998 | Carlson et al. |
| 5,830,191 A | 11/1998 | Hildwein et al. |
| 5,860,997 A | 1/1999 | Bonutti |
| 5,865,802 A | 2/1999 | Yoon et al. |
| 5,888,196 A | 3/1999 | Bonutti |
| 5,888,197 A | 3/1999 | Mulac et al. |
| 5,893,866 A | 4/1999 | Hermann et al. |
| 5,897,087 A | 4/1999 | Farley |
| 5,916,151 A | 6/1999 | Charters |
| 5,919,128 A | 7/1999 | Fitch |
| 5,928,139 A * | 7/1999 | Koros ............... A61B 17/0206 600/245 |
| 5,941,777 A | 8/1999 | Moser et al. |
| 5,944,658 A | 8/1999 | Koros et al. |
| 5,944,734 A | 8/1999 | Hermann et al. |
| 5,954,739 A | 9/1999 | Bonutti |
| 5,957,832 A | 9/1999 | Taylor et al. |
| 5,961,499 A | 10/1999 | Bonutti et al. |
| 5,967,970 A | 10/1999 | Cowan et al. |
| 5,993,472 A | 11/1999 | Hermann et al. |
| 6,004,337 A | 12/1999 | Kieturakis et al. |
| 6,004,340 A | 12/1999 | Hermann et al. |
| 6,022,340 A | 2/2000 | Sepetka et al. |
| 6,027,518 A | 2/2000 | Gaber |
| 6,032,671 A | 3/2000 | Mollenauer et al. |
| 6,036,689 A | 3/2000 | Tu et al. |
| 6,074,343 A | 6/2000 | Nathanson et al. |
| 6,079,761 A | 6/2000 | Sadeck |
| 6,080,174 A | 6/2000 | Dubrul et al. |
| 6,083,154 A | 7/2000 | Liu et al. |
| 6,093,173 A | 7/2000 | Balceta et al. |
| 6,102,928 A | 8/2000 | Bonutti |
| 6,139,493 A | 10/2000 | Koros et al. |
| 6,171,299 B1 | 1/2001 | Bonutti |
| 6,187,023 B1 | 2/2001 | Bonutti |
| 6,206,826 B1 | 3/2001 | Mathews et al. |
| 6,206,886 B1 | 3/2001 | Bennett |
| 6,234,961 B1 | 5/2001 | Gray |
| 6,235,043 B1 | 5/2001 | Reiley et al. |
| 6,258,089 B1 | 7/2001 | Campbell et al. |
| 6,267,424 B1 | 7/2001 | Gillette |
| 6,277,136 B1 | 8/2001 | Bonutti |
| 6,312,443 B1 | 11/2001 | Stone |
| 6,322,500 B1 | 11/2001 | Sikora et al. |
| 6,325,812 B1 | 12/2001 | Dubrul et al. |
| 6,338,730 B1 | 1/2002 | Bonutti et al. |
| 6,354,995 B1 | 3/2002 | Hoftman et al. |
| 6,387,095 B1 | 5/2002 | Kennett et al. |
| 6,431,025 B1 | 8/2002 | Koros et al. |
| 6,436,119 B1 | 8/2002 | Erb et al. |
| 6,464,634 B1 | 10/2002 | Fraser |
| 6,464,697 B1 | 10/2002 | Edwards et al. |
| 6,466,817 B1 | 10/2002 | Kaula et al. |
| 6,468,205 B1 | 10/2002 | Mollenauer et al. |
| 6,494,893 B2 | 12/2002 | Dubrul et al. |

(56) References Cited

U.S. PATENT DOCUMENTS

| | | | |
|---|---|---|---|
| 6,511,423 B2 | 1/2003 | Farley |
| 6,564,078 B1 | 5/2003 | Marino et al. |
| 6,569,182 B1 | 5/2003 | Balceta et al. |
| 6,592,602 B1 | 7/2003 | Peartree et al. |
| 6,602,190 B2 | 8/2003 | Dobrovolny |
| 6,616,605 B2 | 9/2003 | Wright et al. |
| 6,632,234 B2 | 10/2003 | Kieturakis et al. |
| 6,632,235 B2 | 10/2003 | Weikel et al. |
| 6,689,152 B2 | 2/2004 | Balceta et al. |
| 6,692,462 B2 | 2/2004 | Mackenzie et al. |
| 6,760,616 B2 | 7/2004 | Hoey et al. |
| 6,814,715 B2 | 11/2004 | Bonutti et al. |
| 6,846,287 B2 | 1/2005 | Bonadio et al. |
| 6,849,064 B2 | 2/2005 | Hamada |
| 6,866,676 B2 | 3/2005 | Kieturakis et al. |
| 6,869,398 B2 | 3/2005 | Obenchain et al. |
| 6,921,364 B2 | 7/2005 | Mollenauer et al. |
| 6,945,933 B2 | 9/2005 | Branch et al. |
| 6,948,751 B2 | 9/2005 | Wooten et al. |
| 7,050,848 B2 | 5/2006 | Hoey et al. |
| 7,056,321 B2 | 6/2006 | Pagliuca et al. |
| 7,079,883 B2 | 7/2006 | Marino et al. |
| 7,144,368 B2 | 12/2006 | Larson et al. |
| 7,150,714 B2 | 12/2006 | Myles |
| 7,177,677 B2 | 2/2007 | Kaula et al. |
| 7,195,592 B2 | 3/2007 | Ravikumar et al. |
| 7,207,949 B2 | 4/2007 | Miles et al. |
| 7,211,098 B2 | 5/2007 | Dallara et al. |
| 7,217,273 B2 | 5/2007 | Bonutti |
| 7,223,233 B2 | 5/2007 | Branch et al. |
| 7,235,064 B2 | 6/2007 | Hopper et al. |
| 7,261,688 B2 | 8/2007 | Smith et al. |
| 7,294,136 B2 | 11/2007 | Dubrul et al. |
| 7,311,719 B2 | 12/2007 | Bonutti |
| 7,326,226 B2 | 2/2008 | Root et al. |
| 7,329,268 B2 | 2/2008 | Van Nguyen et al. |
| 7,344,495 B2 | 3/2008 | Ravikumar et al. |
| 7,374,534 B2 | 5/2008 | Dalton |
| 7,390,298 B2 | 6/2008 | Chu |
| 7,396,329 B2 | 7/2008 | Nakao |
| 7,407,483 B2 | 8/2008 | Perez-Cruet et al. |
| 7,435,219 B2 | 10/2008 | Kim |
| 7,455,639 B2 | 11/2008 | Ritland |
| 7,458,933 B2 | 12/2008 | LeVahn et al. |
| 7,470,236 B1 | 12/2008 | Kelleher et al. |
| 7,473,222 B2 | 1/2009 | Dewey et al. |
| 7,476,232 B2 | 1/2009 | Deal |
| 7,488,337 B2 | 2/2009 | Saab et al. |
| 7,491,168 B2 | 2/2009 | Raymond et al. |
| 7,510,524 B2 | 3/2009 | Vayser et al. |
| 7,513,869 B2 | 4/2009 | Branch et al. |
| 7,522,953 B2 | 4/2009 | Kaula et al. |
| 7,556,600 B2 | 7/2009 | Landry et al. |
| 7,582,058 B1 | 9/2009 | Miles et al. |
| 7,594,888 B2 | 9/2009 | Raymond et al. |
| 7,641,664 B2 | 1/2010 | Pagano |
| 7,645,232 B2 | 1/2010 | Shluzas |
| 7,682,378 B2 | 3/2010 | Truckai et al. |
| 7,683,565 B2 | 3/2010 | Quaid et al. |
| 7,686,492 B2 | 3/2010 | Vayser et al. |
| 7,691,057 B2 | 4/2010 | Miles et al. |
| 7,691,657 B2 | 4/2010 | Lee |
| 7,693,562 B2 | 4/2010 | Marino et al. |
| 7,704,267 B2 | 4/2010 | Tessmer |
| 7,744,612 B2 | 6/2010 | Blain |
| 7,747,311 B2 | 6/2010 | Quaid, III |
| 7,758,501 B2 | 7/2010 | Frasier et al. |
| 7,780,594 B2 | 8/2010 | Hutton |
| 7,785,253 B1 * | 8/2010 | Arambula ............... A61B 1/32 |
| | | 600/219 |
| 7,811,230 B2 * | 10/2010 | Hsueh ............... A61B 17/0293 |
| | | 600/210 |
| 7,819,801 B2 | 10/2010 | Miles et al. |
| 7,850,608 B2 | 12/2010 | Hamada |
| 7,874,982 B2 | 1/2011 | Selover et al. |
| 7,883,522 B2 | 2/2011 | Hamada |
| 7,887,482 B2 | 2/2011 | Hamada |
| 7,891,801 B2 | 2/2011 | Nakajima |
| 7,892,173 B2 | 2/2011 | Miles et al. |
| 7,905,840 B2 | 3/2011 | Pimenta et al. |
| 7,909,761 B2 | 3/2011 | Banchieri et al. |
| 7,909,832 B2 | 3/2011 | Michelson |
| 7,918,891 B1 | 4/2011 | Curran et al. |
| 7,920,922 B2 | 4/2011 | Gharib et al. |
| 7,931,589 B2 | 4/2011 | Cohen et al. |
| 7,935,051 B2 | 5/2011 | Miles et al. |
| 7,935,053 B2 | 5/2011 | Karpowicz et al. |
| 7,946,982 B2 | 5/2011 | Hamada |
| 7,962,191 B2 | 6/2011 | Marino et al. |
| 7,963,927 B2 | 6/2011 | Kelleher et al. |
| 7,976,463 B2 | 7/2011 | Dewey et al. |
| 7,981,029 B2 | 7/2011 | Branch et al. |
| 7,985,179 B2 | 7/2011 | Gephart et al. |
| 7,988,623 B2 | 8/2011 | Pagliuca et al. |
| 7,988,624 B2 | 8/2011 | Smith et al. |
| 7,991,463 B2 | 8/2011 | Kelleher et al. |
| 8,000,782 B2 | 8/2011 | Gharib et al. |
| 8,005,535 B2 | 8/2011 | Gharib et al. |
| 8,010,180 B2 | 8/2011 | Quaid et al. |
| 8,016,767 B2 | 9/2011 | Miles et al. |
| 8,027,716 B2 | 9/2011 | Gharib et al. |
| 8,050,769 B2 | 11/2011 | Gharib et al. |
| 8,055,349 B2 | 11/2011 | Gharib et al. |
| 8,062,217 B2 | 11/2011 | Boucher et al. |
| 8,062,303 B2 | 11/2011 | Berry et al. |
| 8,068,912 B2 | 11/2011 | Kaula et al. |
| D652,519 S | 1/2012 | Miles et al. |
| D652,921 S | 1/2012 | Miles et al. |
| D652,922 S | 1/2012 | Miles et al. |
| 8,090,436 B2 | 1/2012 | Hoey et al. |
| 8,095,200 B2 | 1/2012 | Quaid, III |
| 8,105,236 B2 | 1/2012 | Malandain et al. |
| 8,114,019 B2 | 2/2012 | Miles et al. |
| 8,114,161 B2 | 2/2012 | Evans et al. |
| 8,114,689 B2 | 2/2012 | Kang et al. |
| 8,133,173 B2 | 3/2012 | Miles et al. |
| 8,137,284 B2 | 3/2012 | Miles et al. |
| 8,152,721 B2 | 4/2012 | Michaeli et al. |
| 8,157,728 B2 | 4/2012 | Danna et al. |
| 8,165,653 B2 | 4/2012 | Marino et al. |
| 8,172,750 B2 | 5/2012 | Miles et al. |
| 8,182,423 B2 | 5/2012 | Miles et al. |
| 8,187,179 B2 | 5/2012 | Miles et al. |
| 8,187,334 B2 | 5/2012 | Curran et al. |
| 8,192,356 B2 | 6/2012 | Miles et al. |
| 8,192,357 B2 | 6/2012 | Miles et al. |
| 8,206,293 B2 | 6/2012 | Reglos et al. |
| D666,292 S | 8/2012 | Miles et al. |
| D666,293 S | 8/2012 | Miles et al. |
| D666,294 S | 8/2012 | Miles et al. |
| 8,244,343 B2 | 8/2012 | Gharib et al. |
| 8,246,686 B1 | 8/2012 | Curran et al. |
| 8,265,744 B2 | 9/2012 | Gharib et al. |
| 8,287,522 B2 | 10/2012 | Moses et al. |
| 8,298,139 B2 | 10/2012 | Hamada |
| 8,303,498 B2 | 11/2012 | Miles et al. |
| 8,303,499 B2 | 11/2012 | Hamada |
| 8,303,515 B2 | 11/2012 | Miles et al. |
| 8,317,693 B2 | 11/2012 | Grey et al. |
| 8,323,185 B2 | 12/2012 | Perez-Cruet et al. |
| 8,337,410 B2 | 12/2012 | Kelleher et al. |
| 8,343,046 B2 | 1/2013 | Miles et al. |
| 8,343,065 B2 | 1/2013 | Bartol et al. |
| 8,343,079 B2 | 1/2013 | Bartol et al. |
| 8,348,837 B2 | 1/2013 | Wenchell |
| 8,353,826 B2 | 1/2013 | Weiman |
| 8,355,780 B2 | 1/2013 | Miles et al. |
| 8,361,156 B2 | 1/2013 | Curran et al. |
| 8,376,937 B2 | 2/2013 | Xia et al. |
| 8,388,527 B2 | 3/2013 | Miles et al. |
| 8,403,841 B2 | 3/2013 | Miles et al. |
| 8,409,089 B2 | 4/2013 | Michaeli et al. |
| 8,430,813 B2 | 4/2013 | Selover et al. |
| 8,439,832 B2 | 5/2013 | Miles et al. |

(56) References Cited

U.S. PATENT DOCUMENTS

| | | |
|---|---|---|
| 8,449,463 B2 | 5/2013 | Nunley et al. |
| 8,454,504 B2 | 6/2013 | Michaeli et al. |
| 8,480,704 B2 | 7/2013 | Heiges et al. |
| 8,489,170 B2 | 7/2013 | Marino et al. |
| 8,491,471 B2 | 7/2013 | Deshmukh et al. |
| 8,500,634 B2 | 8/2013 | Miles et al. |
| 8,512,235 B2 | 8/2013 | Miles et al. |
| 8,517,954 B2 | 8/2013 | Bartol et al. |
| 8,523,767 B2 | 9/2013 | DeRidder et al. |
| 8,523,768 B2 | 9/2013 | Miles et al. |
| 8,545,531 B2 | 10/2013 | Geist et al. |
| 8,548,579 B2 | 10/2013 | Gharib et al. |
| 8,550,994 B2 | 10/2013 | Miles et al. |
| 8,556,808 B2 | 10/2013 | Miles et al. |
| 8,562,521 B2 | 10/2013 | Miles et al. |
| 8,562,539 B2 | 10/2013 | Marino |
| 8,568,317 B1 | 10/2013 | Gharib et al. |
| 8,571,628 B2 | 10/2013 | Kang et al. |
| 8,574,301 B2 | 11/2013 | Curran et al. |
| 8,585,762 B2 | 11/2013 | Hall |
| 8,591,432 B2 | 11/2013 | Pimenta et al. |
| 8,591,567 B2 | 11/2013 | Chau et al. |
| 8,602,982 B2 | 12/2013 | Miles et al. |
| 8,602,984 B2 | 12/2013 | Raymond et al. |
| 8,608,652 B2 | 12/2013 | Voegele et al. |
| 8,608,804 B2 | 12/2013 | Curran et al. |
| 8,622,897 B2 | 1/2014 | Raymond et al. |
| 8,628,469 B2 | 1/2014 | Miles et al. |
| 8,634,904 B2 | 1/2014 | Kaula et al. |
| 8,635,725 B2 | 1/2014 | Tannoury et al. |
| 8,636,656 B2 | 1/2014 | Nichter et al. |
| 8,636,657 B2 | 1/2014 | Hamada |
| 8,641,638 B2 | 2/2014 | Kelleher et al. |
| 8,663,100 B2 | 3/2014 | Miles et al. |
| 8,663,102 B2 | 3/2014 | Michaeli et al. |
| 8,672,840 B2 | 3/2014 | Miles et al. |
| 8,679,006 B2 | 3/2014 | Miles et al. |
| 8,685,105 B2 | 4/2014 | Curran et al. |
| 8,696,559 B2 | 4/2014 | Miles et al. |
| 8,702,600 B2 | 4/2014 | Perrow |
| 8,708,899 B2 | 4/2014 | Miles et al. |
| 8,738,123 B2 | 5/2014 | Gharib et al. |
| 8,747,307 B2 | 6/2014 | Miles et al. |
| 8,753,270 B2 | 6/2014 | Miles et al. |
| 8,753,271 B1 | 6/2014 | Miles et al. |
| 8,758,236 B2 | 6/2014 | Albrecht et al. |
| 8,764,649 B2 | 7/2014 | Miles et al. |
| 8,768,450 B2 | 7/2014 | Gharib et al. |
| 8,795,167 B2 | 8/2014 | Ainsworth et al. |
| 8,801,608 B2 | 8/2014 | Hardenbrook |
| 8,808,172 B2 | 8/2014 | Manzanares |
| 8,812,116 B2 | 8/2014 | Kaula et al. |
| 8,814,940 B2 | 8/2014 | Curran et al. |
| 8,821,394 B2 | 9/2014 | Hawkins et al. |
| 8,821,396 B1 | 9/2014 | Miles et al. |
| 8,852,089 B2 | 10/2014 | Blackwell et al. |
| 8,855,822 B2 | 10/2014 | Bartol et al. |
| 8,870,760 B2 | 10/2014 | Heiges et al. |
| 8,876,687 B2 | 11/2014 | Jones et al. |
| 8,882,661 B2 | 11/2014 | Hutton et al. |
| 8,882,679 B2 | 11/2014 | Bartol et al. |
| 8,892,259 B2 | 11/2014 | Bartol et al. |
| 8,894,574 B2 | 11/2014 | Ellman |
| 8,900,137 B1 | 12/2014 | Lovell et al. |
| 8,911,364 B2 | 12/2014 | Feigenwinter et al. |
| 8,915,846 B2 | 12/2014 | Miles et al. |
| 8,932,360 B2 | 1/2015 | Womble et al. |
| 8,942,797 B2 | 1/2015 | Bartol et al. |
| 8,942,801 B2 | 1/2015 | Miles et al. |
| 8,945,004 B2 | 2/2015 | Miles et al. |
| 8,956,283 B2 | 2/2015 | Miles et al. |
| 8,958,869 B2 | 2/2015 | Kelleher et al. |
| 8,968,363 B2 | 3/2015 | Weiman et al. |
| 8,977,352 B2 | 3/2015 | Gharib et al. |
| 8,979,767 B2 | 3/2015 | Bartol et al. |
| 8,983,593 B2 | 3/2015 | Bartol et al. |
| 8,986,344 B2 | 3/2015 | Sandhu |
| 8,992,425 B2 | 3/2015 | Karpowicz et al. |
| 8,992,558 B2 | 3/2015 | Stone et al. |
| 9,014,776 B2 | 4/2015 | Marino et al. |
| 9,037,250 B2 | 5/2015 | Kaula et al. |
| 9,039,630 B2 | 5/2015 | Bartol et al. |
| 9,044,280 B1 | 6/2015 | Arambula et al. |
| 9,050,146 B2 | 6/2015 | Woolley et al. |
| 9,060,757 B2 | 6/2015 | Lawson et al. |
| 9,066,701 B1 | 6/2015 | Finley et al. |
| 9,084,550 B1 | 7/2015 | Bartol et al. |
| 9,095,301 B2 | 8/2015 | Hamada |
| 9,113,854 B2 | 8/2015 | Ellman |
| 9,125,587 B2 | 9/2015 | Hawkins et al. |
| 9,138,137 B2 | 9/2015 | Deshmukh et al. |
| 9,138,217 B2 | 9/2015 | Smith et al. |
| 9,180,021 B2 | 11/2015 | Curran et al. |
| 9,204,871 B2 | 12/2015 | Miles et al. |
| 9,206,947 B2 | 12/2015 | Baumgartner et al. |
| 9,220,491 B2 | 12/2015 | Nunley et al. |
| 9,259,144 B2 | 2/2016 | Smith et al. |
| 9,265,493 B2 | 2/2016 | Miles et al. |
| 9,271,709 B2 | 3/2016 | Grey et al. |
| 9,271,711 B2 | 3/2016 | Hawkins et al. |
| 9,301,711 B2 | 4/2016 | Bartol et al. |
| 9,301,743 B2 | 4/2016 | Miles et al. |
| 9,314,152 B2 | 4/2016 | Pimenta et al. |
| 9,320,506 B2 | 4/2016 | Bertagnoli et al. |
| 9,339,263 B2 | 5/2016 | Fenn et al. |
| 9,351,718 B1 | 5/2016 | Arambula et al. |
| 9,380,932 B1 | 7/2016 | Lynn et al. |
| 9,386,916 B2 | 7/2016 | Predick et al. |
| 9,387,009 B2 | 7/2016 | Fatone et al. |
| 9,408,598 B1 | 8/2016 | Fantini et al. |
| 9,429,746 B2 | 8/2016 | Vayser et al. |
| 9,458,935 B2 | 10/2016 | Fricke et al. |
| 9,480,855 B2 | 11/2016 | DiMauro et al. |
| 9,486,133 B2 | 11/2016 | Coleman et al. |
| 9,498,200 B2 | 11/2016 | Pfabe et al. |
| 9,554,789 B2 | 1/2017 | Overes et al. |
| 9,572,560 B2 | 2/2017 | Mast et al. |
| 9,610,130 B2 | 4/2017 | Vayser et al. |
| 9,615,818 B2 | 4/2017 | Baudouin et al. |
| 9,636,097 B2 | 5/2017 | Bass |
| 9,642,607 B2 | 5/2017 | Bootwala |
| 9,649,101 B2 | 5/2017 | Karpowicz et al. |
| 9,655,505 B1 | 5/2017 | Gharib et al. |
| 9,693,761 B2 | 7/2017 | Fedorov et al. |
| 9,782,158 B2 | 10/2017 | Nunley et al. |
| 9,795,370 B2 | 10/2017 | O'Connell et al. |
| 9,808,231 B2 | 11/2017 | Miraki et al. |
| 9,808,232 B2 | 11/2017 | Heiman et al. |
| 9,848,863 B2 | 12/2017 | Cryder et al. |
| 9,968,347 B2 | 5/2018 | Hutton et al. |
| 10,004,488 B2 | 6/2018 | Simonson |
| 10,046,149 B2 | 8/2018 | Bootwala |
| 10,172,515 B2 | 1/2019 | Coleman et al. |
| 10,188,376 B2 | 1/2019 | Miraki et al. |
| 10,548,738 B2 | 2/2020 | Milz et al. |
| 2001/0039430 A1 | 11/2001 | Dubrul et al. |
| 2002/0193822 A1 | 12/2002 | Hung et al. |
| 2003/0018352 A1 | 1/2003 | Mollenauer et al. |
| 2003/0023259 A1 | 1/2003 | Dubrul et al. |
| 2003/0181939 A1 | 9/2003 | Bonutti |
| 2003/0191371 A1 | 10/2003 | Smith et al. |
| 2003/0195405 A1 | 10/2003 | Marino et al. |
| 2003/0225432 A1 | 12/2003 | Baptiste et al. |
| 2003/0225433 A1 | 12/2003 | Nakao |
| 2003/0229273 A1 | 12/2003 | Mulac et al. |
| 2003/0233115 A1 | 12/2003 | Eversull et al. |
| 2004/0087833 A1 | 5/2004 | Bauer et al. |
| 2004/0236186 A1 | 11/2004 | Chu |
| 2004/0243158 A1 | 12/2004 | Konstantino et al. |
| 2004/0243167 A1 | 12/2004 | Tanaka et al. |
| 2005/0119531 A1 | 6/2005 | Sharratt |
| 2005/0124937 A1 | 6/2005 | Kick et al. |
| 2005/0182436 A1 | 8/2005 | Chopra |
| 2005/0234304 A1 | 10/2005 | Dewey et al. |

(56) References Cited

U.S. PATENT DOCUMENTS

| | | |
|---|---|---|
| 2005/0234493 A1 | 10/2005 | Carr et al. |
| 2006/0004398 A1 | 1/2006 | Binder et al. |
| 2006/0052750 A1 | 3/2006 | Lenker et al. |
| 2006/0135852 A1 | 6/2006 | Koros et al. |
| 2006/0135981 A1 | 6/2006 | Lenker et al. |
| 2006/0135987 A1 | 6/2006 | Jones et al. |
| 2006/0206008 A1 | 9/2006 | Dalton |
| 2006/0206009 A1 | 9/2006 | Von Wald et al. |
| 2006/0224044 A1 | 10/2006 | Marchek et al. |
| 2006/0224045 A1 | 10/2006 | Whipple et al. |
| 2006/0224078 A1 | 10/2006 | Hoey et al. |
| 2006/0258951 A1 | 11/2006 | Bleich et al. |
| 2006/0287574 A1 | 12/2006 | Chin |
| 2007/0010716 A1 | 1/2007 | Malandain et al. |
| 2007/0032703 A1 | 2/2007 | Sankaran et al. |
| 2007/0049962 A1 | 3/2007 | Marino et al. |
| 2007/0060939 A1 | 3/2007 | Lancial et al. |
| 2007/0168043 A1 | 7/2007 | Ferree |
| 2007/0208366 A1 | 9/2007 | Pellegrino et al. |
| 2007/0213591 A1 | 9/2007 | Aizenfeld et al. |
| 2007/0219416 A1 | 9/2007 | Perez-Cruet et al. |
| 2007/0239159 A1 | 10/2007 | Altarac et al. |
| 2007/0270623 A1 | 11/2007 | Merrill |
| 2007/0270653 A1 | 11/2007 | Vayser et al. |
| 2008/0058606 A1 | 3/2008 | Miles et al. |
| 2008/0064945 A1 | 3/2008 | Marino et al. |
| 2008/0065135 A1 | 3/2008 | Marino et al. |
| 2008/0065140 A1 | 3/2008 | Bonutti |
| 2008/0065144 A1 | 3/2008 | Marino et al. |
| 2008/0065178 A1 | 3/2008 | Kelleher et al. |
| 2008/0071191 A1 | 3/2008 | Kelleher et al. |
| 2008/0103519 A1 | 5/2008 | Bonutti |
| 2008/0109026 A1 | 5/2008 | Kassam |
| 2008/0132764 A1 | 6/2008 | Hamada |
| 2008/0147109 A1 | 6/2008 | Kambin et al. |
| 2008/0183204 A1 | 7/2008 | Greenhalgh et al. |
| 2008/0215081 A1 | 9/2008 | Hsueh et al. |
| 2008/0221586 A1 | 9/2008 | Garcia-Bengochea et al. |
| 2008/0255563 A1 | 10/2008 | Farr et al. |
| 2008/0319268 A1 | 12/2008 | Michaeli et al. |
| 2008/0319432 A1 | 12/2008 | Ely et al. |
| 2009/0024158 A1 | 1/2009 | Viker |
| 2009/0036744 A1 | 2/2009 | Vayser |
| 2009/0036746 A1 | 2/2009 | Blackwell et al. |
| 2009/0062871 A1 | 3/2009 | Chin et al. |
| 2009/0149716 A1 | 6/2009 | Diao et al. |
| 2009/0171284 A1 | 7/2009 | Burke et al. |
| 2010/0041955 A1 | 2/2010 | Grey et al. |
| 2010/0160947 A1 | 6/2010 | Akyuz et al. |
| 2010/0178100 A1 | 7/2010 | Fricke et al. |
| 2010/0180906 A1 | 7/2010 | Marozsan et al. |
| 2010/0241129 A1 | 9/2010 | Markey et al. |
| 2011/0208005 A1 | 8/2011 | Michaeli et al. |
| 2011/0237898 A1* | 9/2011 | Stone ............... A61B 17/0293 600/205 |
| 2011/0313312 A1 | 12/2011 | Hoey et al. |
| 2012/0010472 A1 | 1/2012 | Spann |
| 2012/0022575 A1 | 1/2012 | Mire et al. |
| 2012/0029382 A1 | 2/2012 | Kelleher et al. |
| 2012/0035730 A1 | 2/2012 | Spann |
| 2012/0041272 A1 | 2/2012 | Dietze, Jr. et al. |
| 2012/0046526 A1 | 2/2012 | Boettner et al. |
| 2012/0101341 A1 | 4/2012 | Malandain et al. |
| 2012/0232349 A1 | 9/2012 | Perrow |
| 2013/0090680 A1 | 4/2013 | Akyuz et al. |
| 2013/0103103 A1 | 4/2013 | Mire et al. |
| 2013/0123582 A1 | 5/2013 | Xia et al. |
| 2013/0190575 A1 | 7/2013 | Mast et al. |
| 2013/0211202 A1 | 8/2013 | Perez-Cruet et al. |
| 2013/0317303 A1 | 11/2013 | Deshmukh et al. |
| 2014/0039264 A1 | 2/2014 | Heiman |
| 2014/0114135 A1 | 4/2014 | Ellman |
| 2014/0114138 A1 | 4/2014 | Fedorov et al. |
| 2014/0114139 A1 | 4/2014 | Ziolo et al. |
| 2014/0128979 A1 | 5/2014 | Womble et al. |
| 2014/0142420 A1 | 5/2014 | Jackson, III |
| 2014/0148650 A1 | 5/2014 | Miles et al. |
| 2014/0172002 A1 | 6/2014 | Predick |
| 2014/0235950 A1 | 8/2014 | Miles et al. |
| 2014/0257035 A1 | 9/2014 | Blain |
| 2014/0257044 A1 | 9/2014 | Blain et al. |
| 2014/0275801 A1 | 9/2014 | Menchaca et al. |
| 2014/0276869 A1 | 9/2014 | Tatsumi |
| 2014/0288374 A1 | 9/2014 | Miles et al. |
| 2014/0288375 A1 | 9/2014 | Miles et al. |
| 2014/0316212 A1 | 10/2014 | Reimels |
| 2014/0357946 A1 | 12/2014 | Golden et al. |
| 2015/0018623 A1 | 1/2015 | Friedrich et al. |
| 2015/0018625 A1 | 1/2015 | Miraki et al. |
| 2015/0045626 A1 | 2/2015 | Reimels |
| 2015/0051448 A1 | 2/2015 | Hunt et al. |
| 2015/0051506 A1 | 2/2015 | Wybo et al. |
| 2015/0051507 A1 | 2/2015 | Wybo et al. |
| 2015/0080717 A1 | 3/2015 | Ferko |
| 2015/0088029 A1 | 3/2015 | Wybo |
| 2015/0088030 A1 | 3/2015 | Taylor |
| 2015/0105624 A1 | 4/2015 | Martinelli et al. |
| 2015/0112148 A1 | 4/2015 | Bouquet |
| 2015/0119987 A1 | 4/2015 | Davignon et al. |
| 2015/0133734 A1 | 5/2015 | Miles et al. |
| 2015/0150693 A1 | 6/2015 | Gharib et al. |
| 2015/0157227 A1 | 6/2015 | Kelleher et al. |
| 2015/0157228 A1 | 6/2015 | Marino et al. |
| 2015/0164496 A1 | 6/2015 | Karpowicz et al. |
| 2015/0164569 A1 | 6/2015 | Reitblat et al. |
| 2015/0216478 A1 | 8/2015 | Kaula et al. |
| 2015/0230749 A1 | 8/2015 | Gharib et al. |
| 2015/0230787 A1 | 8/2015 | Friedrich et al. |
| 2015/0257784 A1 | 9/2015 | Corbin et al. |
| 2015/0327948 A1 | 11/2015 | Schoepp et al. |
| 2015/0342589 A1 | 12/2015 | Bootwala |
| 2015/0366548 A1 | 12/2015 | Lauchner |
| 2016/0038302 A1 | 2/2016 | Curran et al. |
| 2016/0051242 A1 | 2/2016 | Predick et al. |
| 2016/0081681 A1 | 3/2016 | Waugh et al. |
| 2016/0081682 A1 | 3/2016 | Miles et al. |
| 2016/0120530 A1 | 5/2016 | Miles et al. |
| 2016/0120532 A1 | 5/2016 | Donald |
| 2016/0174958 A1 | 6/2016 | Miles et al. |
| 2016/0174959 A1 | 6/2016 | Miles et al. |
| 2016/0183913 A1 | 6/2016 | Singh et al. |
| 2016/0192921 A1 | 7/2016 | Pimenta et al. |
| 2016/0192922 A1 | 7/2016 | Friedrich et al. |
| 2016/0199193 A1 | 7/2016 | Willis et al. |
| 2016/0242736 A1 | 8/2016 | Freiburg et al. |
| 2016/0278755 A1 | 9/2016 | Stone et al. |
| 2016/0338795 A1 | 11/2016 | Vayser et al. |
| 2016/0345949 A1 | 12/2016 | Harvey et al. |
| 2016/0361052 A1 | 12/2016 | Reimels |
| 2017/0000562 A1 | 1/2017 | Frank et al. |
| 2017/0007228 A1 | 1/2017 | Costabile |
| 2017/0014118 A1 | 1/2017 | Capote |
| 2017/0014119 A1 | 1/2017 | Capote et al. |
| 2017/0027555 A1 | 2/2017 | Paumier et al. |
| 2017/0065268 A1 | 3/2017 | Sindram |
| 2017/0071589 A1 | 3/2017 | Simonson |
| 2017/0150956 A1 | 6/2017 | Baudouin et al. |
| 2017/0215856 A1 | 8/2017 | Martinelli et al. |
| 2017/0231614 A1 | 8/2017 | Vogel et al. |
| 2017/0340317 A1 | 11/2017 | Fatone et al. |
| 2018/0064450 A1 | 3/2018 | Jackson, III |
| 2018/0333152 A1 | 11/2018 | Heiman |

FOREIGN PATENT DOCUMENTS

| | | | |
|---|---|---|---|
| WO | 9916499 | A1 | 4/1999 |
| WO | 2006102085 | A2 | 9/2006 |
| WO | 2008039427 | A2 | 4/2008 |

(56) References Cited

FOREIGN PATENT DOCUMENTS

| WO | 2009137700 A1 | 11/2009 |
|---|---|---|
| WO | 2018039228 A1 | 3/2018 |

OTHER PUBLICATIONS

Popejoy et al., U.S. Appl. No. 62/546,796, filed Aug. 17, 2017, titled "Bridges and Lighting for Lateral Access".
Wills et al., U.S. Appl. No. 62/103,276, filed Jan. 14, 2015, titled "Spinal Implant With Porous and Solid Surfaces".
Milz et al., U.S. Appl. No. 62/560,910, filed Sep. 20, 2017, titled "Spinal Implants".
International Search Report for Application No. PCT/US2017/048009 dated Dec. 11, 2017, 7 pages.
Bush et al., U.S. Appl. No. 62/546,841, filed Aug. 17, 2017, titled "Independent Rod Suspension".
Milz et al., U.S. Appl. No. 62/319,513, filed Apr. 7, 2016, titled "Expandable Interbody Implant.".
Biomet Spine; AccuVision Minimally Invasive Spinal Exposure System, Surgical Technique Dec. 2009, 28 pages.
Aesculap Spine; Caspar Cervical Retractor System, Product Brochure Apr. 2009 Doc# 510, 16 pages.
Zimmer; ARAS Retractor, Surgical Technique L1377 Rev. A 2007, 20 pages.
Depuy; Pipeline Concorde, Surgical Technique Jul. 2007 M102-20-001, 24 pages.
Zimmer Spine; Harmony Retractor System, Surgical Technique L1477 Rev. A Aug. 2009, 20 pages.
Lanx; Timberline Lateral Fusion System, Surgical Technique LIT8710-0111.03, copyright 2012, Lanx Inc., Broomfield, CO. 42 pages.
Medtronic; Mast Quadrant, Product Brochure 2005 MLITQUDST5, 40 pages.
Synthes; Oracle Spacer, Technique Guide Dec. 2010 J8158-C, 40 pages.
K2M; Tera Nova, Product Brochure 2012 K2-15-7002-01 Rev.3, 2 pages.
Biomet Spine; VuePASS, Surgical Technique Jun. 2007 P/N 216001L. 36 pages.
NuVasive; Maxcess-XLIF, Surgical Technique 2007 9500138 A.0, 32 pages.
Biomet Spine, "Timberline Lateral Fusion System, Surgical Technique Guide", Copyright 2014, 52 pages.
International Search Report for Application No. PCT/US2009/068474 dated Aug. 9, 2010.
International Search Report for Application No. PCT/US2011/032525 dated Dec. 15, 2011.
Extended European Search Report for Application No. 09837915.9 dated Mar. 28, 2014.
Partial European Search Report including Provisional Opinion for EP19166059.6 dated Aug. 26, 2019.
Extended European Search Report including Written Opinion for Application No. EP19166059.6, dated Nov. 29, 2019, pp. 1-11.

* cited by examiner

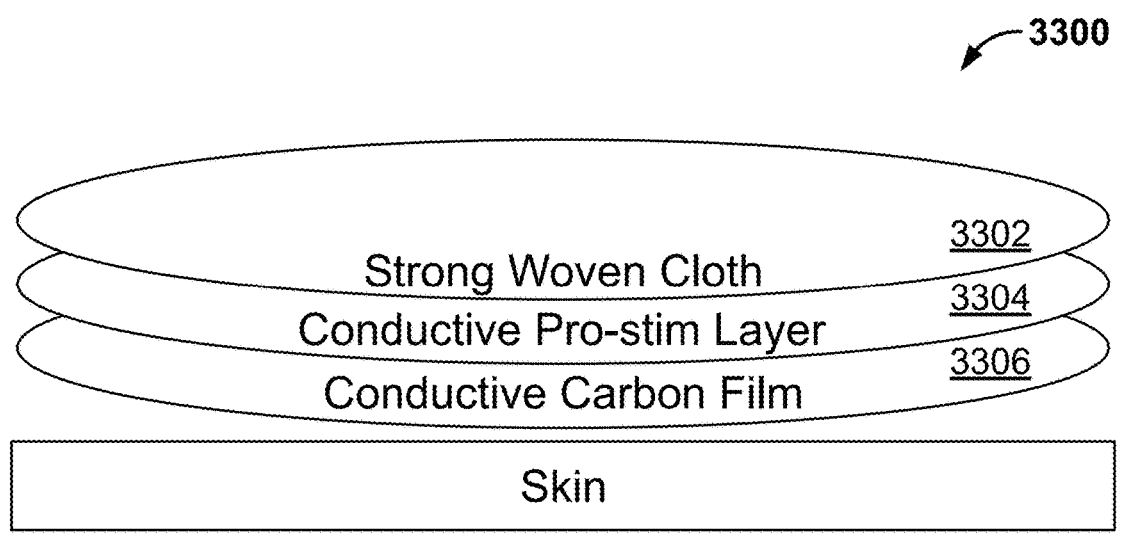
FIG. 49A
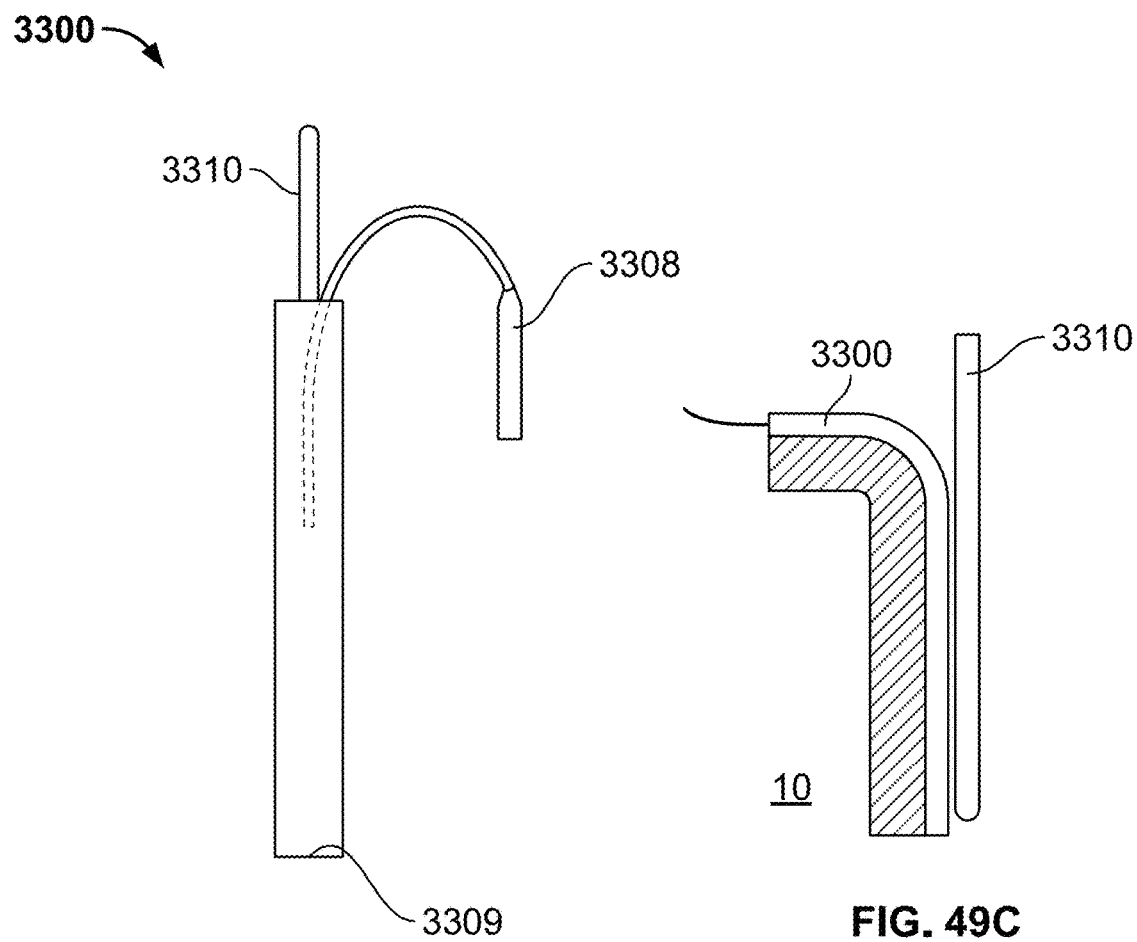
FIG. 49B  FIG. 49C

LATERAL ACCESS RETRACTOR AND CORE INSERTION

CROSS-REFERENCE TO RELATED APPLICATIONS

The present application is a continuation of U.S. patent application Ser. No. 16/369,139 filed Mar. 29, 2019, which claims the benefit of the filing date of U.S. Provisional Patent Application No. 62/650,671 filed Mar. 30, 2018, the disclosures of which are hereby incorporated by reference herein in their entirety.

BACKGROUND OF THE INVENTION

Retractor devices are used in many surgical contexts to create a corridor for accessing a target site, such as an intervertebral disc in a spine or locations accessible through the thoracic cavity. The performance of these devices becomes particularly important in minimally invasive surgical procedures.

Because excess enlargement of a surgical access corridor is undesirable, a problem exists with the structure and retraction paths of many existing retraction devices. In particular, many retractors include three or four blades where each blade only moves along a single axis. With these retractors, a surgical portal can only be created in one shape that is based on the shape of each blade. Where an implant would otherwise only require an amount of clearance on each side of its surface for insertion based on the size of the implant, such existing retractors necessarily require the creation of a portal significantly larger than would otherwise be required in order to capture a space needed on all sides of the implant. For instance, many three blade retractors require an initial placement of dilators to create the initial portal for the placement of the retractor while in the closed position, making the procedure for creation of an access corridor more tedious and making it slower in circumstances where time is often limited. Other challenges faced when employing existing retractor technologies include the limited degrees of freedom in which retractor blades may be manipulated. These functional impediments make it more difficult to customize rod positions for a particular surgery, such as adjusting a depth of one rod relative to another and toeing the same rod to compensate for and limit tissue creep into the working portal.

Thus, there is a need for improved surgical retraction structures and methods for creating access to an anatomical site to be operated on.

BRIEF SUMMARY OF THE INVENTION

The various aspects of the present disclosure provide improvements including improvements to address the above deficiencies related to minimally invasive surgery. These improvements include, but are not limited to, provision of a retractor with rods that are retractable individually or simultaneously, where any number of the rods of a retractor can be moved in multiple degrees of freedom. The retractor may include a slide tool attached to the frame translatable through a sliding motion to cause the retractor rods to open rapidly. Other components designed to work with the retractor may also be used to position the rods at a predetermined spacing upon insertion, to hold the rods together, or to create the initial working portal prior to inserting the retractor.

In one aspect, the present disclosure relates to a retractor with five rods each having cylindrically shaped interior portions and an arm attachment on an exterior portion. The rods are attached to a retractor frame via arms. The arms include a sliding connection at the frame to translate the arms radially to and from a center of the retractor, a pivoting connection adjacent to the rods so that the rods may be toed inward or outward, and a ratcheting mechanism adjacent to the rods and parallel to their length to adjust the rods toward and away from a plane through the arms and the frame in predetermined increments, as well as hold them in these positions.

In some embodiments, the retractor also includes a U-shaped slide tool. The slide tool is engageable with the retractor frame and is dimensioned to slide under or through a channel(s) of the frame with its edges including ramps. These ramps are shaped to cause pins extending from the retractor arms to move a predetermined amount when the slide tool is pulled from the frame, thereby producing a predetermined rapid opening amount based on the dimensions of the slide tool.

In other embodiments, the retractor may be accompanied by a squid cap with a cavity therein so that it is engageable to a series of rods in contact with one another. The squid cap includes a hollow, generally cylindrical lower body with extensions separated by slots dimensioned to hold the rods in place with respect to one another. In still further embodiments is a central core element with a cylindrical shape, tapered tip, and grooves punctuating the cylindrical surface. The grooves are sized so that rods of the retractor may be disposed therein. The central core element may also include a handle. In yet another embodiment, the retractor may be accompanied by a squid core combination structure for a surgical procedure. The squid core combination structure includes a squid enclosure and a central core, the squid enclosure encapsulating the central core. The central core is similar to that described above with a generally cylindrical shape having grooves therein extending along a length of the core. The squid enclosure includes a unifying cap with squid rods extending therefrom, the rods sized and positioned relative to one another so that when cap is engaged to central core, the squid rods nest in the grooves of the central core. In this combined structure, the squid rods include an outer surface with a larger radius of curvature than an inside surface so that the combined squid rods and central core have a circular cross section.

In still further embodiments, the retractor may be accompanied by a handle to control expansion of the working portal in either or both of the anterior-posterior direction or the cranial-caudal direction, assuming that the surgical approach is lateral. The handle mechanisms are mechanically connected to the arms of the retractor so that actuation of the handle is linked to a movement of an arm or arms.

In one embodiment, a retractor apparatus includes a retractor frame, five arms attached to the retractor frame and five rods each attached to one of the five arms. Each rod includes a convex surface facing a center of the retractor frame. At least two of the five rods are movable independently from one another. A first rod of the five rods includes a longitudinal axis and is translatable along the longitudinal axis. Further, the first rod is attached to a first arm of the five arms and is pivotable relative to the first arm. The axis of pivot is offset from the longitudinal axis through which the first rod translates.

In another aspect, the present disclosure relates to a method of creating a working portal in a patient using a retractor. The retractor includes five arms each having a rod engaged thereon and a rapid opening pin at an opposite end of the rod. A guidewire is aligned at a desired location entering the body and docked at a target site. The retractor is then prepared with a squid cap disposed thereon to keep the rods in contact with one another. Once the retractor is slid over guidewire via a central opening in the squid cap, the closed rods are advanced into the patient. The squid cap is then removed during or following insertion of the rods. Upon full insertion, a slide tool engaged below the retractor frame is translated, through a pulling motion for example, causing rapid opening pins to be caught by ramps on sides of slide tool. Upon engagement of the pins by the ramps, arms connected to the pins are pulled in an external direction away from a center of the retractor frame between the rods. Each arm is pulled simultaneously in this rapid opening step, creating an initial working portal to view a maximum depth of the opening. Additional adjustment of one or more rods may be performed independently at this juncture to customize the size and shape of the working portal.

In another aspect, the present disclosure relates to a retractor apparatus with a retractor frame, five arms attached to the retractor frame and five rods, each rod including a convex surface facing a center of the retractor frame and attached to one of the five arms. Two of the five rods are movable independently from one another in the structure and a first rod of the five rods includes a longitudinal axis and is translatable along the longitudinal axis. Additionally, wherein the first rod is pivotable relative to a first arm of the five arms it is attached to, and the axis of pivot is offset from the longitudinal axis through which the first rod translates.

In one embodiment, the retractor includes a rotating support attached to the retractor frame such that the first arm is disposed therein, the rotating support rotatable about an axis perpendicular to a plane through the retractor frame so that the first rod is swingable in the plane. In a variant, the retractor also includes a fixed support immediately adjacent to the rotating support, the fixed support engaged with the fixed support through interlocking surface features so that rotating support is rotatable in predetermined increments. In some variants, the first arm includes a first engagement feature thereon and the rotating support includes an opening therethrough with a second engagement feature thereon, the first arm linearly translatable along its longitudinal axis in predetermined increments through engagement between the first and second engagement features.

In another embodiment, the first arm has a length extending from a first end to a second end, a pivoting component attached to the first arm at the second end, the pivoting component attached to the arm through a pin coincident with the pivot axis and including the first rod movably attached thereon such that the pivoting component separates the first arm and the first rod. In a variant, the first rod is pivotable up to twenty degrees outward and up to two degrees inward from a first rod orientation perpendicular to the first arm. In another variant, the pivoting component includes a first engagement feature extending parallel to the longitudinal axis of the first rod and the rod includes an arm engagement portion with a second engagement feature extending parallel to the longitudinal axis so that rod is linearly translatable along the longitudinal axis in predetermined increments.

In other embodiments, the five rods are cylindrical in shape. In yet another embodiment, wherein at least one rod of the five rods is cannulated through its length, the cannulation having a size sufficient for placement of a guidewire therethrough.

In another embodiment, the retractor is part of a system that also includes a squid cap. The squid cap includes extension portions extending from a perimeter of a central portion such that an open volume exists between the extension portions. Additionally, the squid cap is adapted to enclose and engage an outer envelope of the five rods. In a variant, the five rods are cylindrical in shape. In another variant, the extension portions are separated by slots on an end of the squid cap facing an end of the rods opposed the enclosed end, the slots sized to accommodate a rod therein. In still another variant, the system also includes a probe disposed through a hole in the squid cap so that the probe is positioned in between the five rods. In yet another variant, the probe includes two separate cannulations extending parallel to its longitudinal axis. In still further variants, the central portion has a cylindrical shape and an entirety of the extension portions have a truncated conical shape. In others, the open volume has a diameter sufficient to hold the five rods therein when the rods abut one another.

In another embodiment, the retractor is part of a system that also includes a core structure. The core structure includes longitudinally disposed grooves thereon, each groove shaped so that a rod of the five rods is removably fixed in the groove when disposed therein. In yet another embodiment, the retractor is part of a system that also includes a slide tool. The slide tool is attached to the retractor frame and having a U-shape, the slide tool including an outer edge with plurality of ramps shaped to engage with at least one of the five arms when the slide tool is translated relative to the retractor frame thereby causing the at least one arm to translate away from the center of the retractor frame.

Another aspect of the present disclosure is a system that includes a retractor frame, a plurality of rods, and a slide tool. Each rod of the plurality of rods is attached to the retractor frame while the slide tool is slidably attached to the retractor frame. The slide tool is shaped so that two rods of the plurality of rods simultaneously move apart from one another when the slide tool is moved from a first position to a second position.

In some embodiments, the system also includes a plurality of arms attached to the retractor frame and one of the plurality of rods. In other embodiments, the slide tool is substantially covered by the retractor frame when the slide tool is in the first position. In still further embodiments, the slide tool is U-shaped with an end component and first and second lateral components each extending from the end component.

In a variant, each of the lateral components includes a lateral edge, the lateral edge having a flat portion and a ramp portion, the flat portion parallel to a direction of translation between the first and second positions and the ramp portion angled relative to the first portion. In another variant, the ramp portions of the lateral components are angled and positioned to cause the two rods to move apart when the ramp portions engage and move respective pins extending transverse from the arm holding each of the respective rods. In yet another variant, the lateral edges each extend from the end component to a free end, the ramp portion closer to the end component and the flat portion closer to the free end. In yet another variant, the free ends of the lateral components define end ramps transverse to the flat portion of the lateral edge, the end ramps positioned to cause third and fourth rods to move apart from one another when pins extending transverse from arms connected to the third and fourth rods are engaged and moved by the end ramps. In some examples, the end ramp of each lateral component is movably attached to a remainder of the lateral component such that an angle of the end ramp relative to the flat portion of the lateral edge is adjustable.

In another embodiment, the ramp portion of each lateral component is movably attached to a remainder of the lateral component such that an angle of the ramp portion relative to the flat portion is adjustable. In yet another embodiment, the lateral components each include a sliding engagement mechanism adapted for slidable engagement with the retractor frame.

In another aspect, the present disclosure relates to a squid core system with a squid enclosure and a central core. The squid enclosure includes a unifying cap and a plurality of squid rods each extending from the unifying cap. The central core engaged with the squid enclosure, an outer surface of the central core having a plurality grooves extending longitudinally thereon. Additionally, the plurality of squid rods are sized and positioned relative to one another to nest within respective grooves on the central core such that a maximum outer diameter of the central core is the same for the central core in isolation or with the plurality of squid rods nested therein.

In some embodiments, the squid rods include outward facing surfaces opposite inward facing surfaces nesting in the central core, the outward facing surfaces having a radius of curvature consistent with that of the central core so that a perimeter of the central core is circular when the squid rods are nested in the grooves of the central core. In other embodiments, the central core is engaged to the squid enclosure in a manner so that removal or attachment of the squid enclosure involves translating the squid enclosure in a direction of a longitudinal axis of the central core. In still further embodiments, the grooves of the central core are concave and form a partial circular shape. In other embodiments, the central core includes a tapered tip at an end distal to the unifying cap.

In another aspect, the present disclosure relates to a kit with a retractor frame, a plurality of rotating supports, a plurality of arms, a plurality of rods and a slide tool. The plurality of rotating supports are each adapted for securement to the retractor frame. Each arm of the plurality of arms is adapted for engagement to one of the plurality of rotating supports. Each rod of the plurality of rods is adapted for engagement to one of the plurality of arms while the slide tool is adapted to slidably engage with the retractor frame.

In some embodiments, the plurality of rods are cylindrical in shape. In still further embodiments, the kit also includes a squid cap or central core element configured to engage and hold each of the plurality of rods simultaneously.

Another aspect of the present disclosure relates to a method of creating a surgical portal with steps including: advancing a plurality of retractor rods attached to a retractor frame into tissue of a patient when the plurality of retractor rods are in a first position; and translating a slide tool slidably attached to the retractor frame so that ramps on edges of the slide tool engage arms holding respective rods of the plurality of retractor rods, thereby causing at least two rods of the plurality of retractor rods to retract from one another and move into a second position. The edges of the slide tool used for this method include ramps at an angle relative to a direction of translation of the slide tool and the at least two rods retract while engaged with the slide tool ramps.

In another aspect, the present disclosure relates to a retractor apparatus including a retractor frame, a plurality of arms, a plurality of rods, and a handle. The retractor frame includes a central frame, a first frame extension and a second frame extension. Each of the frame extensions is separately attached to the central frame. The plurality of arms includes a first arm and a second arm attached to the first frame extension. The plurality of arms also includes a third arm and a fourth arm attached to the second frame extension. Each rod of the plurality of rods is attached to a respective one of the plurality of arms. The handle extends from the central frame and includes a first actuation mechanism and a second actuation mechanism. The first actuation mechanism is adjustable to control a distance between the second arm and fourth arm moving in unison relative to the first arm and the third arm. The second actuation mechanism is adjustable to control a distance between the first frame extension and the second frame extension.

In some embodiments, the retractor apparatus may include a first toeing cam on the retractor frame. The first toeing cam may be adapted to control toeing of a pair rods of the plurality of rods that are attached to the first arm and the second arm, respectively. In some embodiments, the retractor apparatus may also include a second toeing cam on the retractor frame. The second toeing cam may be adapted to control toeing of a pair of rods of the plurality of rods that are attached to the third arm and the fourth arm, respectively.

In some embodiments, the retractor apparatus may include a fifth arm having a longitudinal axis. The fifth arm may be attached to the central frame and may be translatable along the longitudinal axis. In some embodiments, the first frame extension and the second frame extension may include a free end remote from the central frame. In some embodiments, the first frame extension and the second frame extension may be symmetrical about a central axis extending through the handle and the central frame. In some embodiments, at least one of the first actuation mechanism and the second actuation mechanism may be accessible from a side of the frame parallel to a plane through the central frame, first frame extension and second frame extension.

BRIEF DESCRIPTION OF THE DRAWINGS

A more complete appreciation of the subject matter of the present disclosure and of the various advantages thereof can be realized by reference to the following detailed description in which reference is made to the accompanying drawings in which:

FIGS. 49A-49C are views of a neuromonitoring patch according to one embodiment of the disclosure.

DETAILED DESCRIPTION

The present disclosure describes various apparatuses, devices, systems, kits and methods to simplify and improve the effectiveness of tissue retraction to create a minimally invasive pathway to access a location to be operated upon, also referred to herein as a target site. The minimally invasive pathway is also referred to as a surgical portal, which is a working volume within a patient undergoing surgery. In the context of procedures using a retractor with retractable rods, the surgical portal represents a working volume generally interior to and between the retracted rods. With a retractor and various supplemental components, such as squid caps, central core elements, and others described in greater detail herein, surgical portals may be created beginning with a very small diameter to minimize risk to the patient upon entry into tissue, a size of a portal can be controlled, particularly in the early steps of a procedure using a squid cap or a central core element, and the expansion of the portal can be customized through opening with all rods or any combination of individual rods of the retractor. A slide tool as described herein may be used to quickly open a surgical portal, a technique known as rapid opening.

The technologies described in this application may be employed in many areas of the body and have particular import where minimally invasive surgery is advantageous. Examples of target anatomy include the cervix, the thoracic cavity, the abdomen for anterior laparoscopy, minimally invasive surgery (MIS) laparotomy or anatomy within the retroperitoneal space, among other procedures, anatomy targeted in cardiac procedures and elements of the nervous system including the brain, cerebrovascular system and the spine. The spine is referenced throughout the application, although it should be appreciated that the concepts described herein are in no way limited to the spine. Approaches to the spine may be lateral, anterior, anterior-lateral, posterior, posterior-lateral or posterior midline. The spine may be accessed for any number of reasons, including treatment of spinal conditions such as disc herniation, implantation of motion preservation devices, total replacement of a disc and implantation of interbody devices, along with many other procedures. Examples of interbody device implantation procedures include lateral lumbar interbody fusion (LLIF), oblique lumbar interbody fusion (OLIF), posterior lumbar interbody fusion (PLIF), anterior lumbar interbody fusion (ALIF), transforaminal lumbar interbody fusion (TLIF), and posterolateral lumbar fusion (PF). As noted above, approaches to the spine are not limited, although the technology described herein is particularly advantageous when employed in a lateral trans-psoas or anterior to psoas approach.

Figure 1:
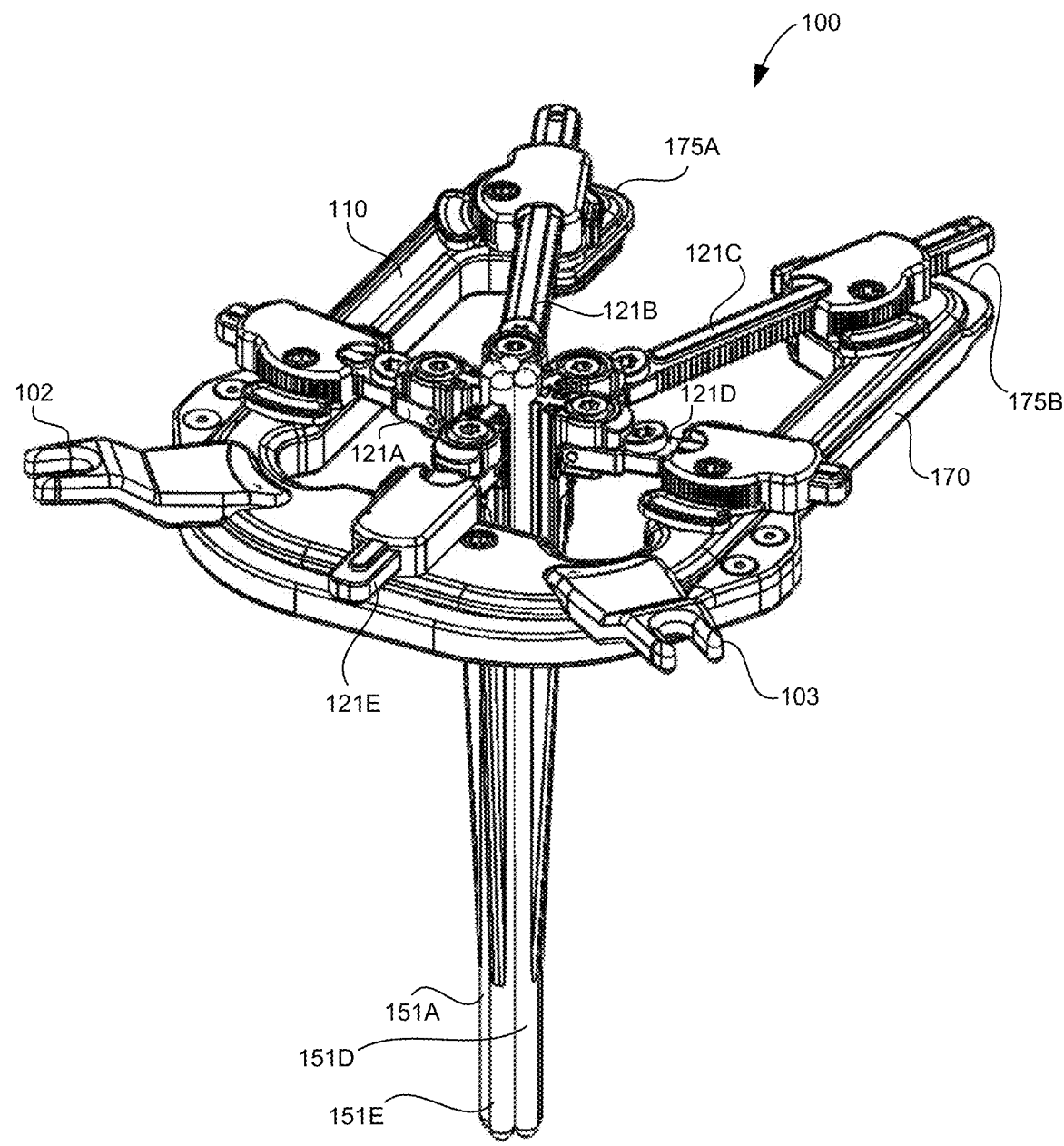
FIG. 1 is a perspective view of a retractor according to one embodiment of the disclosure.

In one aspect, the present disclosure relates to a retractor, one embodiment of which is shown in FIG. 1. Retractor 100 includes a frame 110, connectors 102, 103 attached to frame 110, arms 121A-E attached to frame 110, and five rods 151A-E attached to respective arms 121A-E. Inclusion of five retractor rods makes the retractor quite versatile as the shape of a portal may be customized based on a unique position of each rod to more closely match dimensions of an implant to be placed in a patient. Details of the function of the retractor are described in greater detail below. Retractor 100 also includes a slide tool 170 secured under frame 110 (see FIG. 19A). Each of these components and their relationship with one another will now be described in detail.

Figure 2:
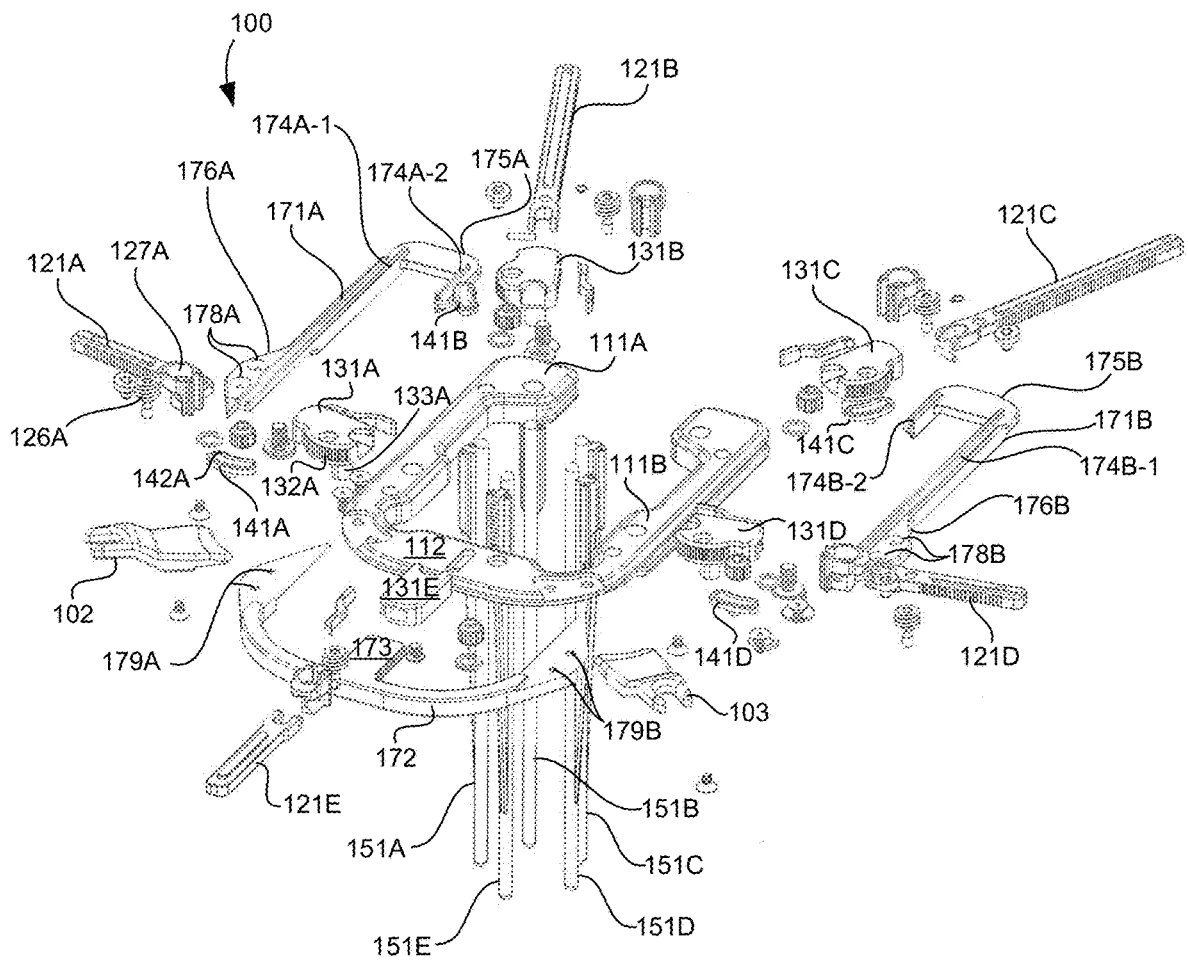
FIG. 2 is an exploded view of the retractor of FIG. 1.

Frame 110 is generally U-shaped, as best shown in FIG. 2, and includes two lateral extensions 111A, 111B and an end portion 112. These segments of the frame are arranged so that each lateral extension mirrors the other and extends from an opposite end of end portion 112. The U-shape of the frame is advantageous in that it provides space on the open side of the frame for visualization, instrument use, and access to patient anatomy. Frame 110 includes apertures, protrusions, and other structural features so that slide tool 170, arms 121A-E and connectors 102, 103 may be secured thereto. However, it is to be understood that the U-shape is but one configuration that may be employed in accordance with the present invention. In one example of a retractor frame having features as depicted in FIG. 1, the frame measures 166 mm in length and 112 mm in width. Of course, the frame may have other dimensions as a matter of design choice. For instance, the frame may have a length less than 166 mm, greater than 200 mm, or any length in between, and a width less than 112 mm, greater than 150 mm, or any width in between. Of course, various combinations of these dimensions and larger sizes are also contemplated.

Turning to arms 121A-E, several accessory components are included so that arms 121A-E are securable to frame 110. For arms 121A-D, these components are generally the same, and like reference numerals refer to like elements. Arm 121E and its accessories are also generally similar, although some features vary slightly. To the extent any particular arm includes distinguishable structure, such structure is outlined in the description below. Arm 121A is now described in detail as representative of each of the five retractor arms shown in FIGS. 1 and 2.

Figure 3:
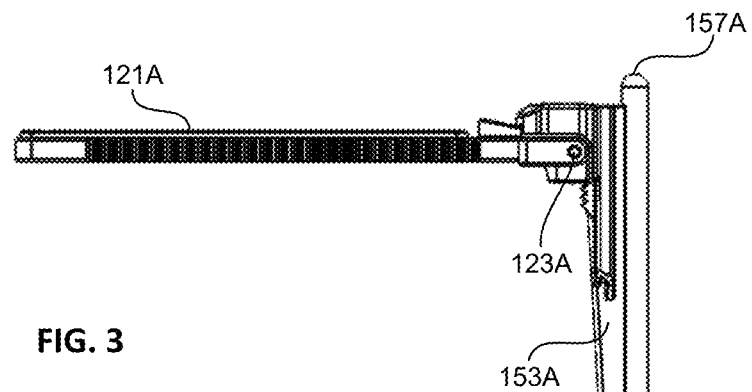
FIG. 3 is a side view of an arm and attached rod of the retractor of FIG. 1.
Figure 4:
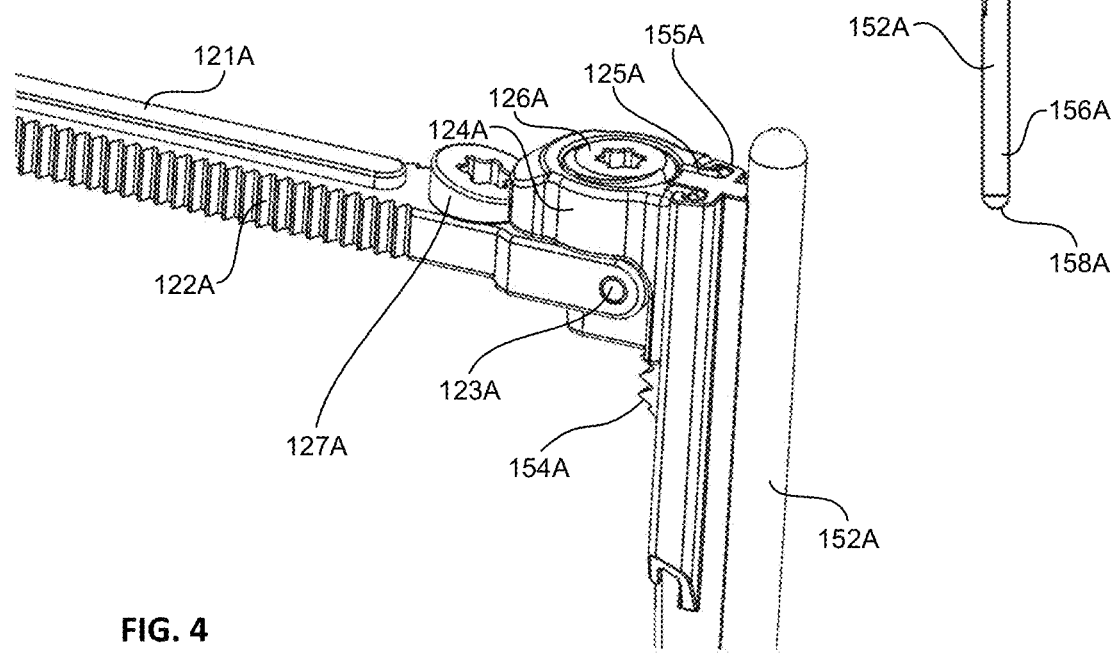
FIG. 4 is a close up perspective view of the rod and attached arm of FIG. 3.

Arm 121A is positioned within rotating support 131A, and in turn, rotating support 131A is secured to frame via post 133A. Adjacent to rotating support 131A and also attached to frame 110 is fixed support 141A, as shown in FIGS. 1 and 2. Arm 121A includes teeth 122A oriented in a direction perpendicular to a length of the arm, and extending over a majority of the arm length, as best shown in FIGS. 2 and 3. These teeth 122A complement corresponding teeth (not shown) on an interior surface of rotating support 131A and thereby allow arm 121A to be moved forward and backward along its length in predetermined increments based on the tooth spacing. Toward a free end of the arm remote from frame 110 is a toeing cam 127A, as shown in FIG. 4, which is positioned under pivoting component 124A. Toeing cam is rotatable to adjust its elevation relative to the arm, such adjustment causing a corresponding rotation in pivoting component 124A, as described in greater detail in the method below. While one end of arm 121A is held in place via rotating support 131A, toward an opposite end are fork shaped extensions that include lateral openings. Pivoting component 124A is disposed in between these forks and a pin 123A is positioned through the openings in both the arm and the pivoting component to secure pivoting component 124A to the main body of arm 121A, as shown in FIG. 4. This form of connection provides a pivoting connection between pivoting component 124A and arm 121A, where the axis of rotation is through an axis of pin 123A.

Pivoting component 124A is U-shaped with arms extending in a manner similar to the forks of arm 121A. Disposed within the arms of pivoting component 124A is a threaded insert 126A, shown in place in FIG. 4 and as a separate element in FIG. 2. At an end of pivoting component 124A facing away from arm 121A are two parallel grooves 125A. These grooves are sized and dimensioned to complement corresponding grooves 155A on rod 151A, described in greater detail below, so that rod 151A remains aligned with arm 121A.

Returning to rotating support 131A, in addition to having an opening therethrough so that arm 121A is positionable therein, rotating support 131A also includes teeth 132A on a lateral side surface, as shown in FIGS. 1 and 2. In position secured to frame 110, teeth 132A face complementary teeth 142A on a side surface of fixed support 141A. Through this configuration, rotating support 131A is rotatable in predetermined increments relative to fixed support 141A, the increments based on a spacing of the teeth on the rotating support. Accordingly, with arm 121A disposed in rotating support 131A, arm 121A is adjustable both longitudinally along its length and rotationally about an axis of rotation of rotating support 131A, both in predetermined increments. Rotating support 131A and fixed support 141A are also structured so that rotating support 131A may be disengaged from fixed support 141A. For example, fixed support 141A may be actuated to disengage rotating support 131A. Because rod 151A is secured to arm 121A, rod 151A moves in conjunction with arm 121A. As will be described in greater detail below, this is advantageous as a position of a rod of the retractor may be tailored to create a desired size and shape of surgical portal. Customization of an opening size is further promoted due to each arm being independently adjustable relative to the others. It is important to note as well, however, that the retractor is also adjustable through simultaneous adjustment of two or more arms up to and including each and every arm.

Turning now to rod 151A secured to arm 121A, a connection therebetween is shown in FIG. 4. Rod 151A includes a portal defining portion 152A and an arm engagement portion 153A shaped similarity to a keel type structure, as shown in FIG. 3. Portal defining portion 152A includes a cylindrical surface 156A extending from a first end 157A near arm 121A to a second end 158A remote from the arm. As depicted, portal defining portion 152A includes a constant cross section over its length with dome shaped tips at both ends (FIG. 3). In addition to the alternate embodiments described below, it is further contemplated that the end tip shapes of portal defining portion may be varied or the cross-section over its length may also be varied. Portal defining portion 152A of rod 151A may be 4 mm in diameter, however other dimensions are also contemplated. Although not shown in FIGS. 1-4, rods 151A-E may be cannulated along their central longitudinal axis with an opening of sufficient size to pass a guidewire therethrough.

Arm engagement portion 153A extends outward on one side of portal defining portion 152A and has a constant width (measured as a distance between the arm and the rod) over a top segment of rod 151A near arm 121A. Moving away from arm 121A, arm engagement portion 153A tapers and terminates on cylindrical surface 156A. In this manner, a length of arm engagement portion 153A is less than that of portal defining portion 152A. Over the constant depth segment of arm engagement portion 153A are grooves 155A shaped and sized to engage with grooves 125A of arm 121A, as noted above (see FIG. 4). Grooves 155A are positioned away from portal defining portion 152A so that no structure obstructs engagement between rod 151A and arm 121A. Also positioned away from portal defining portion 152A are teeth 154A, oriented perpendicular to a length of rod 151A and facing pivoting component 124A. Teeth 154A extend over a segment of arm engagement portion 153A closest to arm 121A and are sized and spaced to engage with threads on threaded insert 126A. Thus, engagement between rod 151A and arm 121A is achieved through interaction between grooves 155A and 125A, and between teeth 154A and threads on threaded insert 126A. As will be described in greater detail below, grooves 155A in conjunction with teeth 154A are designed so that rod 151A is adjustable relative to arm 121A in a direction corresponding to the rod length in predetermined increments. For example, a position of rod 151A may be adjusted into and out of the body. It should be noted that slot 155A extends over a greater length than teeth 154A as shown in FIG. 4. This arrangement is advantageous in that it eases engagement between the rod and arm. In particular, upon first aligning rod with the forks in arm, slots 155A rod may be slid into slots 125A prior to engagement between respective teeth.

In an alternative configuration, engagement features on each of pivoting component 124A and rod 151A are reversed so that the features shown on rod 151B are included on pivoting component 124A and vice versa. In another configuration, each of an arm component (threaded insert and/or pivoting component) and rod include complementary mechanical stops. Such mechanical stops provide an added level of safety to prevent rod from translating beyond a predetermined amount from the arm and into the portal. Mechanical stops may be in the form of complementary protruding surfaces or other interconnecting structures as a matter of design choice.

The above described features provide a retractor with rods that are adjustable in at least four degrees of freedom. Rod 151A may swing in a plane through frame 110 via actuation of rotating support 131A to adjust its connection location with fixed support 141A. Rod 151A is translatable in a direction of the length of arm 121A through adjustment of arm 121A relative to rotating support 131A. Rod 151A is also pivotable relative to arm 121A about the axis through pin 123A. Finally, rod 151A is translatable along its longitudinal axis via interaction of teeth 154A and threads of insert 126A, i.e., rotation of insert 126A causing the rod to translate. As noted above, these structural features and adjustment features of the retractor rods are also applicable to rods 121B-D shown in FIGS. 1 and 2. As seen in FIG. 2, certain arms, such as arms 121B, 121C may be longer or shorter than the others depending on their relative position on retractor frame 110.

For rod 151E, arm 121E is disposed in support 131E, similarly to arms 121A-D, which are respectively disposed in supports 131A-D. However, unlike supports 131A-D, support 131E does not have a fixed support adjacent thereto (see FIGS. 1, 2 and 20). In the embodiment as depicted, employed in a lateral trans-psoas procedure, arm 121E is left fixed in place so that rod 151E remains fixed. Fixation of arm 121E relative to frame 110 may be through fixation mechanisms as known to those of skill in the art. In some variants, and as described below, arm 121E is movable relative to the retractor frame. Optionally, the posterior rod may include a pointed tip on an insertion end remote from the arm so that the rod may be secured and otherwise anchored to a bone for additional stability. This principle may apply to any rod as deemed desirable for a given procedure. Additionally, rod 151E secured to arm 121E is electrically insulated and includes an electrode for neuromonitoring. As will be described in greater detail below, one reason for the distinctive structure of arm 121E and its associated components is that it is well suited for a lateral trans-psoas approach. This is because rod 151E is positionable on a posterior side of the patient. In such approaches, rod 151E functions to protect against impingement of nerves located posterior to rod 151E since rod is held in place while rods 151A-D are retracted. Similar principles may be applied in other approaches, although rod 151E may be located elsewhere relative to a body of a patient.

In some variants, arm 121E and its associated supporting structures are translatable within support 131E, without allowing support 131E to rotate about an axis through its body. Arm 121E otherwise may be modified to include features so that rod 151E is pivotable about arm 121E for toeing in and out and so that it is translatable along its axis. In this manner, modified arm 121E may be adjustable in three degrees of freedom. In yet another alternative, frame may include a fixed support near arm 121E and arm 121E may adjust in four degrees of freedom similar to the other rods. Put another way, a retractor may include five rods that are all movable in multiple degrees of freedom. In other alternatives, rod 151E may be constructed without structure for neuromonitoring.

It should be appreciated that the above described specific features of the retractor for holding the rods and controlling movement of the rods may be modified using other components as known in the art. For example, engagement between teeth on adjacent components may be substituted with other complementary surfaces that achieve the same function.

Returning to retractor frame 110, connectors 102, 103 are secured on end portion 112 thereof. Securement between connectors 102, 103 and frame 110 may be through screws, as shown in FIG. 2, or other means known to those of skill in the art. Each connector 102, 103 includes a fork shaped end for engagement to a rigid arm such as those described in U.S. Prov. Pat. App. No. 62/546,780, the disclosure of which is hereby incorporated by reference herein in its entirety, or another support structure. Engagement to the support structure holds the retractor in place relative to the body of the patient.

Figure 19A:
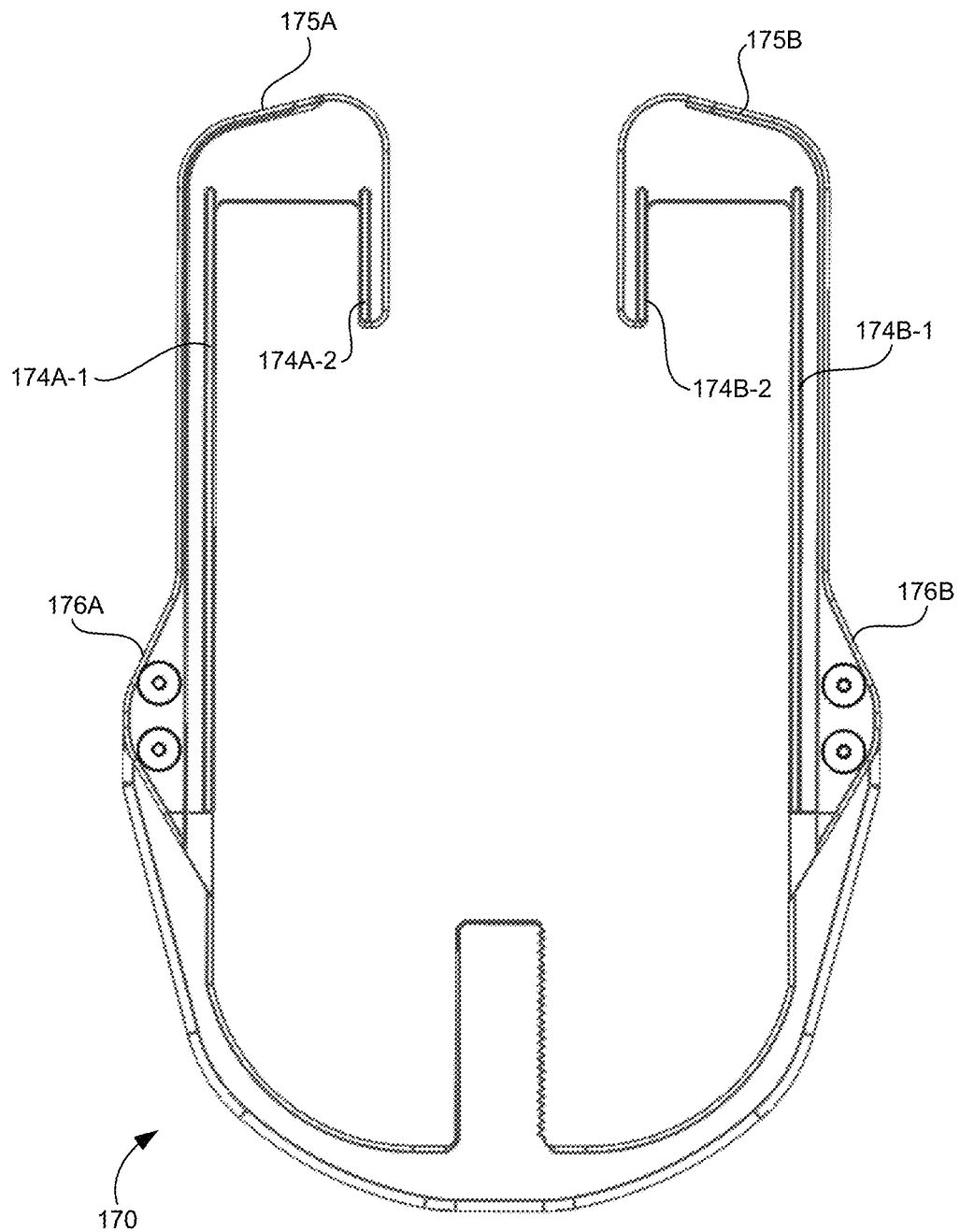
FIG. 19A is a top view of the slide tool included with the retractor of FIG. 1.

Below frame 110 is slide tool 170, shown in FIG. 19A, in part in FIG. 1 and separated into its various subcomponents in FIG. 2. Slide tool 170, in its assembled state, is generally U-shaped with a similar outline to that of frame 110. In this manner, when slide tool 170 is positioned directly underneath frame 110, its outer perimeter is substantially covered by frame 110, as shown in FIG. 1. Slide tool 170 includes two lateral components 171A-B, and an end component 172. Each component includes apertures so that screws may be used to connect the respective components. In particular, apertures 178A, 178B in lateral components 171A-B are aligned with respective apertures 179A, 179B in end component 172 and screws are placed therethrough to secure all three components. Of course, other means may also be used to hold each component together. Alternatively, slide tool 170 may simply be a monolithic structure.

Figure 20:
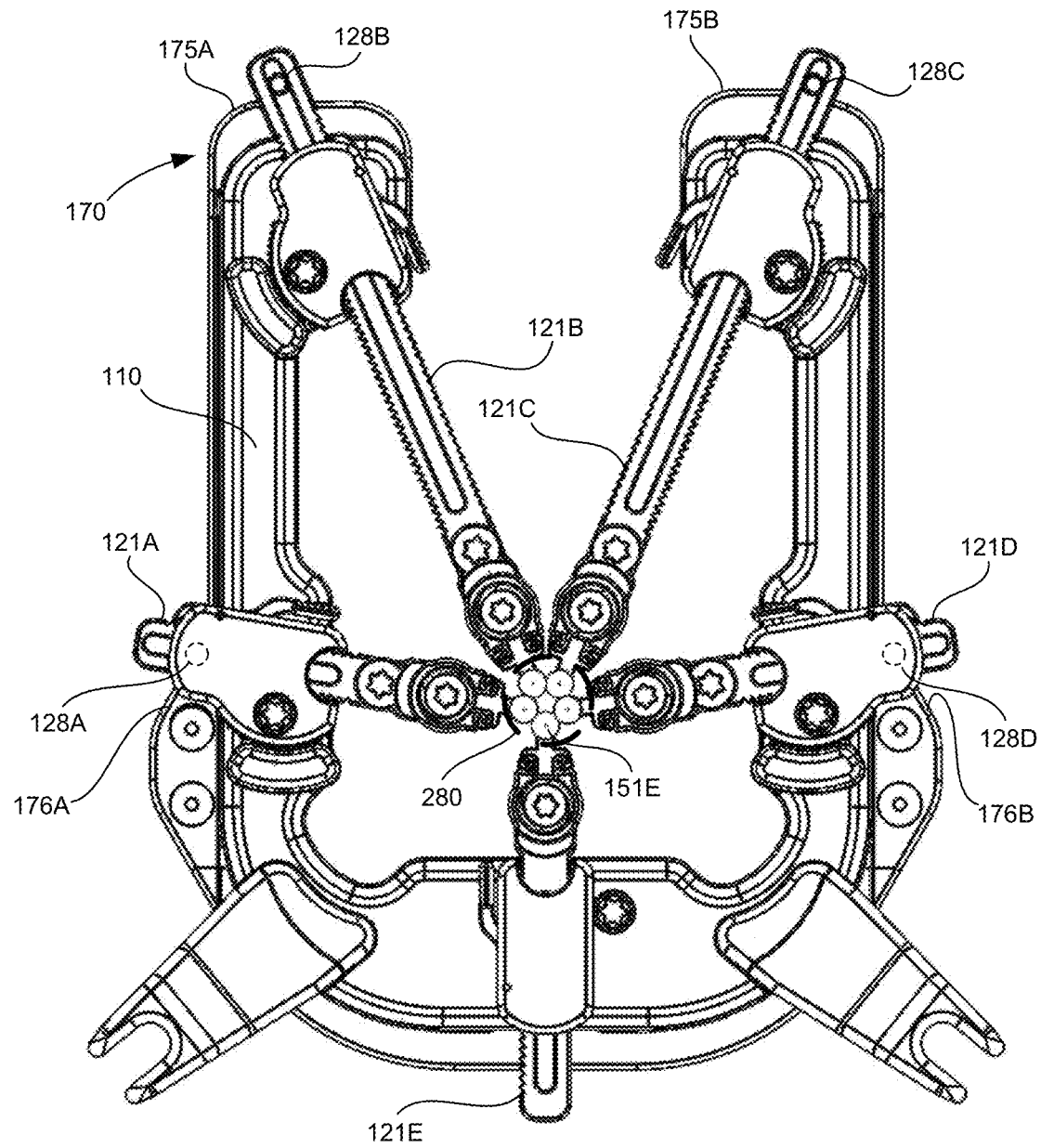
FIGS. 20-22 are top views illustrating various positions of the rods of the retractor shown in FIG. 1.

Each lateral component 171A-B includes a pair of rails, 174A-1, 174A-2 and 174B-1, 174B-2, respectively. Such rails serve a dual function. First, the rails include a recess under their top surface to form a hook to engage with a corresponding feature (not shown) on a bottom surface of frame 110. Second, the rail structure allows slide tool 170 to translate relative to frame 110. Each lateral component 171A-B also includes ramp surfaces located to pass over arms 121A-E when slide tool 170 is translated with respect to frame 110. Ramps include end ramps 175A-B located closest to arms 121B-C, and lateral ramps 176A-B, located closest to arms 121A, 121D. Ramps 176A-B are located on an outside edge of each lateral component and are sloped at about thirty degrees relative to a longitudinal axis of each lateral component, with the ramp angle becoming shallower further away from end ramps. Thus, a lateral edge of lateral component includes a flat portion extending from end ramp 175A or 175B to a lateral ramp 176A or 176B, or ramp portion, which continues toward apertures 178A-B, respectively. End ramps 175A-B are edges generally perpendicular to the longitudinal axis of the lateral components, although include rounded out corners, as shown in FIG. 20, for example. Of course, the angle and other contours of the edge surfaces for the ramps may be varied in any number of ways as a matter of design choice.

On end component 172 is central extension 173, as shown in FIG. 2. Central extension 173 is sized to allow slide tool 170 to translate away from end portion 112 of frame 110 a certain amount. In variants where the central extension larger than shown in FIG. 2, translation of the central extension may be interrupted by rod 151E after a predetermined amount of translation. In other alternative configurations, central extension may be smaller or larger with respect to the slide tool or may be absent altogether. The exact operation of these features is described in greater detail below, although it should be understood that the slide tool 170 operates to provide a rapid opening, i.e., retraction, of rods 151A-E of the retractor, upon translation from a first position shown in FIG. 1 or 20 to a second position shown in FIG. 21 when pulled away from end portion 112 of frame 110. In a variant, the slide tool (not shown) may be modified to include slots through each lateral component. Thus, when assembled, rapid opening pins extending from respective arms on the retractor (e.g., rapid opening pins 128A-D shown in FIGS. 20-21), are positioned within respective slots in the slide tool. Such a slide tool includes the same capability as slide tool 170 for rapid retraction of the retractor rods, but, through the opposite surface within slots of the slide tool, allows for a reverse translation to bring the rods back into a closed position.

Figure 33:
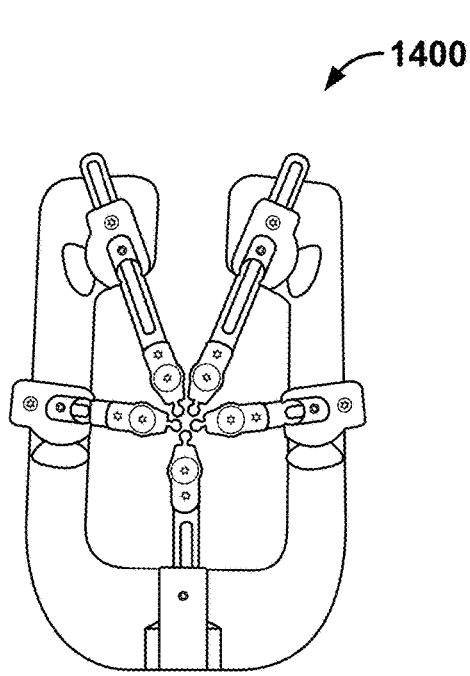
FIGS. 33-34 are top views of a retractor according to one embodiment of the invention in closed and open positions, respectively.
Figure 34:
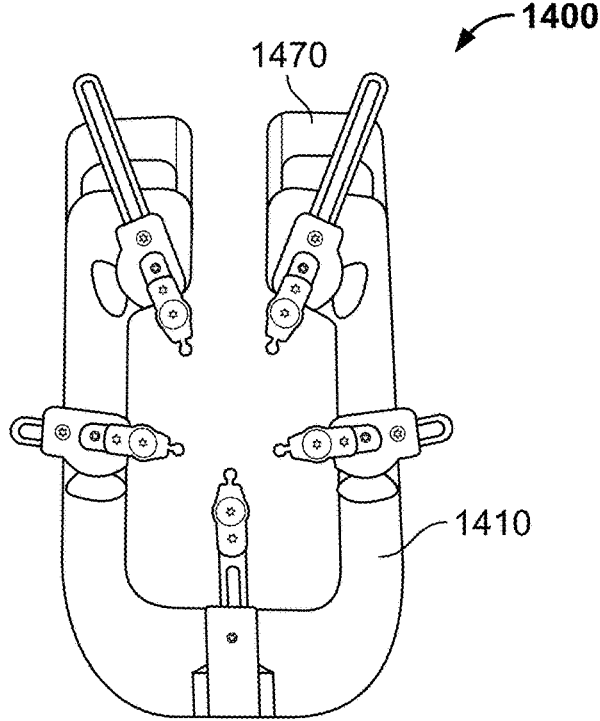
Figure 35:
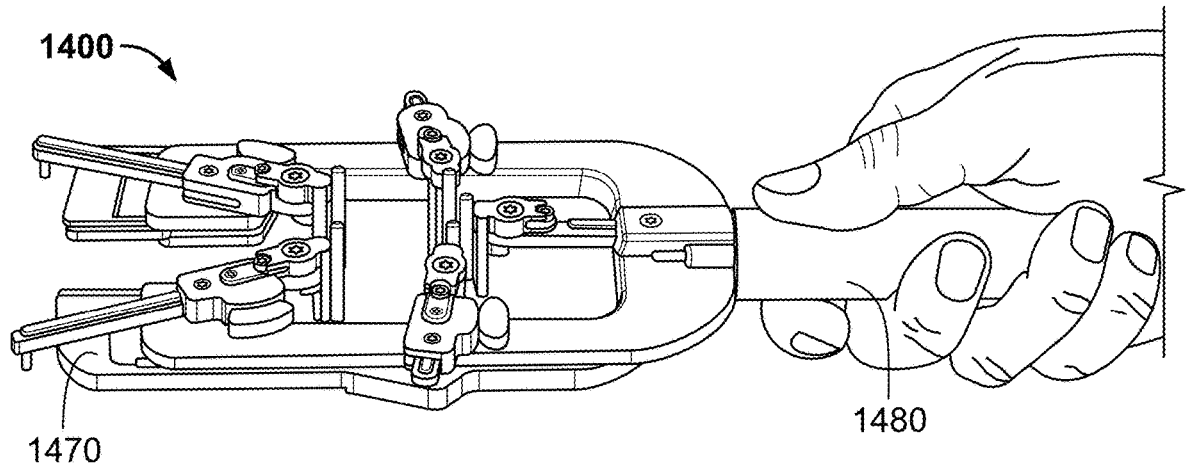
FIG. 35 is an angled view of the retractor of FIG. 33.
Figure 36A:
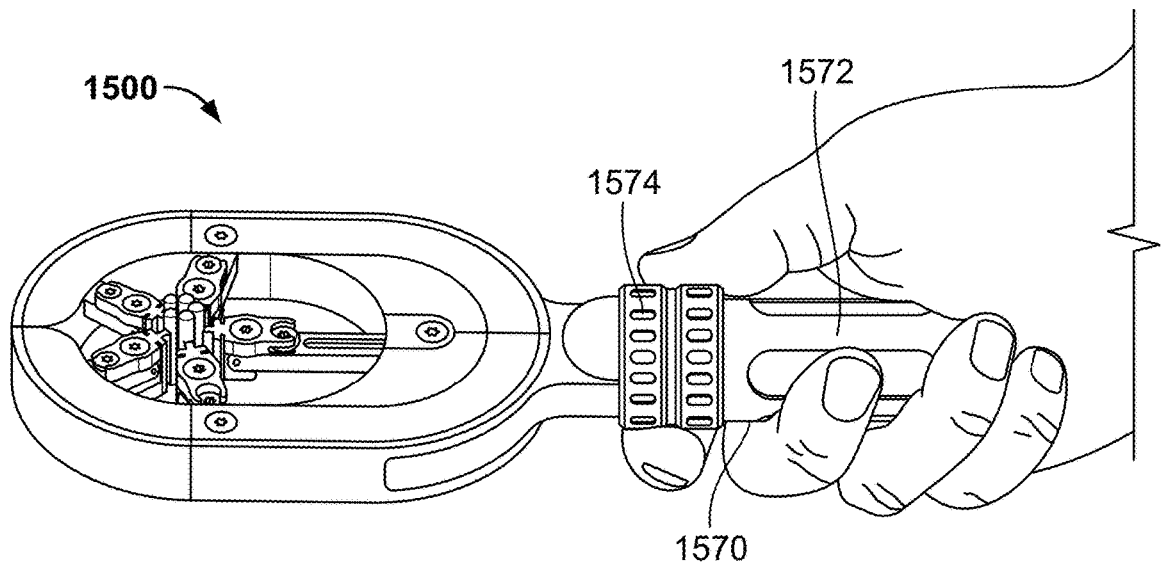
FIGS. 36A-36B are different views of a retractor in a closed position according to one embodiment of the disclosure.
Figure 36B:
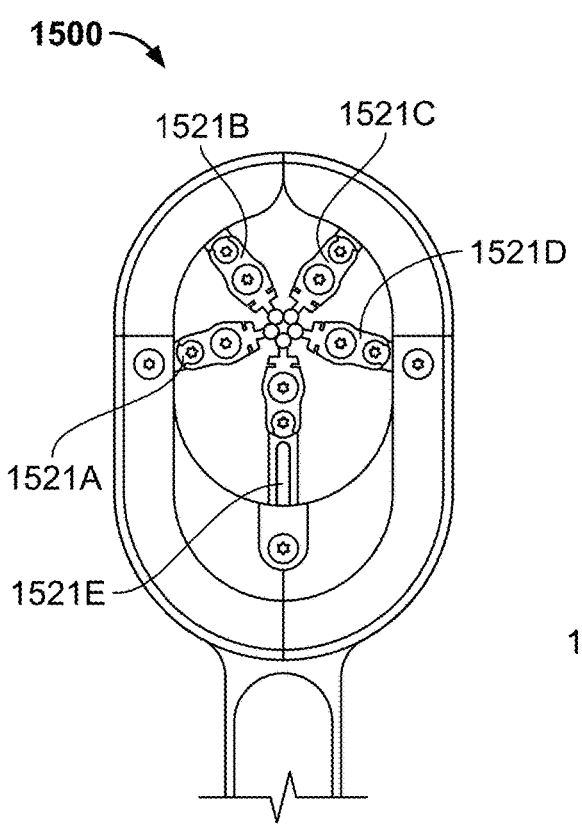

In some embodiments, the retractor of FIG. 1 may be modified to appear as shown in FIGS. 33-35. Retractor 1400 may perform at least all of the rod movements possible with retractor 100 and provides for similar posterior rod adjustment and maximum surgical portal opening size.

Figure 31:
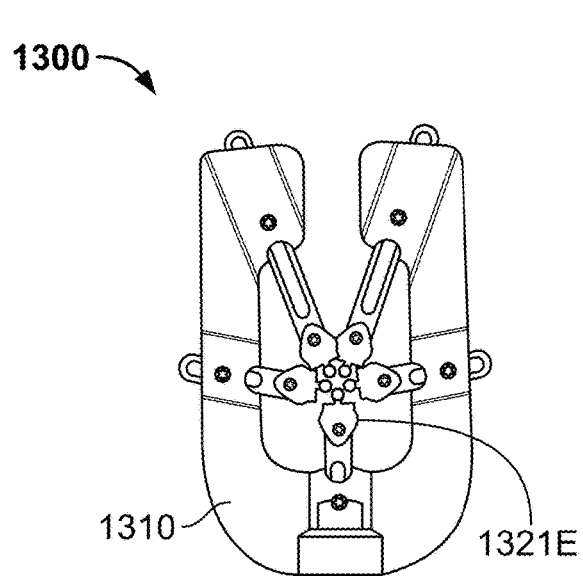
FIGS. 31-32 are top views of a retractor according to one embodiment of the invention in closed and open positions, respectively.
Figure 32:
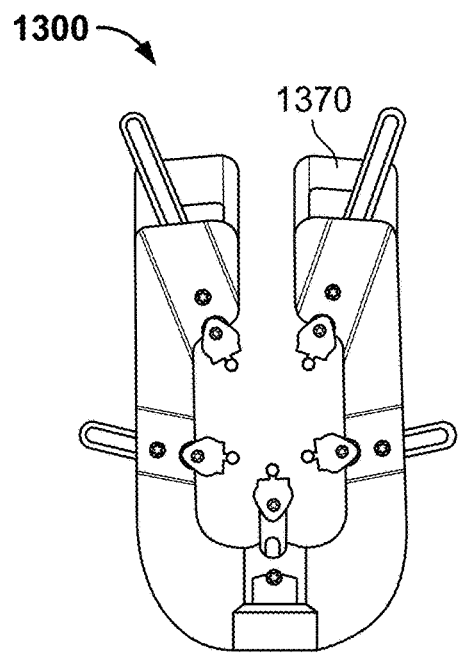

In another embodiment, a retractor 1300 with frame 1310 is more compact than retractor 100 and appears as shown in FIGS. 31-32. In one example, the frame measures 139 mm by 94 mm. In other examples, such dimensions may be larger or smaller. Unlike retractors 100, 1400, retractor 1300 does not include external rotating supports to hold the arms of the retractor. The features of this retractor make possible its smaller size. Retractor 1300 includes a slide tool 1370 for rapid opening, includes arms adapted for toeing of the rods, and also provides for individual rod retraction via arm translation relative to the frame. Arm 1321E may be translated up to 10 mm. Although retractor 1300 is compact, rods may still be retracted sufficiently to create a surgical portal measuring 20 mm by 30 mm. In yet another variant (not shown), a retractor may be even smaller than retractor 1300. For example, such a retractor may have a frame measuring 132 mm by 88 mm in dimensions and include arms so that a surgical portal up to 14 mm by 24 mm in dimensions may be created through retraction. Such a retractor includes a slide tool adapted for rapid opening of the rods, arms adapted for toeing of the rods, and translation of a posterior arm/rod by an amount up to 10 mm. Of course, the frame may also have dimensions in between the above examples or even smaller than the lower end of the range.

Figure 45:
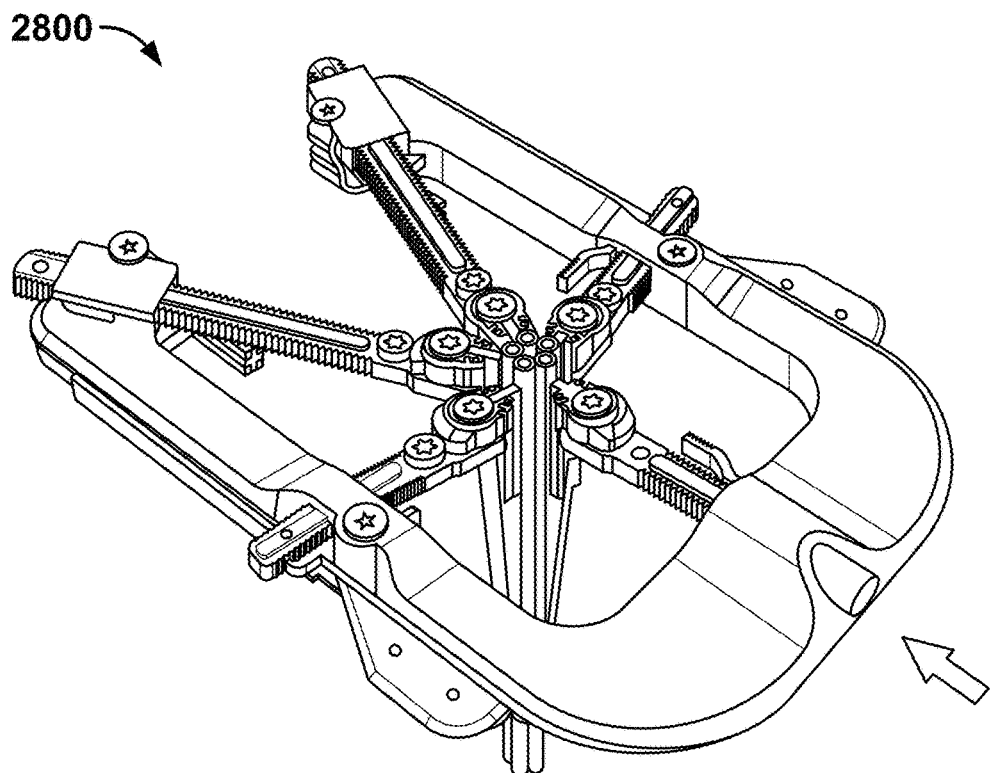
FIG. 45 is a perspective view of a retractor according to one embodiment of the disclosure.
Figure 46:
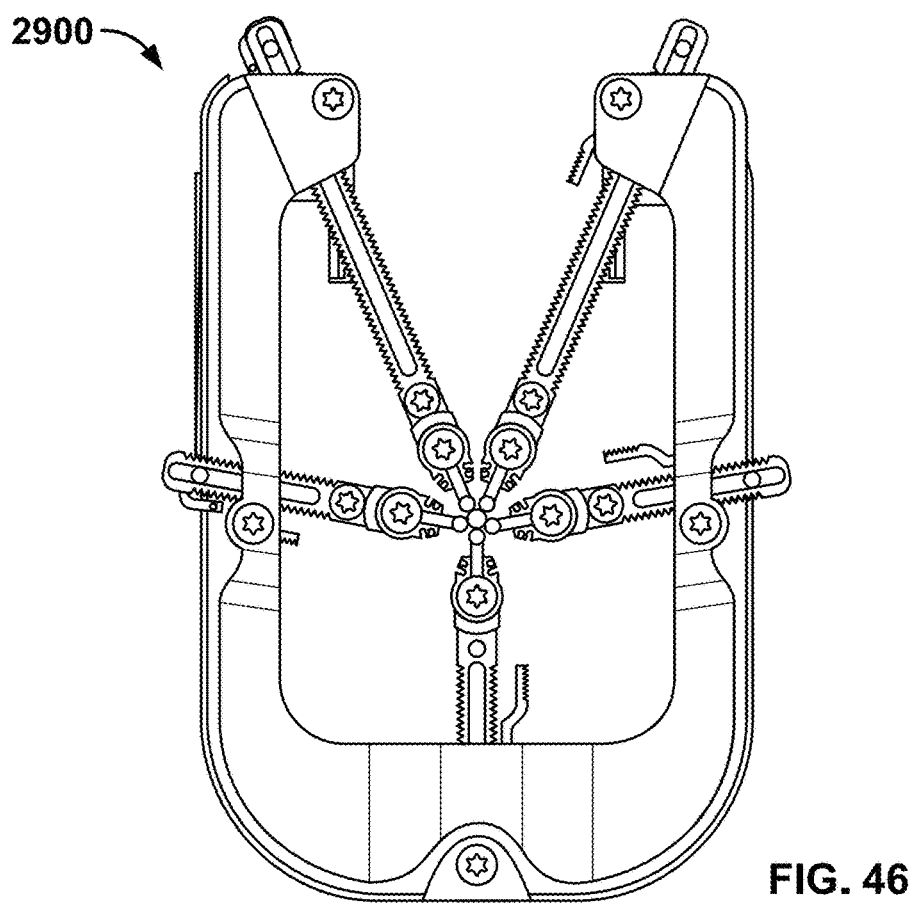
FIG. 46 is a top view of a retractor according to one embodiment of the disclosure.

In other embodiments, a retractor may have a frame and arms as shown for retractors 2800, 2900 depicted in FIGS. 45 and 46.

Figure 5:
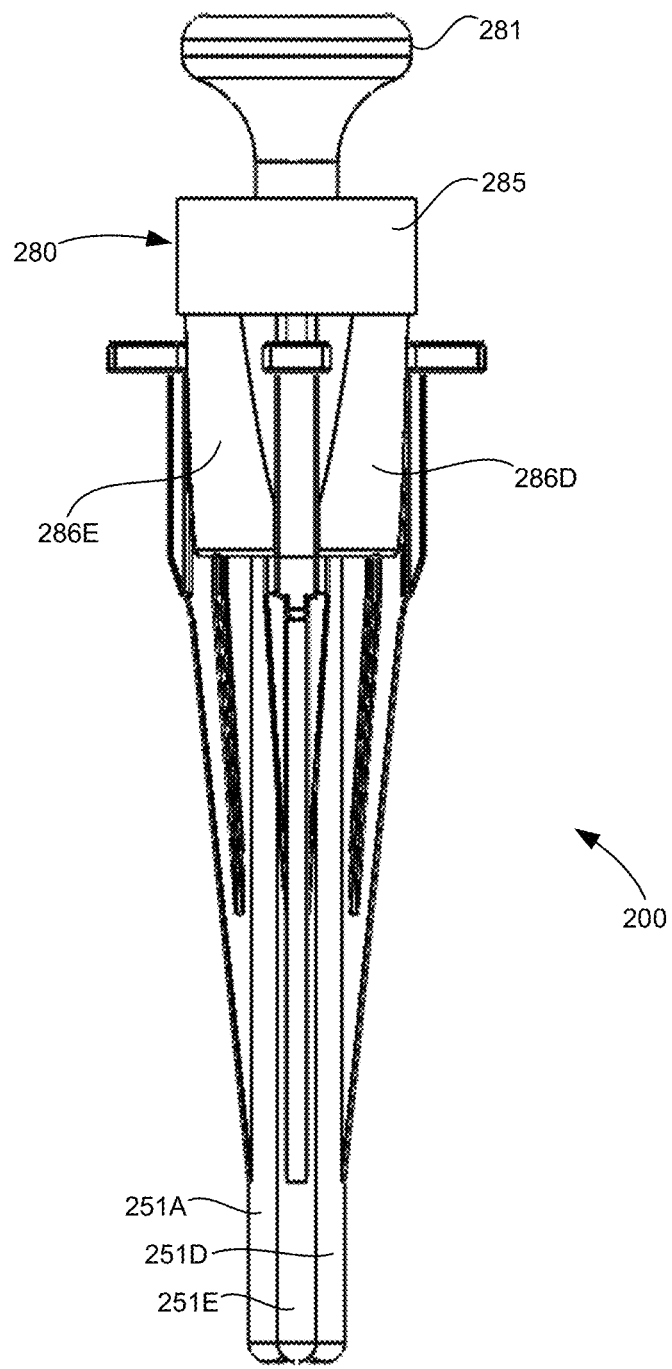
FIG. 5 is a side view of retractor rods with a squid cap according to one embodiment of the disclosure.
Figure 6:
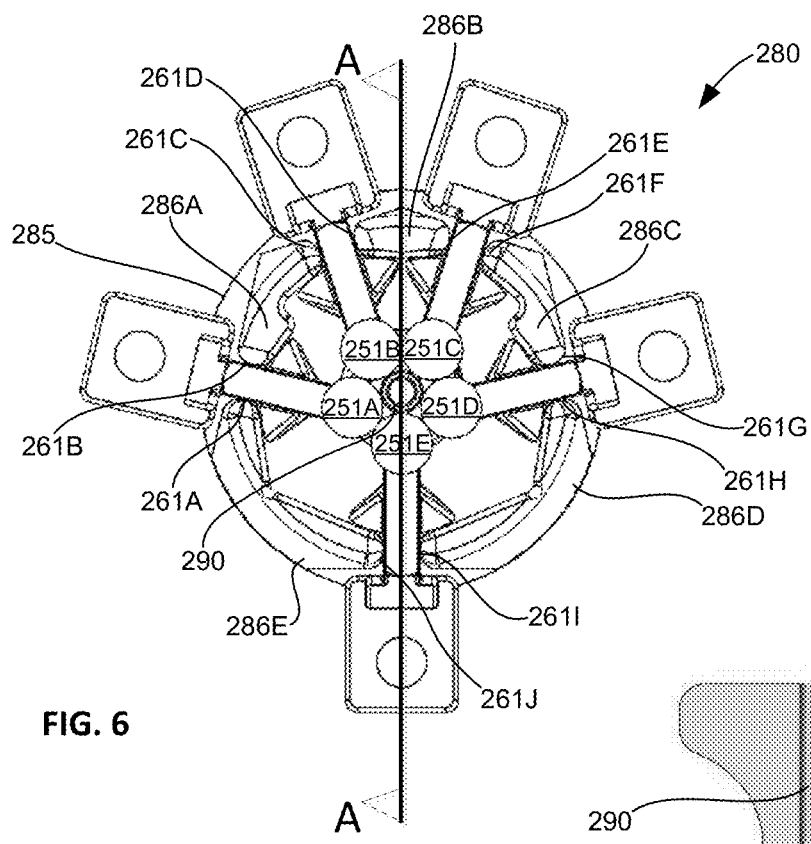
FIG. 6 is a bottom view of the system of FIG. 5.
Figure 7:
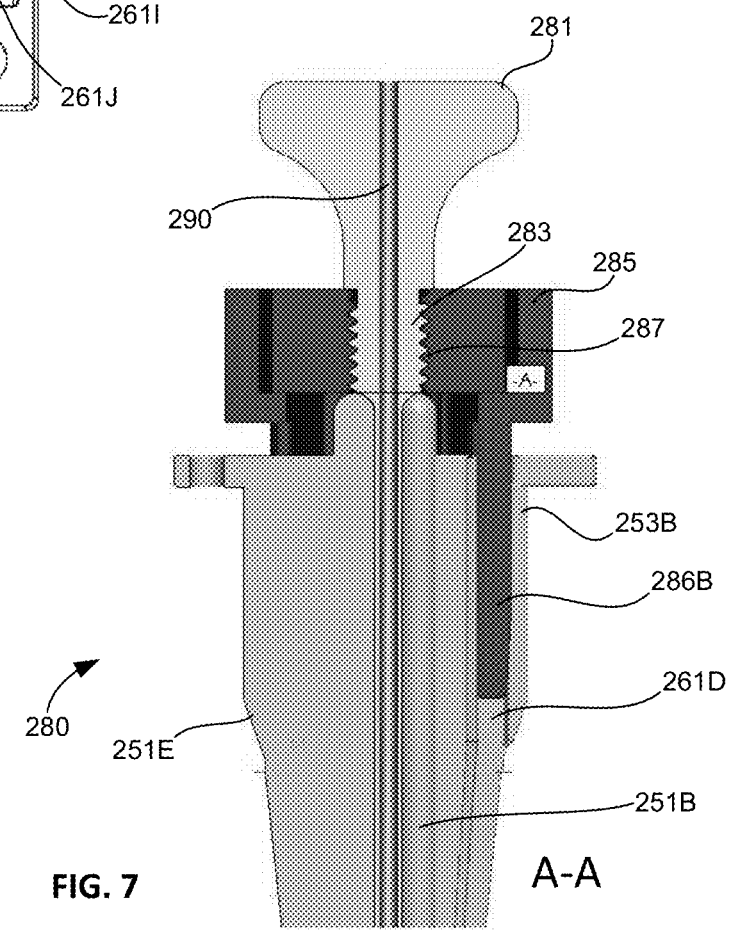
FIG. 7 is a close up cross sectional view of the system of FIG. 5 taken along line A-A of FIG. 6.

In another embodiment, a retractor system includes a retractor and a squid cap 280. The rods of the retractor with squid cap 280 disposed thereon are shown in FIGS. 5-7 while squid cap 280 is illustrated individually in FIG. 8. Squid cap 280 includes a handle 281, a central body 285, and extensions 286A-E extending from the central body and defining a cavity therebetween.

Figure 8:
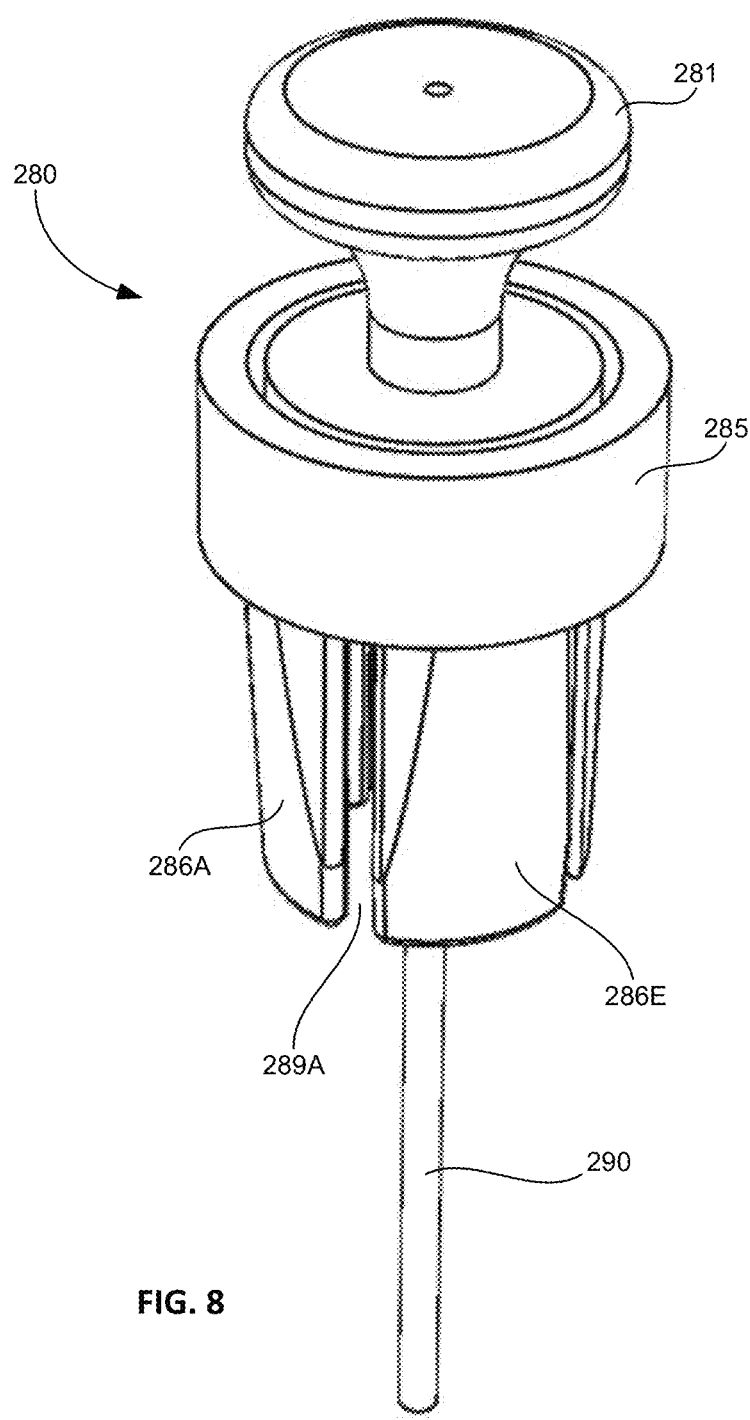
FIG. 8 is a perspective view of the squid cap of the system shown in FIG. 5.

Handle 281 of squid cap 280 is mushroom shaped to aid in gripping by a user, though other shapes and surface features are also contemplated as known to those of skill in the art. Extending from handle is a threaded handle extension 283 engageable with corresponding internal threads 287 inside central body 285, as shown in FIG. 7. As depicted in FIG. 7, handle 281 is a separate element from central body 285, however, it is contemplated that squid cap 280 may be a monolithic structure. Handle 281 also includes a central cannulation sized for placement of a probe 290 therein, as shown in FIGS. 7 and 8. Probe 290 serves to keep retractor in line with guidewire during advancement and withdrawal from a target site in a patient and also serves to keep the rods from floating into a center void in between the rods. In an alternative arrangement, the squid cap may exclude probe 290. Turning to extensions 286A-E, a combined cross section of extensions 286A-E defines an opening therebetween as shown in FIGS. 6 and 8 that is large enough for enclosure of each rod 251A-E.

As depicted, rods 251A-E include side grooves 261A-J sized and positioned for nesting of extensions 286A-E therein. For example, extension 286B is advanced in between grooves 261D of rod 251B and groove 261E of rod 251C, as shown in FIGS. 6 and 7. Squid cap 280 is secured over rods so that each rod 251A-E abuts one another and probe 290 is disposed in between the rods, as shown in FIG. 6. When squid cap 280 is positioned to surround the rods, a portion of each arm engagement portion 253A-F passes through respective slots 289A-E and out of an envelope of squid cap 280, as shown in FIGS. 5-7. This allows squid cap 280 to hold rods 251A-E in position with respect to one another while the retractor arms remain engaged to the rods. Although depicted as engaged with rods 251A-E, the squid cap may be modified and otherwise adapted for engagement with rods 151A-E or other rods having a keel type arm engagement structure. In some examples, the squid cap is made of a flexible material such as a polymer. A polymer squid cap is advantageous in that it is radiolucent and has a flexible material property. This leaves room for rods to adjust within the squid cap. If the polymer is formed to have a diameter somewhat smaller than an outer envelope of the combined rods, the squid cap may be expanded to bring it over the combined rods and once over, close against the rods providing an additional means of holding the rods together. The squid cap may also be customized for an angulation of the rods within the squid cap. For instance, the combined rods may form a shape coning inward from a tail end, defining a larger envelope at the tail end that is held by the squid cap.

Figure 9:
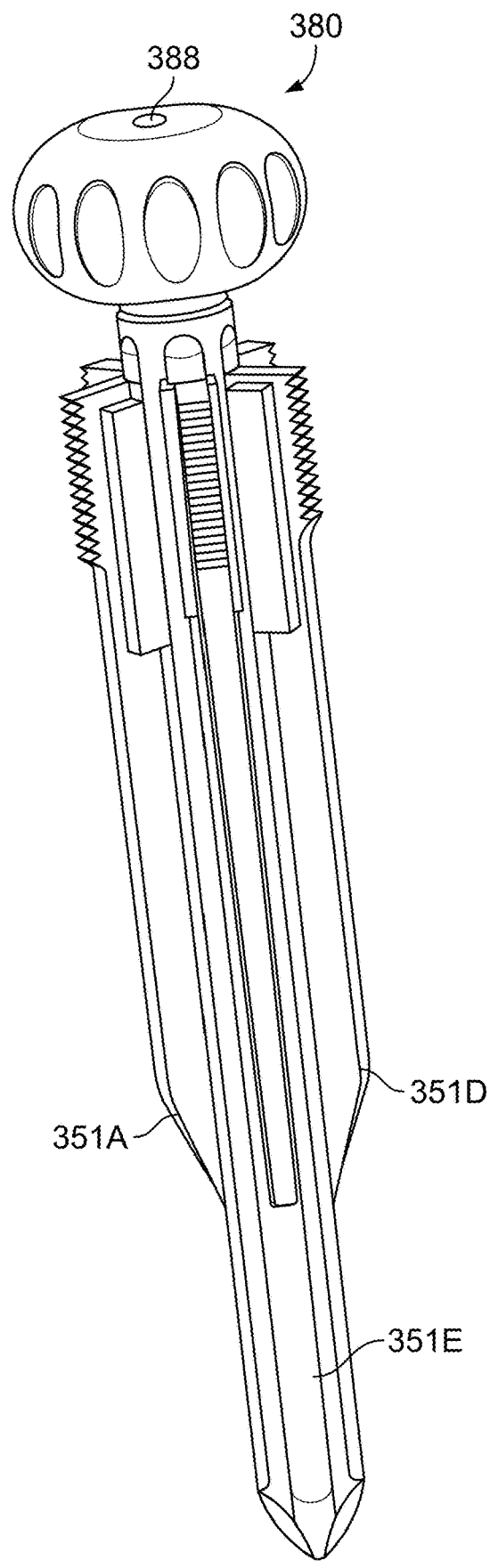
FIG. 9 is a perspective view of a central core element according to one embodiment of the disclosure with rods disposed thereon.
Figure 10:
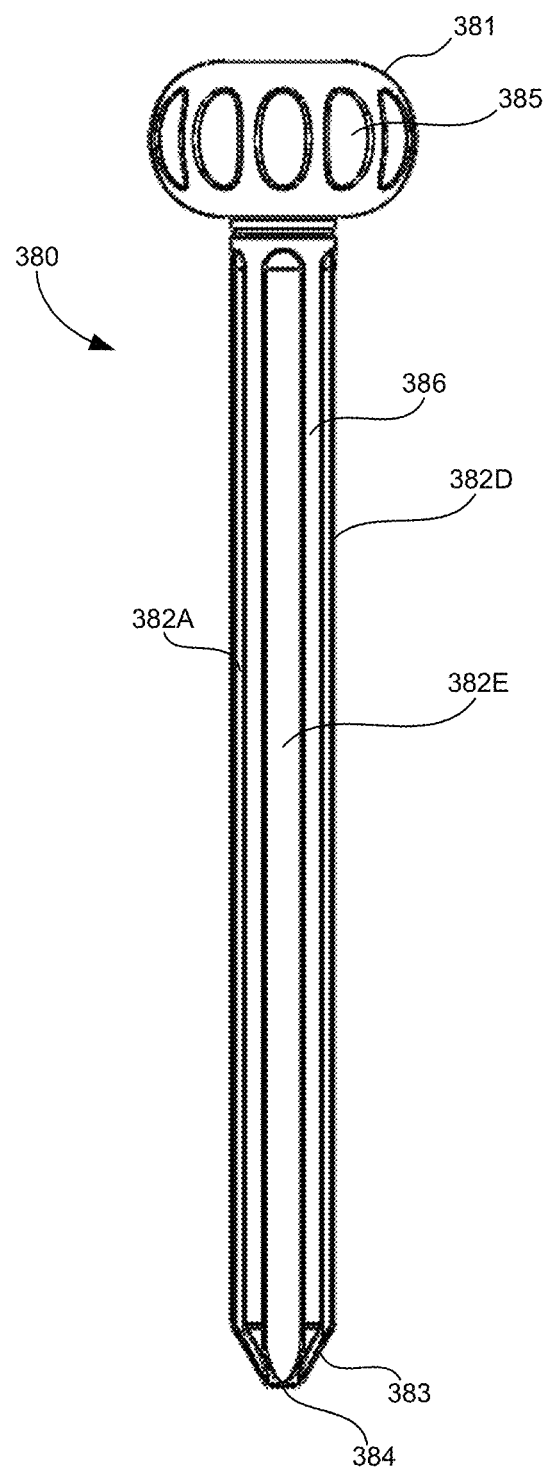
FIG. 10 is a side view of the central core element of FIG. 9.
Figure 11:
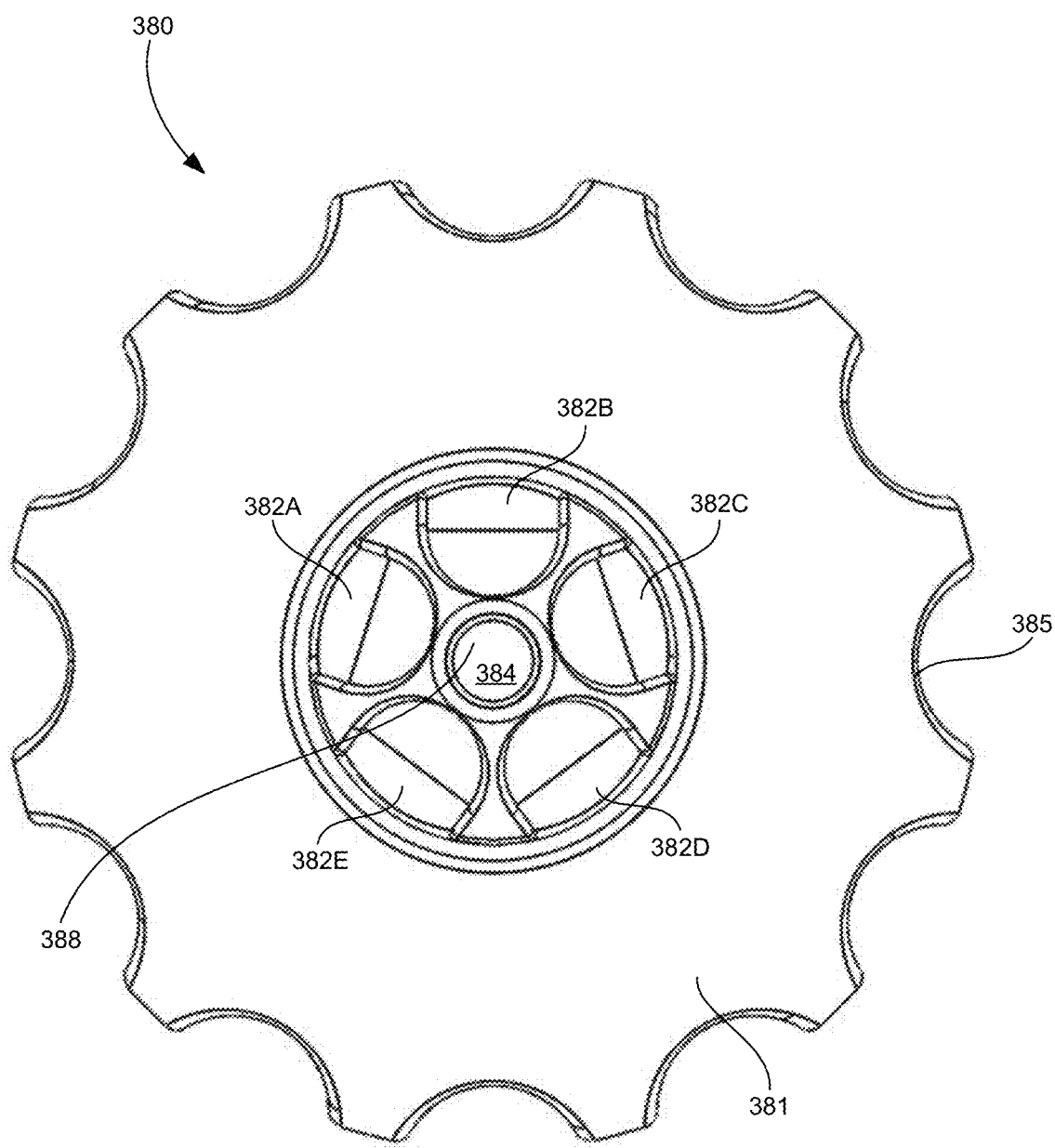
FIG. 11 is a bottom view of the central core element of FIG. 9.

In another embodiment, a retractor system includes a retractor and a central core element as shown in FIGS. 9-11. In FIG. 9, central core 380 is shown with retractor rods thereon, the remainder of the retractor not shown to provide improved visualization of the interaction between central core 380 and rods 351A-E. Central core 380 is an advantageous complement to the retractor in that it provides an initial predetermined spacing between rods 351A-E prior to insertion of the rods into the patient, while the spacing is small enough so that the rods are still considered to be in the closed position. In this manner, a surgical portal is defined upon initial insertion of the rods, thereby reducing the effort necessary to increase the portal to a desired size when compared to insertion without a central core.

As shown in FIG. 10, central core 380 includes a handle 381 with grips 385 at a first end corresponding to the trailing end of the retractor insertion. Handle 381 is made of a material to reduce interference that may otherwise occur when x-rays are taken. The body of central core 380 extends from handle 381 and includes a cylindrical surface 386 with equally spaced longitudinal recesses 382A-E carved from the cylindrical surface and having a concave cross-section, best shown in FIG. 11. These recesses have a radius of curvature matching that of the retractor rods so that when rods are nested therein, as shown in FIG. 9, minimal space remains between the rods and the recesses. As depicted, a length of central core 380 is longer than rods 351A-E of the retractor, as shown in FIG. 9. This ensures tissue penetration is through a tapered tip 383 located toward a leading end of central core 380. The tapered tip is shaped so that resistance due to tissue is reduced when central core 380 is inserted into the patient. As depicted, central core 380 is cannulated 388 through its length on its central longitudinal axis. To accommodate an opening for cannulation 388, tapered tip 383 terminates at insertion end face 384, distal to handle 381. Cannulation 388 is of a sufficient diameter so that a guidewire is disposable therein. Although grooves 382A-E are shown with a dimension creating a loose fit with rods 351A-E nested therein, it is contemplated as an alternative that such grooves can be defined by a surface curving inward at an outer circumference of the core, thereby creating a tight fit between the central core element 380 and rods secured therein, similar to that shown in the core of the squid core combination structure shown in FIG. 18B.

Figure 12:
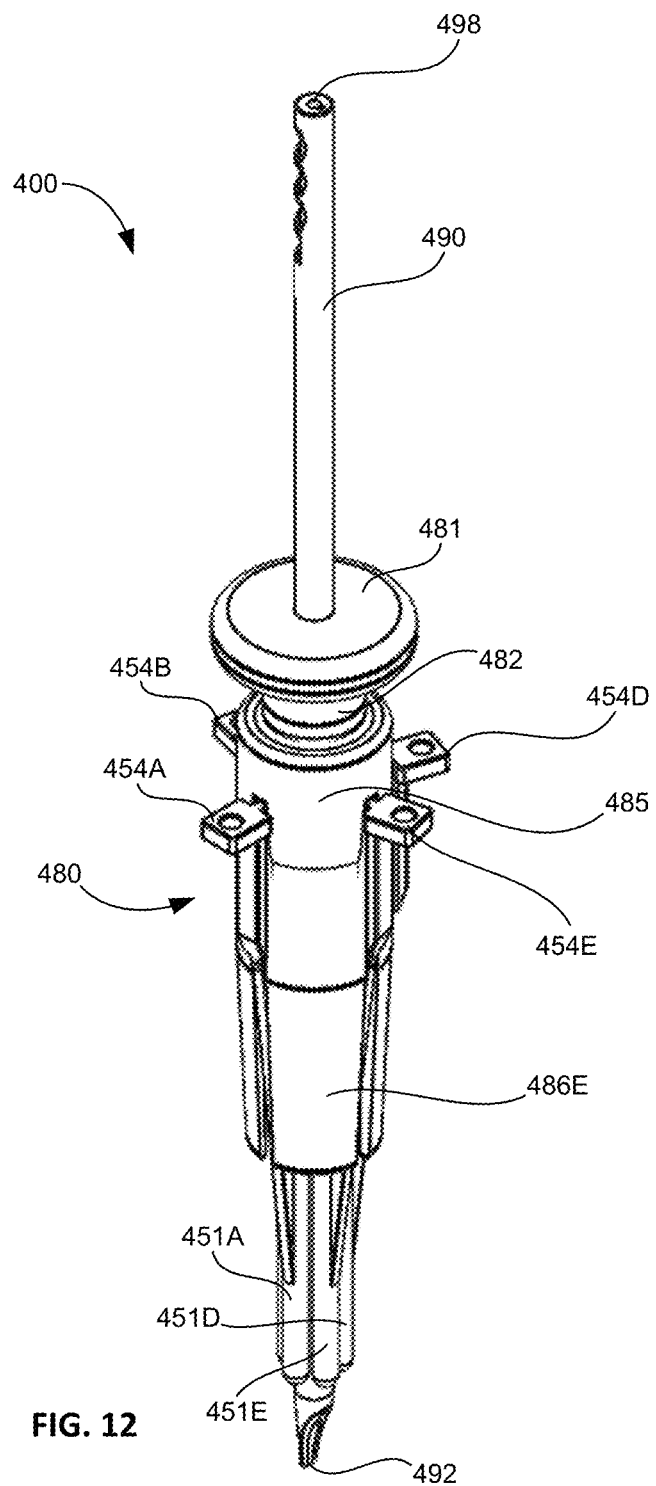
FIG. 12 is a perspective view of a squid cap and rod system according to one embodiment of the disclosure.
Figure 13:
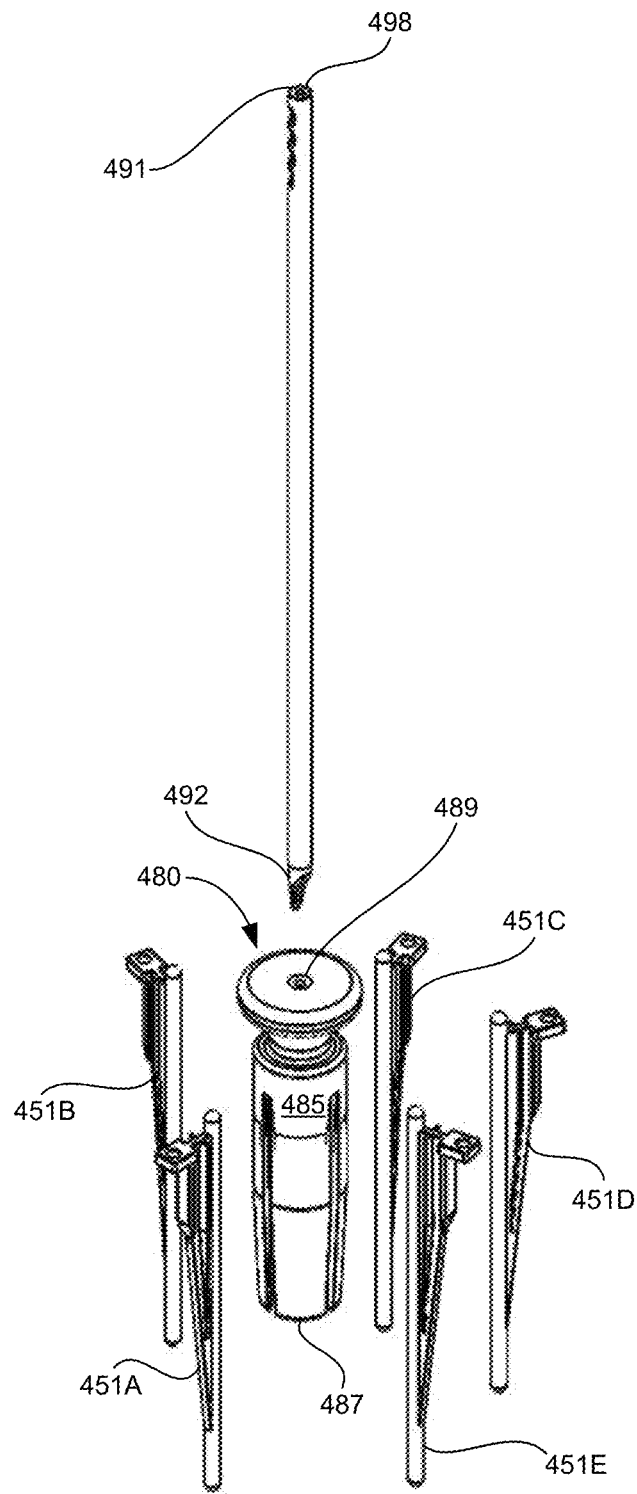
FIG. 13 is an exploded view of the system of FIG. 12.
Figure 14:
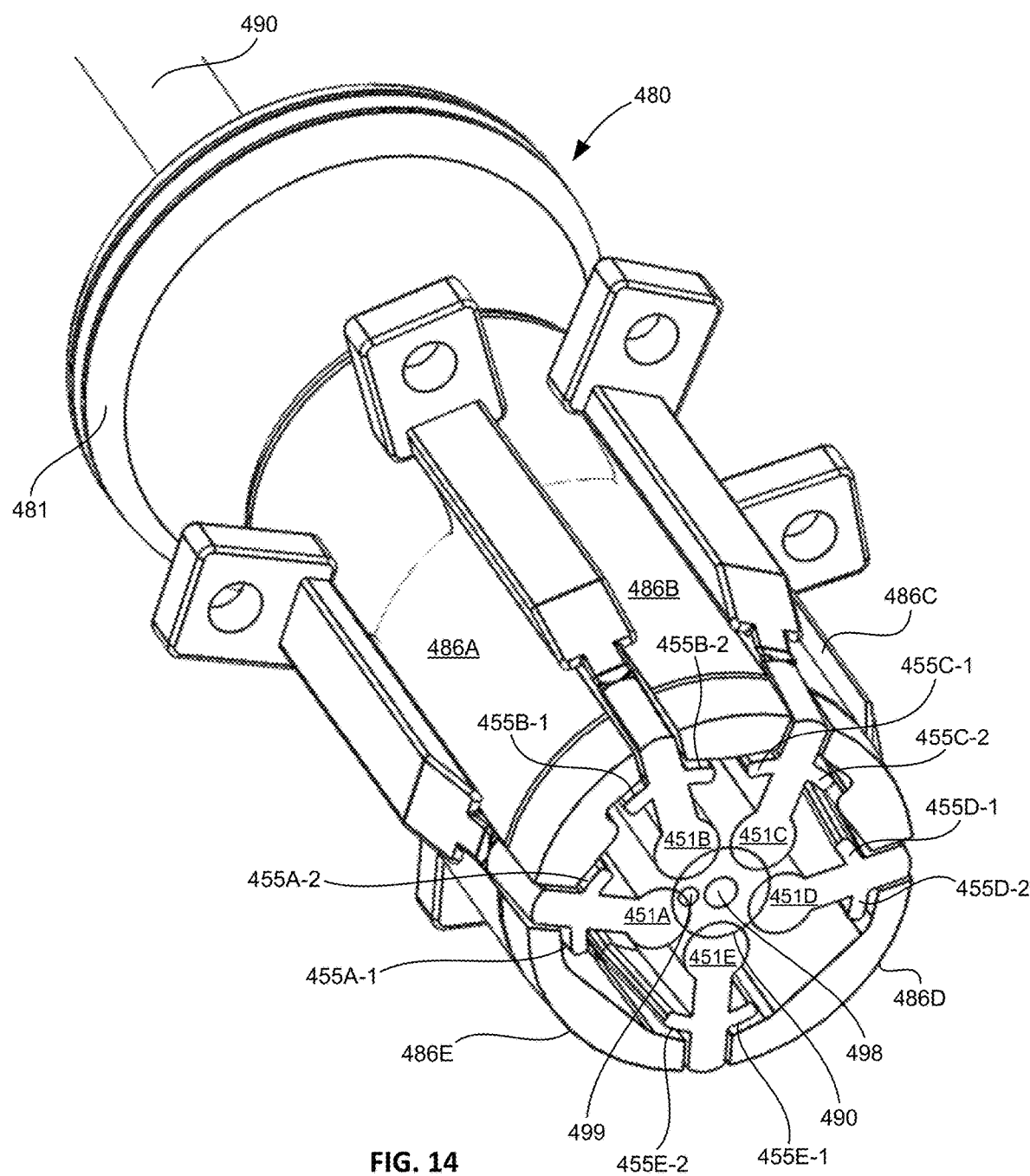
FIG. 14 is an angled sectional view of the system of FIG. 12.

In yet another embodiment, a retractor system includes a retractor, a squid cap 480 and a probe 490, as shown in FIGS. 12-14. Probe 490 is positioned in between the five rods of the retractor while squid cap 480 surrounds each of the portal defining, i.e., cylindrical portions of the rods to hold them in position with respect to each other. In a fully assembled state, the arms of the retractor are secured to each rod at interfaces 454A-E, partially shown in FIG. 12. Unless otherwise noted, like reference numerals refer to like elements for features of rods 451A-E.

As shown in FIG. 13 for example, probe 490 is cylindrical in shape and includes a trailing end 491 and a leading end in the form of a pointed tip 492. As depicted, probe 490 is cannulated 498 with a size of the cannulation sufficient for placement of a guidewire therethrough. In a variant, probe may include a second cannulation 499, such as is shown in FIG. 14, so that the guidewire may be repositioned at a predetermined offset from central cannula 498. Alternatively, the retractor system may include a k-wire in place of a probe.

Squid cap 480 includes a handle in the form of a knob 481, a neck 482, a main body 485 with a cylindrical shape, and slightly tapered extensions 486A-E extending from main body 485. Knob 481 is shaped to render advancement of squid cap 480 over rods 451A-E easier when handled by a user. As with other squid caps described herein, extensions are separated by longitudinal slots extending from main body 485 to an open end 487 of squid cap 480. As seen in FIG. 14, each extension has a thickness so that a cavity within a combined inner surface of the extensions is sufficiently large for portal defining portions of rods 451A-E to fit therein, along with lateral extensions 455A-1, 455A-2, 455B-1, 455B-2, 455C-1, 455C-2, 455D-1, 455D-2, 455E-1, 455E-2 which are sized to abut inner surfaces of extensions 486A-E and are best shown in FIG. 14. This keeps rods 451A-E from retreating from their closed position or otherwise from sliding out from within squid cap 480. Also shown in FIG. 14, rods 451A-E fit within squid cap 480 even when probe 490 is disposed in between the rods. Again, as with other squid cap structures, squid cap 480 retains rods 451A-E in place in a closed position while squid cap 480 is held over the rods. Squid cap also includes an opening 489 in knob 481 sized for disposal of probe 490 therein, as shown in FIGS. 12 and 13. Of course, where a k-wire is included, a size of opening 489 may be customized as needed to suit the size of the k-wire.

Figure 15:
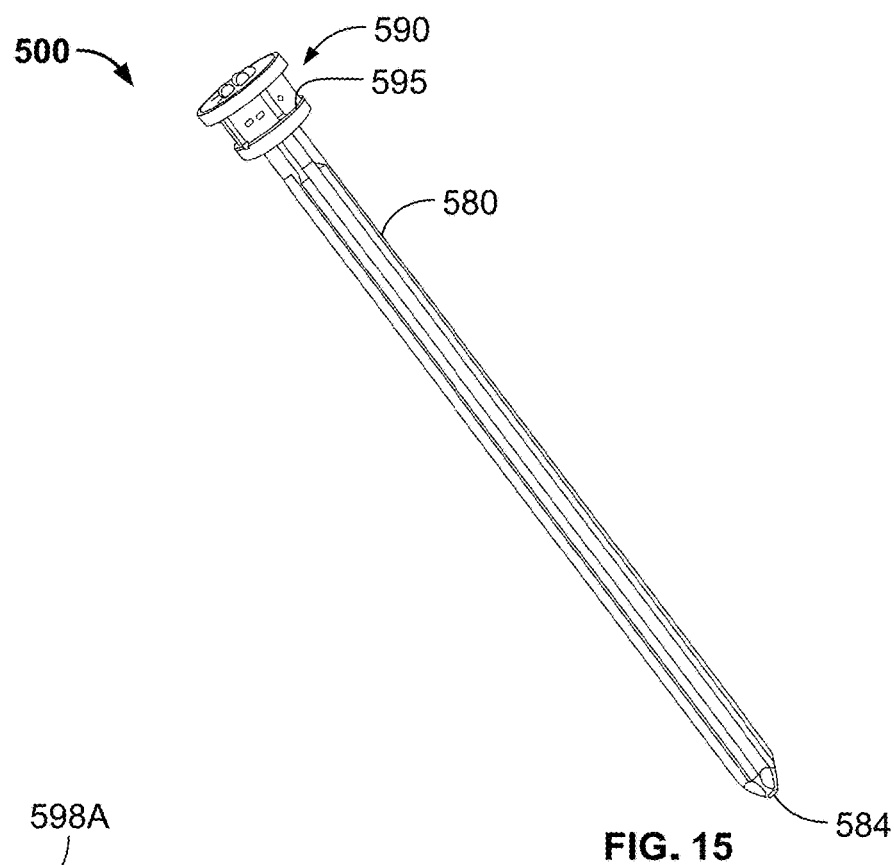
FIG. 15 is a perspective view of a squid core combination system according to one embodiment of the disclosure.
Figure 16:
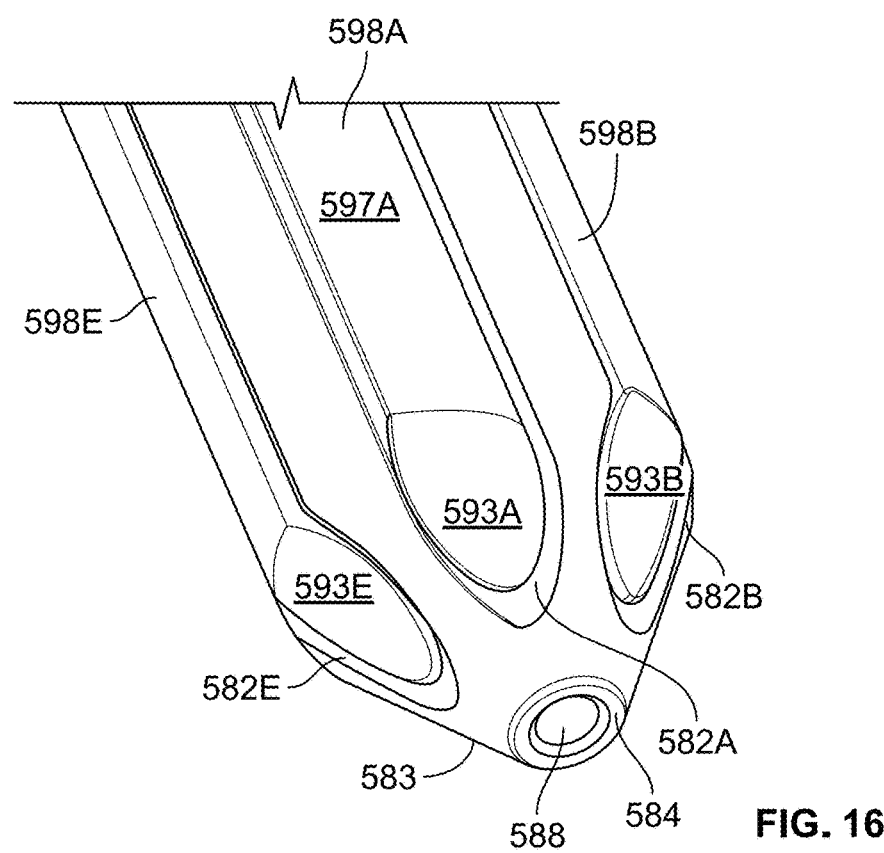
FIG. 16 is a close up view of an insertion end tip of the system of FIG. 15.

In yet another embodiment, a retractor system includes a retractor (not shown) and a squid core combination structure 500 as shown in FIGS. 15-16. The combination structure includes a squid enclosure 590 with squid rods 598A-E extending therefrom, and a central core 580.

Central core 580 includes a generally cylindrical surface with longitudinal grooves 582A-E located at intervals around its circumference. Grooves 582A-E have a concave outer surface and are sized for disposal of squid rods 598A-E or rods 551A-E therein. (See FIGS. 17 and 18A, respectively). Passing through a central longitudinal axis of central core 580 is a cannulation 588 sized so that central core 580 may be placed over a guidewire. Toward a leading end of central core 580 is a conical tip 583, best shown in FIG. 16, which is partially truncated at an insertion end surface 584 surrounding cannulation 588. As with other embodiments of the disclosure, the tapering tip of central core 580 reduces tissue resistance when squid core combination structure 500 is inserted into a patient. At a trailing end opposite end 584 is an engagement mechanism (not shown) for engagement between central core 580 and squid enclosure 590. Alternatively, central core 580 may be structured without a trailing engagement element and squid enclosure 590 and central core 580 may be held together by hand or with an external device.

Figure 17:
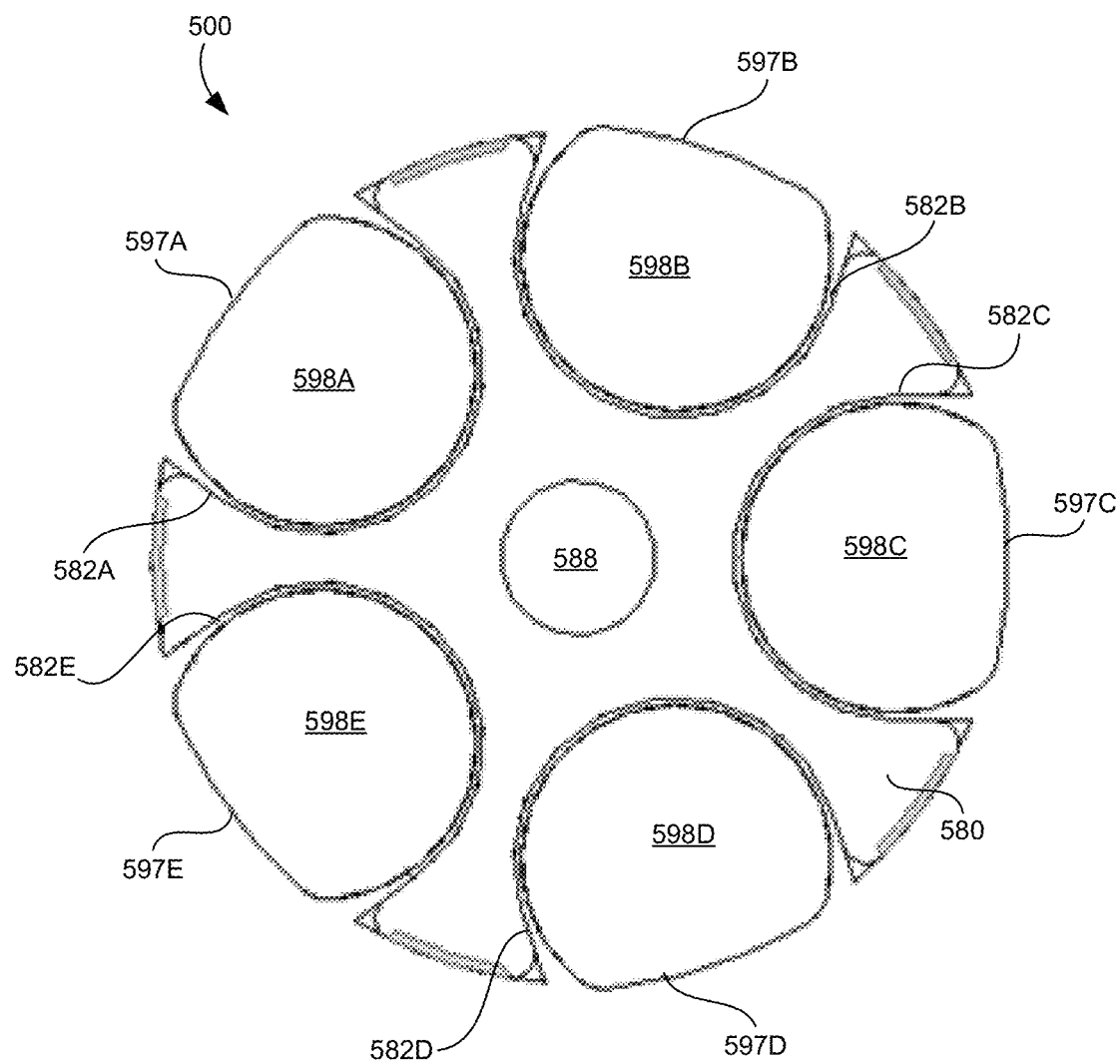
FIG. 17 is a sectional view of a central core and squid rods of the system of FIG. 15.
Figure 18A:
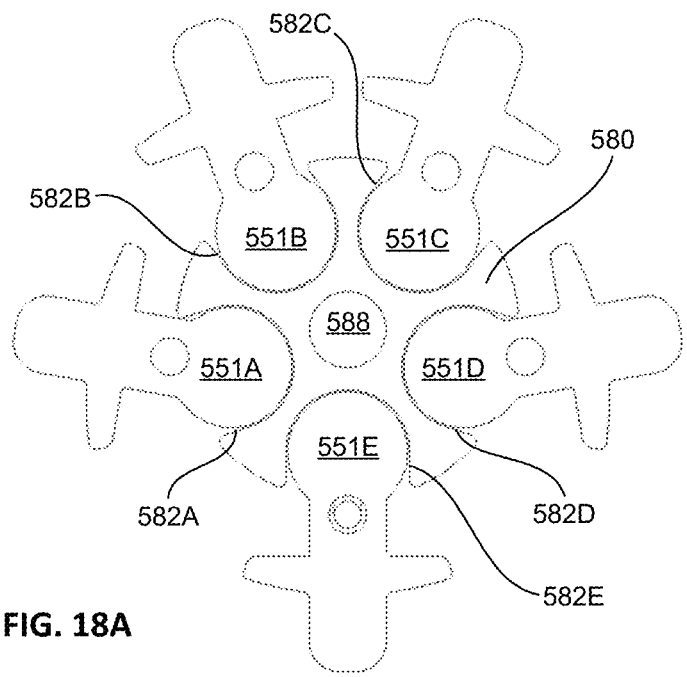
FIGS. 18A-B are sectional views of two variants of the central core of the system of FIG. 15 with retractor rods disposed therein.

As depicted in FIGS. 16, 17 and 18A, grooves 582A-E are "loose fitting" and thus open toward an outer surface of central core 580, leaving a gap between the groove and a nested squid rod or retractor rod near the intersection of the groove and the central core outer surface. This groove shape is described as loose fit because the rods are guided by the grooves but not held in place with a snap in connection, as shown in FIG. 17, for example. In an alternative configuration, central core 680 includes grooves 682A-E which fit tightly around a squid rod or a rod disposed therein, such as retractor rods 651A-E shown in FIG. 18B. This alternative is also called a snap fit or tight fit and is advantageous where small movements of rods relative to the central core may be detrimental to a surgical procedure. In the depicted embodiments, the rods are shaped with a smooth, circular surface (convex) that interfaces with a complementary smooth circular surface (concave) on central core 580, 680.

Returning to the overall squid core combination structure 500, squid enclosure 590, shown in its entirety in FIG. 15, includes a unifying cap 595 and squid rods 598A-E extending therefrom. Squid rods 598A-E are attached to unifying cap 595 through slots in the unifying cap. As shown in FIG. 15, positioning of squid rods 598A-E in respective slots of the cap renders each squid rod radially adjustable to move away or toward a surface of central core 580, if desired. Alternatively, each squid rod 598A-E may be fixed in position relative to unifying cap 595. As noted above, each squid rod 598A-E is shaped to nest within recesses 582A-E of central core 580, and includes a partially circular cross-section to ensure an inner surface of such squid rods 598A-E are flush with respective grooves 582A-E when nested therein, as shown in FIG. 17. On an outward facing surface of each squid rod 598A-E are surfaces 597A-E, one for each squid rod, having a radius of curvature corresponding to that of central core 580, shown in FIGS. 16 and 17. This shape of squid rods 598A-E ensures not only that squid rods nest in central core 580, but that they do not protrude outside of an envelope of central core, minimizing a size of penetration when squid core combination structure 500 is inserted into a patient body. Similarly, and for similar reasons, a taper 593A-E at insertion ends of squid rods 598A-E includes an outward facing surface having a curved surface matching that of conical tip 583, as shown in FIG. 16.

Through this innovative combination, a diameter of the combined structure may be minimized. In one example, the diameter of the combined central core and squid rods is 11 mm. In the same example, a diameter of an outer envelope of the core with retractor rods nested therein is 12 mm. In other examples, a diameter of the squid core combination structure with squid rods disposed therein may be anywhere from 11 mm to 13 mm, with a corresponding increase in footprint with rods nested in the central core.

In sum, squid core combination structure 500 may be configured, depending on a stage in a surgical procedure, as squid enclosure 590 and central core 580 together or just central core 580, with central core 580 designed to function with retractor rods.

The retractor apparatus and its subcomponents and accessories may be varied in many ways. For instance, the system may include a retractor with a total of two or more rods and/or arms attached thereto. Additionally, any portion of the total number of retractor arms may be configured to include some or all with two or more degrees of freedom of movement. Similarly, within a single retractor, any two rods may include different features for independent movement. For example, where a retractor includes five rods attached thereto, only two or three of the five rods may be configured to toe in and out, while another rod may swing, toe in or out, and telescope toward and away from the arm. In another example where a retractor includes seven rods, one rod, six rods, or any number in between may be configured to have four degrees of freedom. When a retractor includes five rods each having a diameter of 4 mm, a diameter of the envelope of the rods when closed may vary from 11.1 mm to 13 mm. These alternatives may be implemented at the time of surgery through substitution of one rod for another or through substitution of retractor arms.

A specific structure of the rods may also be varied. For instance, a portal defining portion of the rod defining a portal size and shape when such rod is retracted with other rods of a retractor, e.g., having a cylindrical shape in rods 151A-E, may instead have an oval, elliptical, rectangular, or other polygonal cross-sectional shape. Other possibilities include a cross-sectional shape having some curved faces and some cornered edges. For any of these rod shapes, a size or shape of the cross-section of the portal defining portion may vary over the length of the rod. Similarly, the portal defining portion may have a tapering characteristic, becoming smaller in cross-sectional size moving away from an end connected to the retractor. The portal defining portion of the rod may also vary in any manner contemplated in WO2018/039228, the disclosure of which is hereby incorporated by reference herein in its entirety. Consistent with these examples, an end surface of the portal defining portion may be any shape and is not limited to the dome shaped structures depicted. In one example, an insertion end tip of the rod is pointed and may function as an anchor.

In other examples, the rod may have a width and/or diameter, or a length, to suit a particular application. For instance, a diameter of portal defining portions 152A-E of rods 151A-E may be 4 mm. Similar principles apply to a length of the rods, and rods may have a length ranging from 80 mm to 200 mm. This applies to any portal defining portion of a rod as described above or otherwise contemplated in this disclosure. Rods may also be as described in U.S. Provisional Patent Application No. 62/546,841 or WO2018/039228, the disclosures of which are hereby incorporated by reference herein in its entirety. In still further examples, any rods used as part of a retractor or larger system may be cannulated on a central axis of the portal defining portion or through any internal segment of the rod. The cannulation may be sized for placement of guidewire, elements for the transmission of light, such as fiber optic cables, or an electrode for neuromonitoring, among other purposes. A surface of the rod may also include recesses or other structural modifications to support the placement of LEDs on the rod. In other examples, the rods may include a hinge mechanism along their length so that toeing of an end portion of the rod is possible.

Turning to variants of the arm engagement portion of the rod, although FIGS. 1-4 illustrate rods with an arm engagement portion designed for securement of the rod to the retractor of FIG. 1, such structure may vary in any number of ways to accommodate a particular retractor structure used with the rod. In some examples, the arm engagement portion of the rod is sized and shaped so that the rod in which it forms a part is compatible with the retractors described in WO2018/039228. In other examples, the arm engagement portion may have a width wider or narrower than a corresponding portal defining portion of rod, it may extend a distance greater or lesser from portal defining portion than the arm attachment portions of FIGS. 1-4, and it may have any other shape to accommodate attachment to an arm or other actuation element of a retractor. A feature common to the arm engagement portion of the rods contemplated herein is its ability to be secured to a retractor and to facilitate securement of a squid cap thereon. In further examples, an outside edge and/or taper of the arm engagement portion (keel) may vary from the taper shown in the rod of FIG. 3 and may be customized as a matter of design choice. For example, instead of a gradual taper over a length of arm engagement portion 153A as shown in FIG. 3, an edge of the arm engagement portion remote from the cylindrical portion of the rod may be parallel to the cylindrical portion over most of its length and then taper sharply adjacent to its end remote from the arm toward an insertion end of the rod, i.e., have a trapezoidal geometry. Accordingly, such trapezoidal geometry includes a much steeper taper than that of rod 151A. With a shape of the rod as shown in FIG. 3, the rod is subject to lower insertion forces when advanced into tissue than with the above described trapezoidal geometry while the rod of FIG. 3, when used as a set of rods, creates a smaller sectional area for a viewing portal than a retractor with the rods having trapezoidal geometry. Thus, the geometry of the arm engagement portion may be customized to achieve a desired compromise between structure to reduce insertion forces versus rod geometry to maximize a viewing portal into the patient.

Figure 19B:
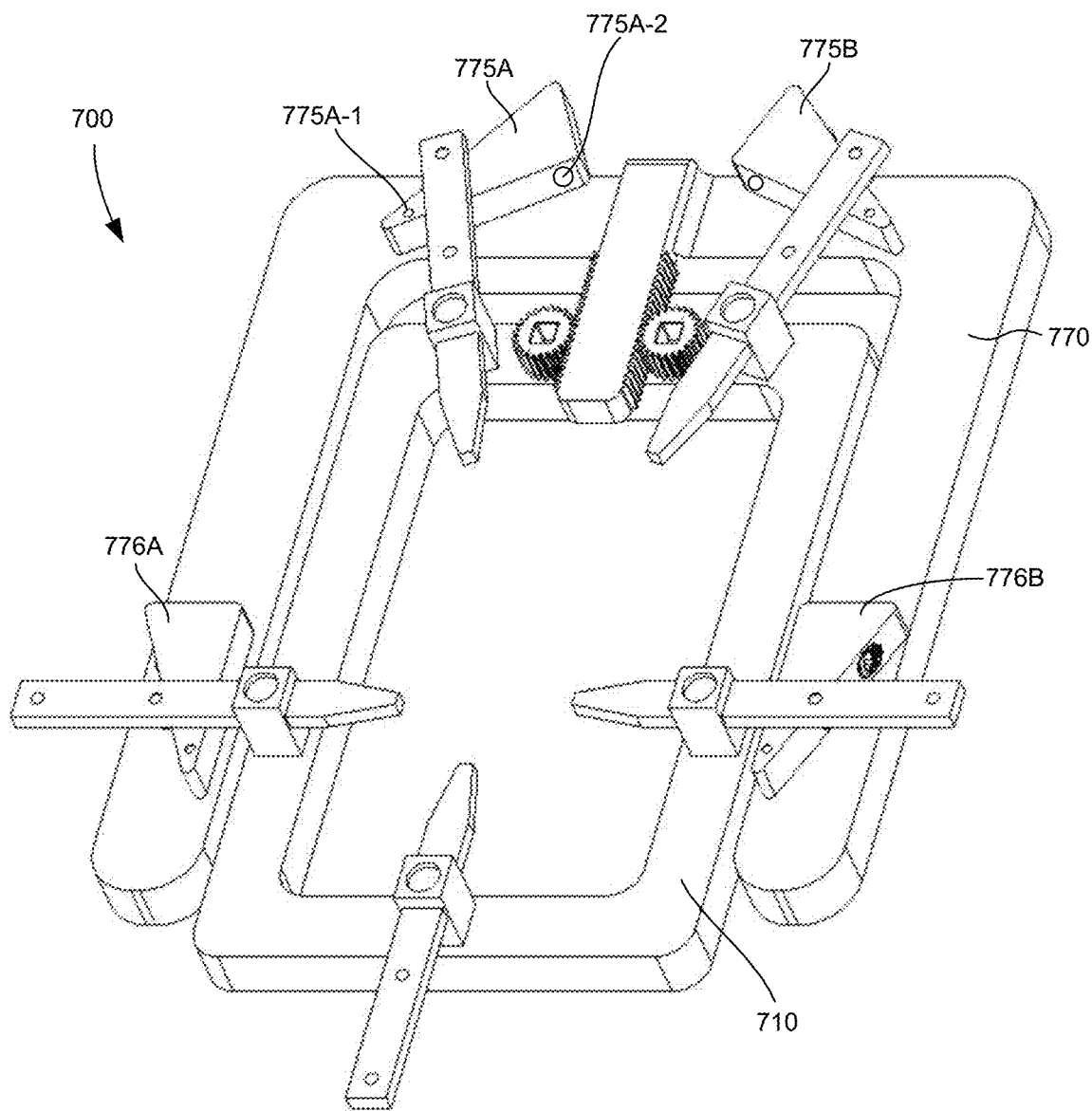
FIG. 19B is a perspective view of a retractor frame and slide element according to one embodiment of the disclosure.

In other variants, the slide tool may be modified. For example, slide tool may be as shown in FIG. 19B. Unless otherwise noted, like reference numerals refer to like elements as shown in FIG. 2. Slide tool 770 is movably attached to frame 710 and includes adjustable end ramps 775A-B and lateral ramps 776A-B. As depicted, each ramp includes an adjustment mechanism (e.g., 775A-2) and pivot point (e.g., 775A-1) about which a respective ramp rotates. Thus, each ramp is rotatable to change an angle of the ramp relative to an adjacent slide tool edge. The inclusion of this feature allows the shape of a surgical portal within retractor rods created through rapid expansion with slide tool 770 to be customized based on a user preference. In a variant, the ramps may also be slid longitudinally along the frame of the slide tool. In other examples, the specific mechanism connecting the ramps to the slide tool and the manner of movement of the ramps relative to the tool may be modified as a matter of design choice. Thus, it is contemplated that the ramping and ramp ratio between anterior-posterior rod movement and cranial-caudal rod movement can be customized in any manner desirable. Further, ramp rates may be non-linear or even irregular to promote changing directions of the rods during opening and/or changing speeds of opening.

Squid caps used with the retractors described in various embodiments of the disclosure may be varied in many ways. As a practical matter, the extensions of the squid cap include particular dimensions to suit the rods they are intended to contain. Thus, if the rods are of a larger cross section, then the slot between extensions on the squid cap will be wider to accommodate the rods. Any squid cap may be modified to include a built in central probe, with or without a cannulation, or otherwise include a central cannulation for a guidewire. The squid cap may also include extensions that are slightly biased in an inward direction, so that when squid cap is inserted over retractor rods, such as is shown in FIG. 7, the resistance from the extensions being forced outward assists in holding the rods in place relative to the squid cap. The handle for the squid cap may be modified in any manner desired as a matter of design choice.

Figure 18B:
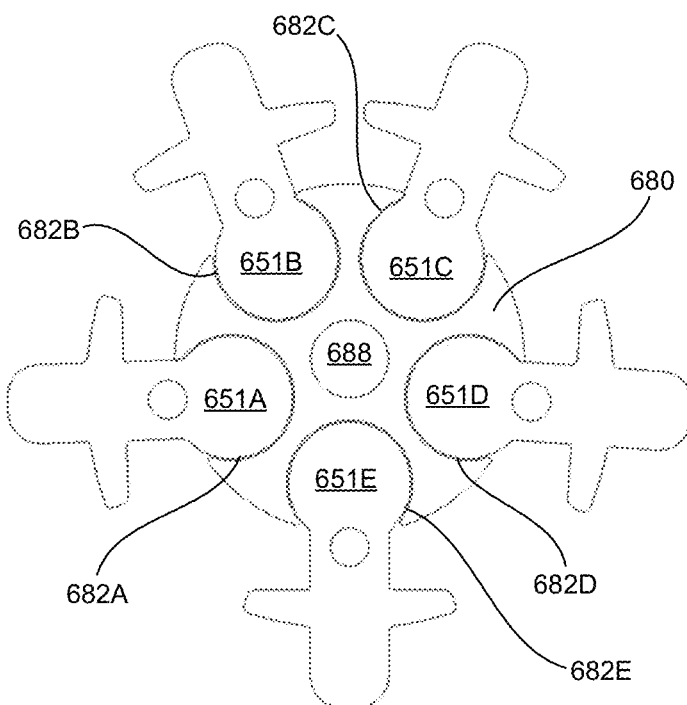

The central core may or may not include a central cannulation or a handle, and where a handle is included, the type used may be a matter of design choice. The central core element, or shaft, may include grooves or other surface features promoting the engagement between the core and rods of a retractor. Where rods of a retractor intended to be used are non-circular in shape, the recesses in a central core element may be shaped so that such rods may still nest therein. The grooves or recesses in the central core element may open up towards an outer surface, i.e., loose fit, or arc inward, such as is shown in FIG. 18B, to create a snap in fit for the rods. These features are interchangeable with any contemplated central core element. The outer shape of the central core may be tapered, non-circular or another shape to suit a desired retraction procedure and ultimately a desired working portal shape. The tip of the central core element may also be varied to have no taper, a steeper taper, or one having a shape other than those illustrated herein.

In some examples where a probe is used in conjunction with a squid cap, the probe is cannulated with a 6 mm diameter. In other examples, the probe may have a smaller diameter and perform the function of a guidewire, thus removing the need for a separate guidewire. In still further examples, the probe may have a 6 mm diameter, but may include a wire at an insertion end fixed to the probe and extending to a tip. In this instance, the wire tip may engage with a patient's anatomy, such as an intervertebral disc, and thereby perform the function of a guidewire anchoring to the target site.

In any one of the above system embodiments, one or more rods of a retractor may include neuromonitoring technology. Although the following examples describe neuromonitoring as applied to a single rod, e.g., posterior rod 151E in a lateral trans-psoas procedure, it should be understood that such structures may be included in any number of rods attached to a retractor, a probe or a central core element, among other system components. In one variant, a rod is cannulated through its length and includes an electrode disposed therein. The electrode extends to an end of the rod distal to an attached retractor arm and exits from a surface of rod offset from its center. Alternatively, it may exit on a centerline of rod. To ensure any electricity flowing through the electrode is directed to the distal tip of the rod, the majority of the rod length is insulated with a polymer material, for example, while the tip includes an exposed metallic surface. In another variant, the rod does not include a separate cannulation for an electrode and instead the electrode is attached to a surface of the rod and independently insulated. Because the electrode is designed to transmit an electric charge to stimulate areas proximal to it in a surgical portal, other envisioned configurations include an electrode over the length of the rod that is exposed at various points along the length of the rod, providing stimulation at locations in addition to the distal tip of the rod. Other components in a rod with neuromonitoring include a separate electrode or electrodes proximal to the nerve or muscle of concern to function as a sensor and a computer system for sending stimulation signals to the rod and to receive data from the nerve response to the stimulation. Incorporation of neuromonitoring into a probe or central core element may be achieved with similar structure as that described for the rod above.

As an alternative to having neuromonitoring on a rod, probe or central core element, a wand may also be included which may be used in the same manner to stimulate nearby tissue including nerves. It should be noted that in alternative arrangements, a retractor and its accessories may include no neuromonitoring.

In other embodiments, the retractor may be supplemented with a navigation system. Incorporation of a navigation system may be used to improve accuracy of placement for the probe and guidewire and during surgical procedures may reduce the number of fluoroscopy readings necessary. In some situations, use of navigation may allow viewing of the surgical procedure without the use of k-wire.

In its most basic form, the navigation system includes a power source, a controller with a user interface to monitor advancement of the retractor rods, a connective element to connect the controller with a sensor, and a sensor adapted to monitor the location of a central core, probe or rod it is connected to. The connective element is wireless but can also include a physical wire attached to the sensor. The controller and accompanying monitoring equipment are positioned outside of the body throughout the procedure. In one example, the interface included with the monitoring equipment is a trackable device on the surface of the body of the patient and includes LEDs attached thereon for monitoring the position of the central core, probe and/or rods. The interface is configured so that the target anatomical location, e.g., intervertebral disc, is identifiable throughout the procedure, including its position relative to the elements with a sensor thereon. An exemplary navigation system of the variety described above that can be employed in conjunction with the methods described herein is the Spine-Mask® Non-Invasive Tracker by Stryker® described in U.S. Pat. App. Pub. No. 2015/0327948, the disclosure of which is hereby incorporated by reference herein in its entirety. The navigation system is configured so that when the retractor rods are inserted into the patient, the location and trajectory of the rods can be monitored during advancement and adjusted prior to reaching a final position adjacent to the anatomical location that is the subject of the surgery. Through this approach, the need for adjustment after the rods are fully inserted into the body is either eliminated or at least minimized. In a variant, two or more sensors can be placed on one or more of the central core, probe and rods. In some examples, traditional surgical instruments may be used with navigation by providing a spine lock clamp attachable to the instrument.

Figure 25:
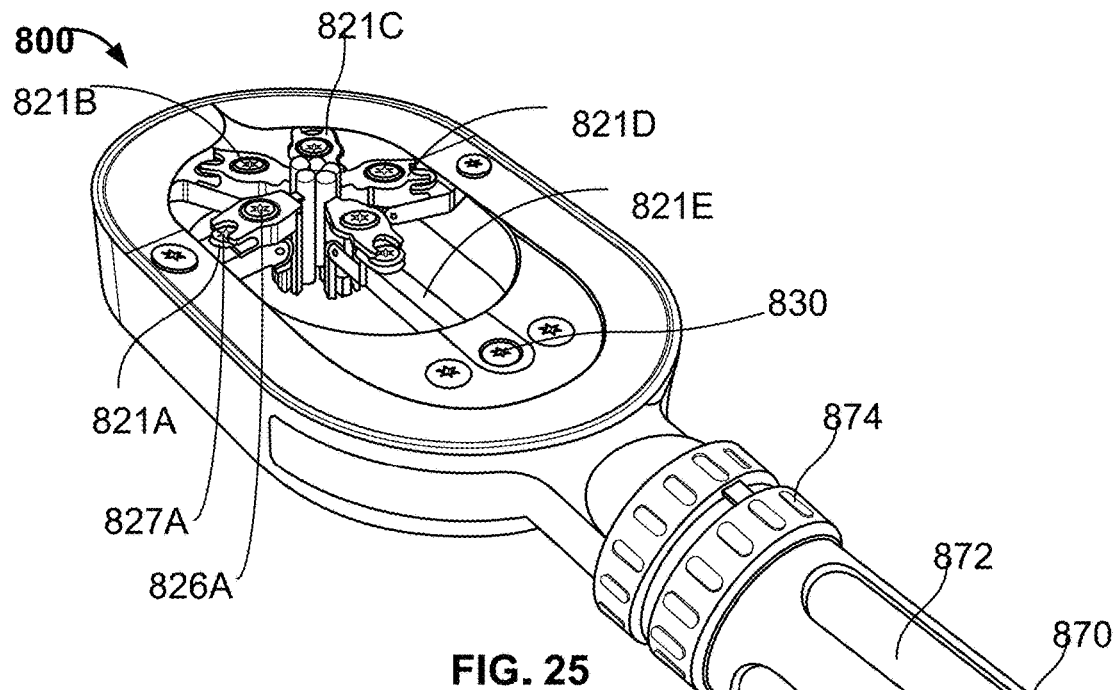
FIGS. 25-26 are perspective views of a retractor with handle in closed and open positions, respectively, according to one embodiment of the disclosure.
Figure 26:
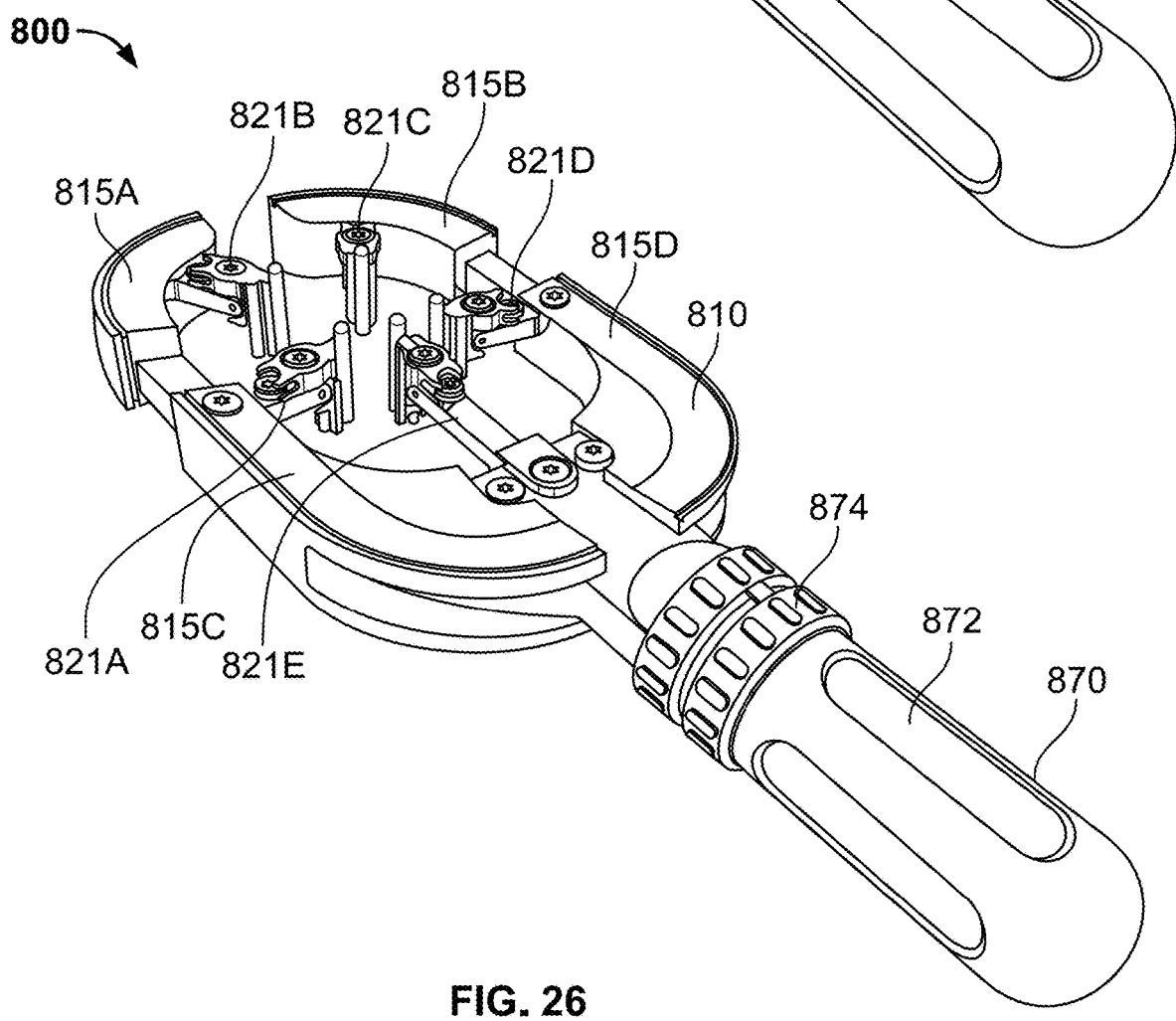
Figure 51:
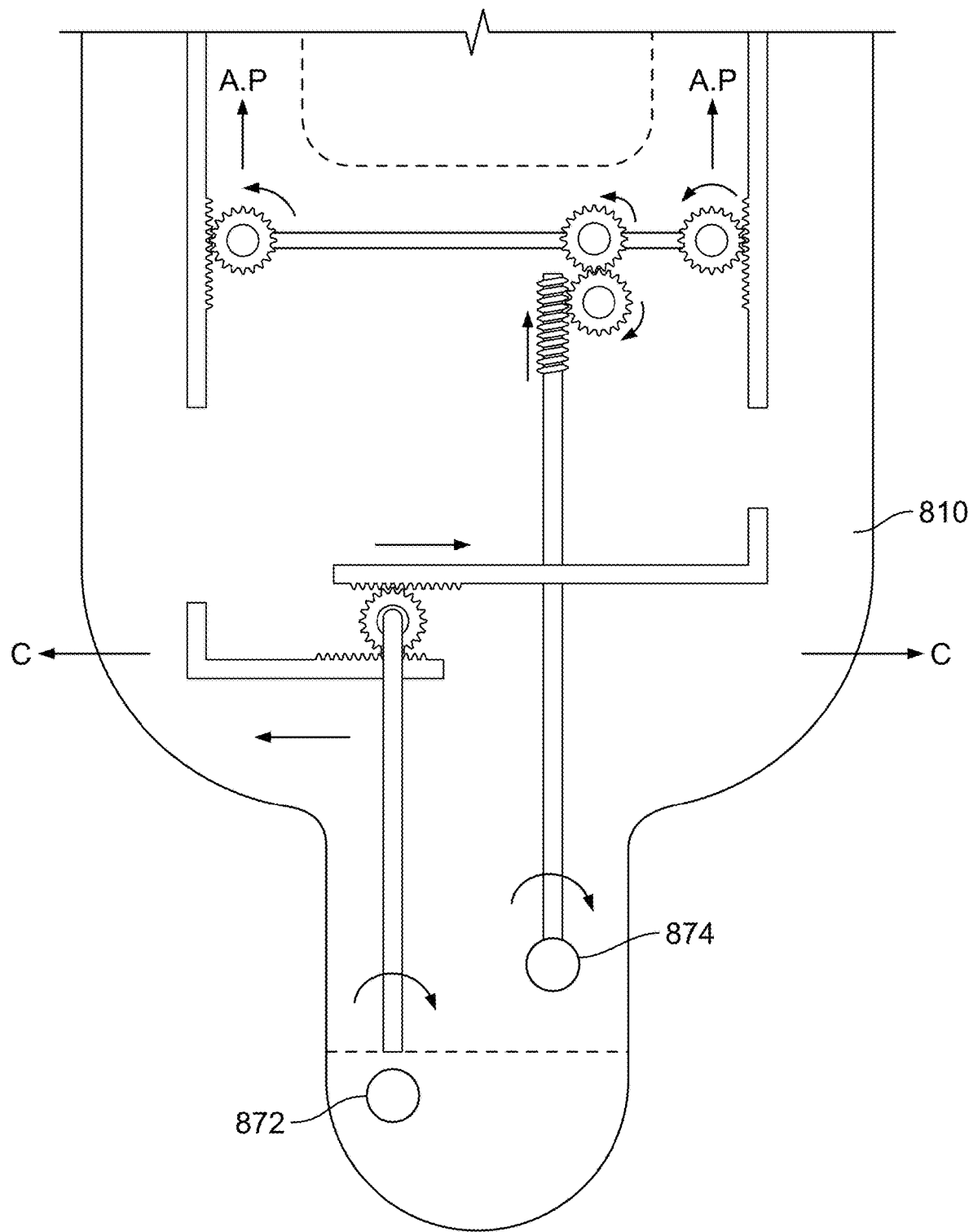
FIG. 51 is a top view of mechanical components within a retractor and handle combination according to one embodiment of the disclosure.

In another embodiment, a retractor 800 is as shown in FIGS. 25-26. Like reference numerals refer to like elements present in the embodiment of FIG. 1. Retractor 800 includes a handle 870. Handle 870, in turn, includes two dials 872, 874, which are interconnected with frame 810. Frame 810 includes four segments, 815A-D, as shown in FIG. 26. In one example of a retractor with the features of retractor 800, the frame measures 134 mm in a long dimension and 87 mm in a short dimension when it is closed. A retractor having a size noted in the aforementioned example may be used to create an opening, i.e., surgical portal, up to 20 mm×30 mm in dimensions. Of course, the exact dimensions of the retractor may vary and may be larger or smaller than the aforementioned example. Separation (retraction) between segments 815A, 815B and 815C, 815D, in the anterior-posterior direction when performing lateral surgery, is controlled through actuation of dial 874. A series of mechanical parts or components provides a link between the respective elements and is used to effectuate such separation, or in reverse, closure. The mechanism included for retraction or closure in the anterior-posterior direction is a worm drive or alternatively a rack and pinion mechanism. Separation between segments 815A, 815C and 815B 815D, in the cranial-caudal direction when performing lateral surgery is controlled through actuation of dial 872. Mechanical components in the form of a rack and pinion interconnect these segments. Thus, a mechanical connection between the dials and the frame provides a link between the dials and the respective frame segments so that a space between the rods is controllable, i.e., open and closed positions. One example of these mechanisms built into the handle and frame is illustrated in FIG. 51, with the motion of actuating dials 872 and 874 shown.

Of course, the exact alignment, size, placement and other details for the gear, rack, pin and other components may vary according to the particular handle-frame configuration. Although not specifically mentioned for each retractor embodiment incorporating a handle, such mechanical components may be employed in the various retractor-handle combination structures of the present disclosure, including those with actuating mechanisms in the form of swinging handles, trigger handles, and buttons, among others. Additionally, other mechanical components serving the same function as a rack and pinion and worm gear may also be used if suitable based on a particular frame shape and handle.

Figure 38:
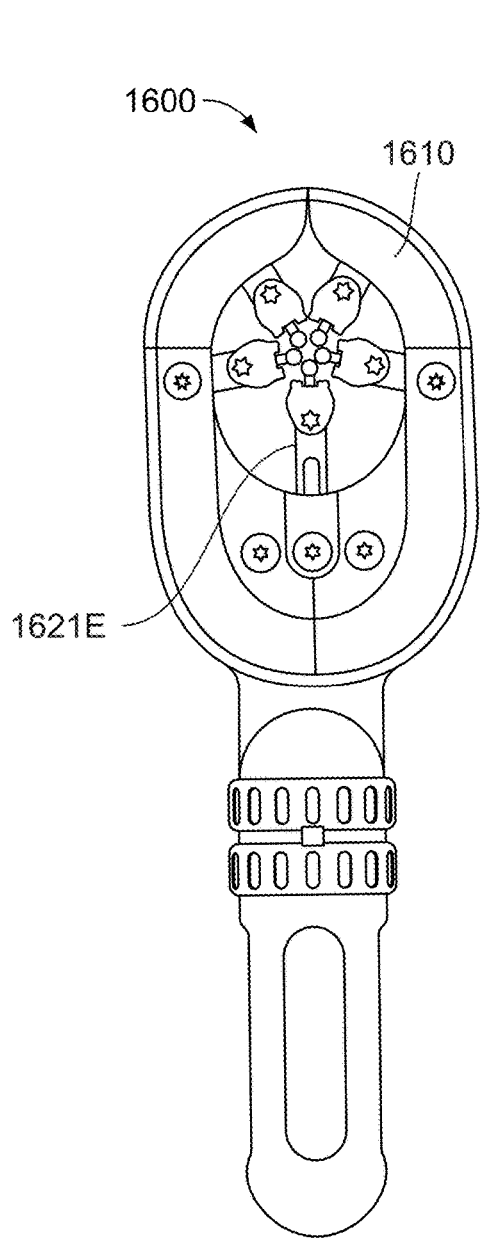
FIGS. 38-39 are top views of a retractor according to one embodiment of the disclosure in closed and open positions, respectively.
Figure 39:
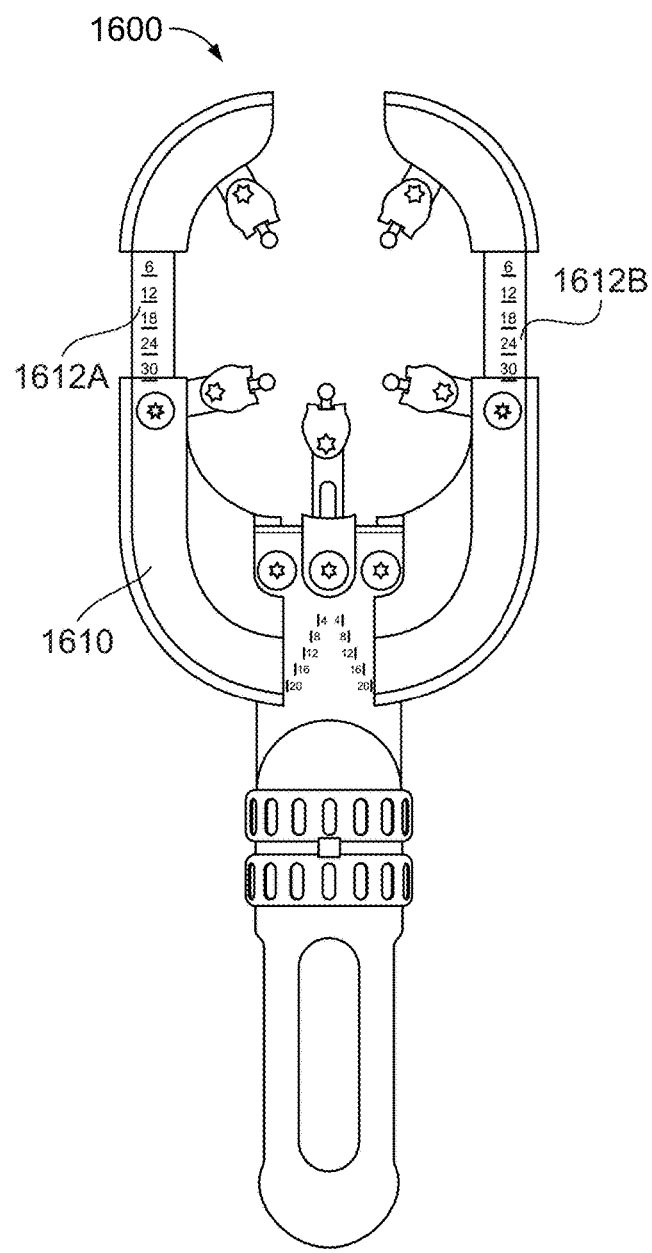

Color coding on frame 810 may be used to identify which dial controls cranial-caudal retraction and which dial controls anterior-posterior retraction. Retractor 800 allows for rapid opening via handle 870, toeing of rods via toeing cams, e.g., toeing cam 827A, individual rod retraction, and individual rod lengthening, i.e., extending depth of rod relative to the frame via threaded inserts, e.g., threaded insert 826A. The rod attached to arm 821E in FIGS. 25-26, e.g., the posterior rod in a lateral trans-psoas procedure, may be adjusted in the axis of the arm up to 20 mm. Such translation may be effectuated mechanically, for example, through actuation of threaded element 830. In other embodiments, the handle with dials as shown in FIGS. 25 and 26 may be used with retractors described in other embodiments of the disclosure. In still further embodiments, a retractor may include similar features as that shown in FIGS. 25 and 26, but have smaller dimensions. For example, as shown in FIGS. 38 and 39, retractor 1600 includes a rapid opening feature and its frame 1610 measures 106 mm in a long dimension and 69 mm in a short dimension when closed. A retractor having a size noted in the aforementioned example may be used to create an opening, i.e., surgical portal, up to 20 mm×30 mm in dimensions. Even in these reduced dimensions, retractor 1600 as shown allows for rod toeing and individual rod retraction. The rod attached to arm 1621E in FIG. 38, e.g., the posterior rod in a lateral trans-psoas procedure, may be adjusted in the axis of the arm up to 10 mm. A frame for retractor 1600 may vary in size as a matter of design choice, and may be larger or smaller than the above referenced example. For instance, the frame may be less than 106 mm long, 130 mm long, or any length in between. It may have a width less than 69 mm, 85 mm, or any width in between. The frame may also be larger than the upper end of these examples. A combination of length and width for the frame is a matter of design choice.

Figure 40:
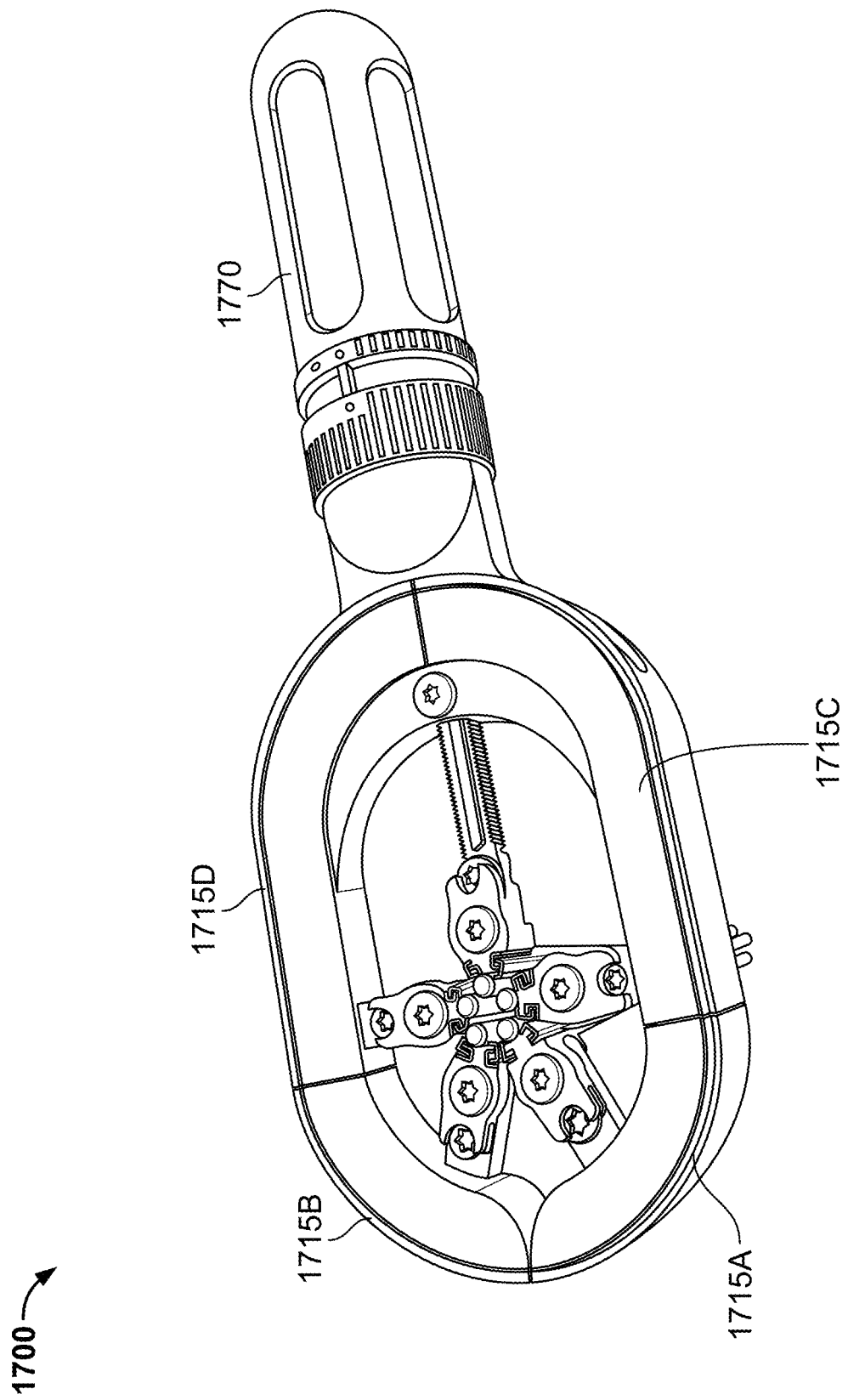
FIG. 40 is a perspective view of a retractor according to one embodiment of the disclosure.
Figure 41:
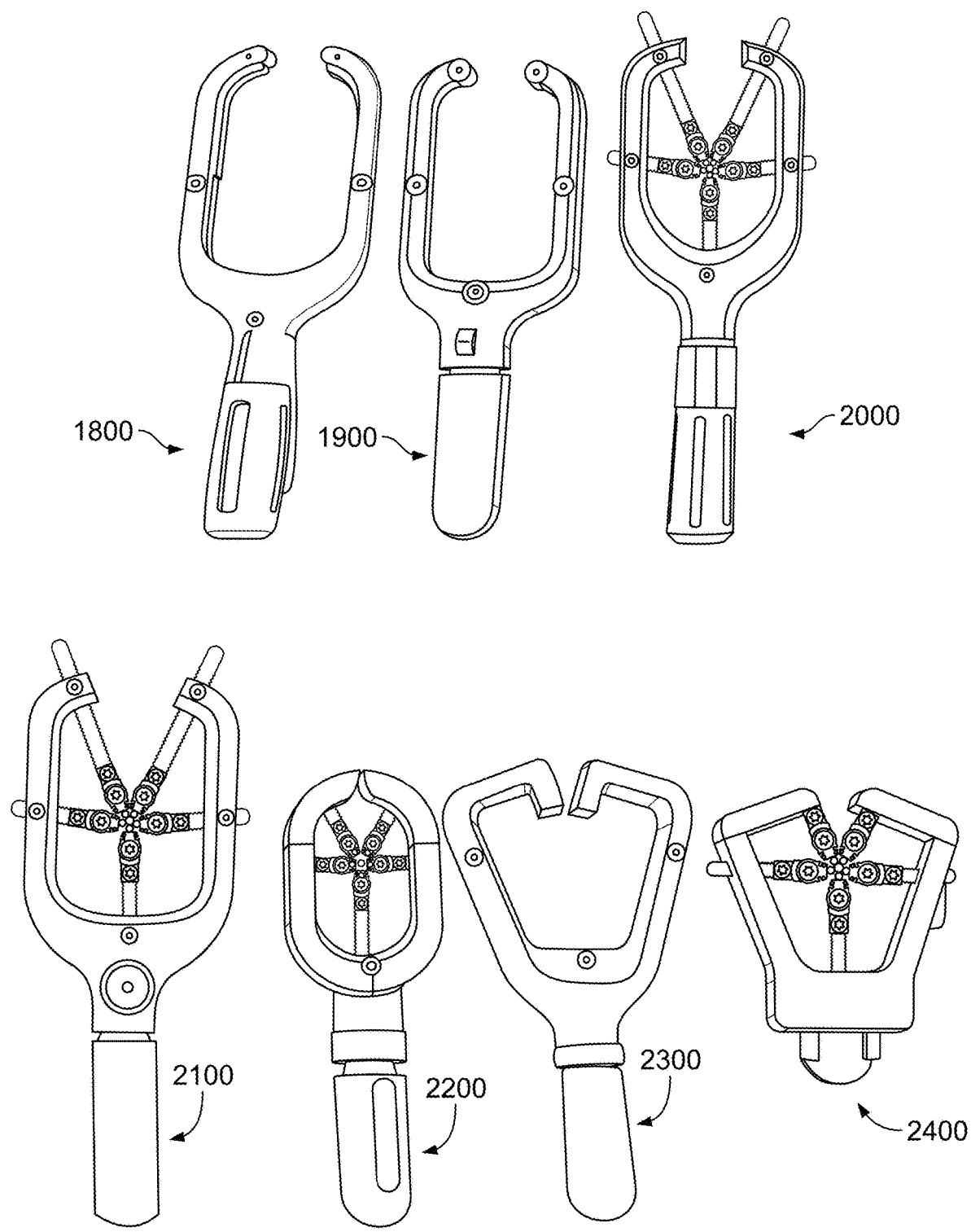
FIG. 41 is a top view of retractor frame and handle combinations according to several embodiments of the disclosure.

In another embodiment, a retractor with attached handle is as shown in FIGS. 36A-36B and 37A-37B. Elements of retractor 1500 are similar to those of retractor 800 shown in FIGS. 25-26 and like reference numerals refer to like elements. Yet another embodiment of a retractor with handle is shown in FIG. 40. Elements of retractor 1700 are similar to those of retractor 800 shown in FIGS. 25-26 and like reference numerals refer to like elements. Various other retractor frame and handle combinations are shown in FIG. 41 including retractors 1800, 1900, 2000, 2100, 2200, 2300 and 2400.

Figure 42:
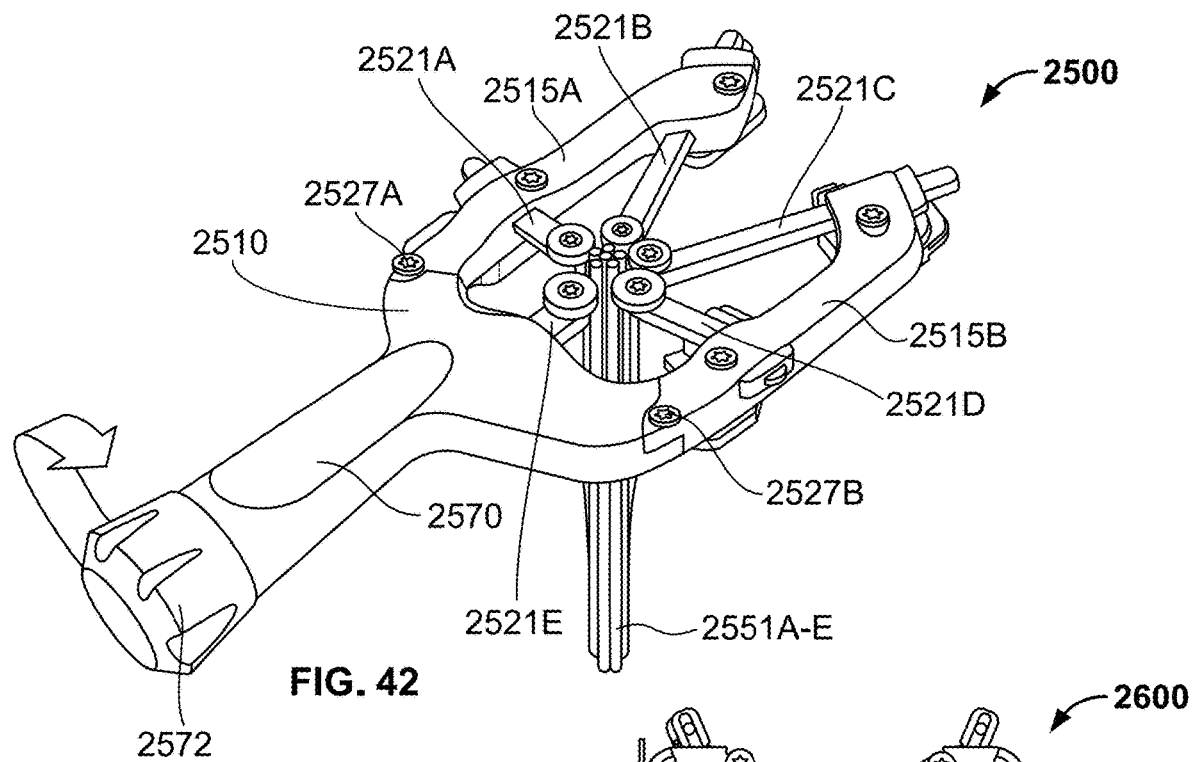
FIG. 42 is a perspective view of a retractor according to one embodiment of the disclosure.

In still further embodiments, a retractor 2500 may be as shown in FIG. 42 with a handle 2570 adapted so that rotation of the handle produces toeing in one or more rods through a mechanical connection. Unless otherwise noted, like reference numerals refer to like elements as shown in FIGS. 1, 2 and 20, but in the 2500 series of numbers.

Retractor 2500 includes a central frame 2510 with a first frame extension 2515A and a second frame extension 2515B, each extending approximately in parallel and on opposite sides of the retractor structure. Each of the first and second frame extensions includes a pair of arms extending inwardly therefrom, 2521A-B and 2521C-D, respectively. Rods 2551A-D are attached at the end of each arm, as shown in FIG. 42. From a central portion of central frame 2510 extends a posterior arm 2521E with a rod 2551E attached to its free end. The rods are shown in the closed position in FIG. 42. Retractor also includes toeing cam 2527A on first frame extension 2515A and toeing cam 2527B on second frame extension 2515B. Each toeing cam is actuatable to control rotation of the respective frame extension about its axis, which in turn toes the rods attached to the frame extension. Rotation of frame extensions 2515A-B is relative to a stationary position of central frame 2510. Thus, actuation of toeing cam 2527A causes toeing of rods 2551A, B attached to arms 2521A, B relative to central frame 2510 and the rest of the retractor structure. Toeing cam 2527B functions in the same manner. Posterior rod 2551E attached to arm 2521E is linearly translatable either manually or through a mechanical element such as a rack and pinion or another mechanisms described elsewhere in the disclosure. Similarly, each of the arms other than the posterior arm may be translated along its longitudinal axis through central frame 2510. In other examples, the arms attached to the first and second frame extensions may be fixed. The actuation mechanism on handle 2570, shown as dial 2572, controls rapid opening of the plurality of rods on the retractor through mechanical elements internal to the frame.

In one variation of the retractor shown in FIG. 42, a retractor includes a central frame with a first frame extension and a second frame extension, each frame extension having two arms with rods attached thereto, a posterior arm with rod attached extending from the central frame, and a handle on an end of the central frame including actuation mechanisms to control the position of the rods. As with retractor 2500, the retractor includes respective toeing cams to control toeing of the pair of arms extending from the applicable frame extension. In one example, the toeing cams are positioned on the respective frame extensions. In another example, the toeing cams are positioned adjacent to the frame extensions on the central frame. Additionally, each of the first frame extension and the second frame extension includes two segments that are separable from one another to control a length of the frame extension. This feature is shown separately in other embodiments of the disclosure such as with segments 815A, B extendable relative to segments 815C, D, respectively, in retractor 800 shown in FIGS. 25-26 and also in retractor 1600 shown in FIGS. 38-39. The segments of each frame extension move relative to each other so that the two arms attached to the applicable frame extension move closer or further apart when the frame extension shortens or lengthens. For example, an arm attached at an anterior end of a frame extension becomes closer to or further from an arm attached at a proximal end of the frame extension when a control is actuated.

Continuing to describe the above variation of the retractor, the handle of the retractor includes a first actuation mechanism such as a dial to control the shortening or lengthening of the first frame extension and the second frame extension. In one example, the dial controls both frame extensions simultaneously so that each shortens or lengthens in unison. In another example, two dials may be included on the handle, one to control each frame extension. In a lateral procedure, the shortening or lengthening of each frame extension is in the anterior-posterior direction. Additionally, the central frame attached to the posterior arm and abutting each of the first and second frame extensions is further divided into three parts: A central region and two side regions that each become separate from the central region upon actuation of a second actuation mechanism on the handle. When each side region of the frame separates from the central region, it moves orthogonally relative to a length of each frame extension and translates with a respective frame extension as it separates. With this control, first frame extension and second frame extension become closer or further apart in a cephalad caudal direction. Further, in this variation, the frame optionally includes a third actuation element to control translation of the posterior arm along its longitudinal axis.

Figure 43:
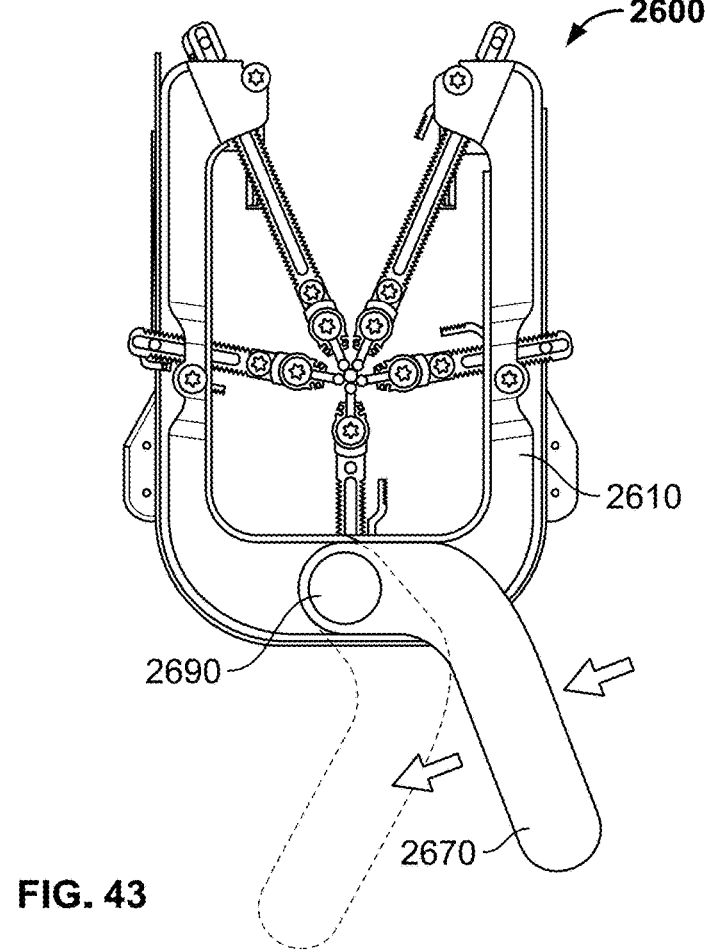
FIG. 43 is a top view of a retractor according to one embodiment of the disclosure.
Figure 44:
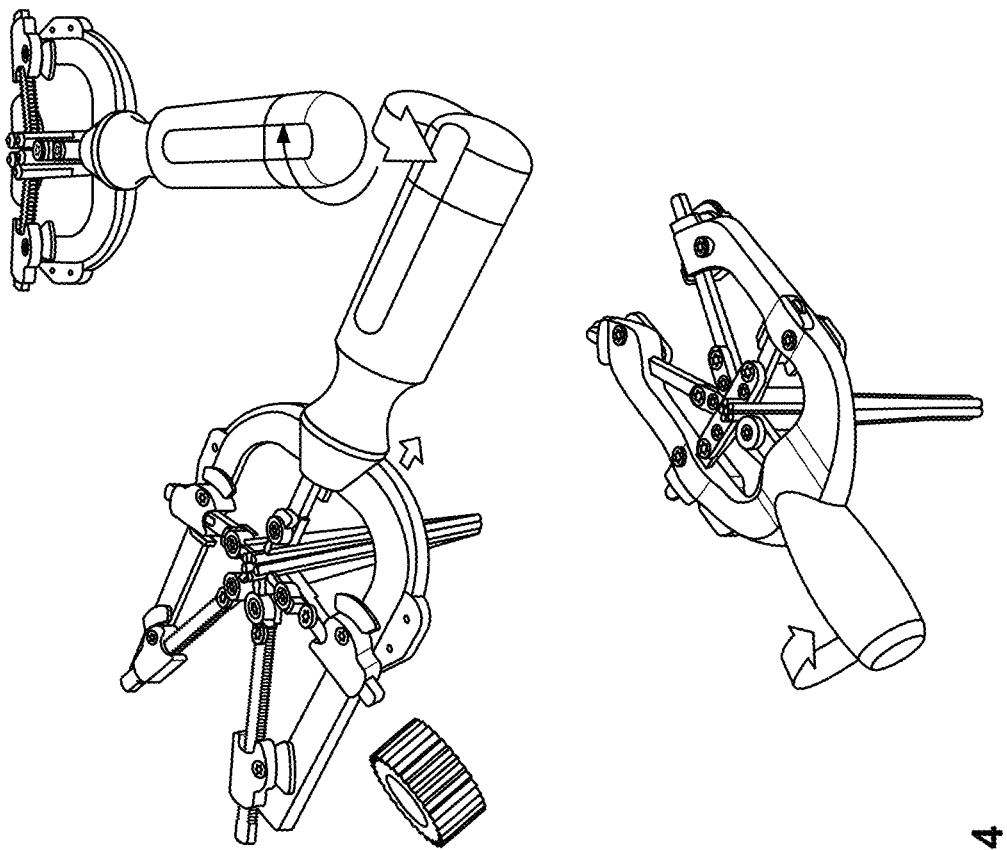
FIG. 44 includes several views of a retractor according to one embodiment of the disclosure.
Figure 44:
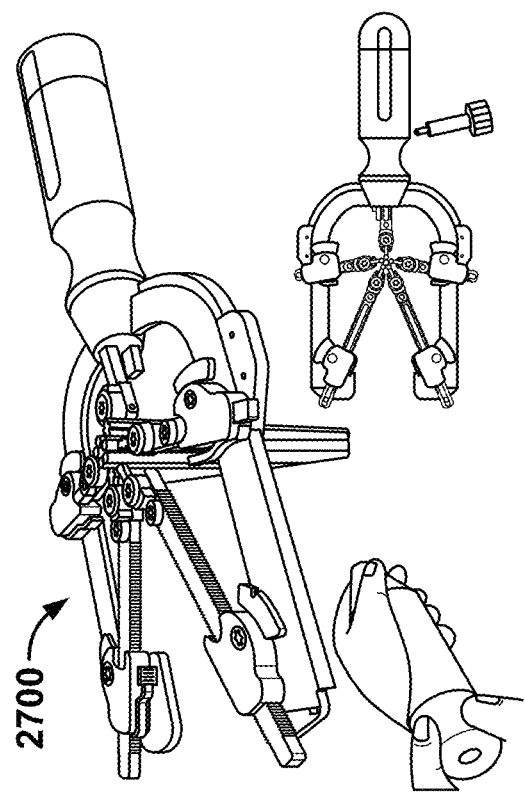

A variant of the retractor shown in FIG. 42 is retractor 2700 depicted in FIG. 44. In another embodiment depicted in FIG. 43, a retractor 2600 includes a handle 2670 attached to a pivot point 2690 on frame 2610. Although depicted as a right-handed handle in FIG. 43, it is contemplated that the handle may also be left-handed on an opposite side of the frame. The handle is connected to the arms of the retractor so that actuation of the handle causes on or more rods to retract. In one example, actuation of the handle causes a rack and pinion and or worm gear mechanism to operate causing the arms of the retractor to retract. Alternatively, the connection between the handle and the arms may simply allow the handle to be rotated to make room for the user of the retractor. It is contemplated that handle 2670 may be rotated all the way to the frame edge. In other embodiments that are not shown, other actuation elements can be incorporated into the handle such as a squeeze trigger and or a release button. Each of these may be interconnected with mechanical components such as those already described.

Figure 47A:
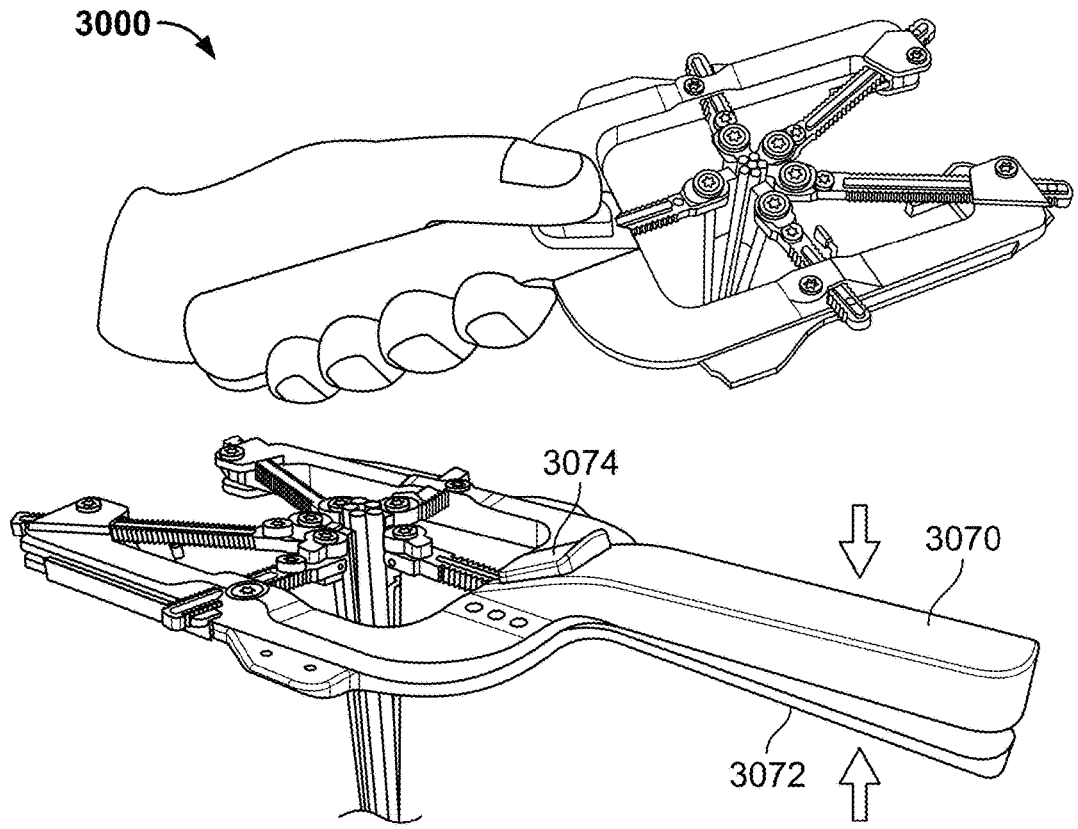
FIG. 47A includes two views of a retractor according to one embodiment of the disclosure.
Figure 47B:
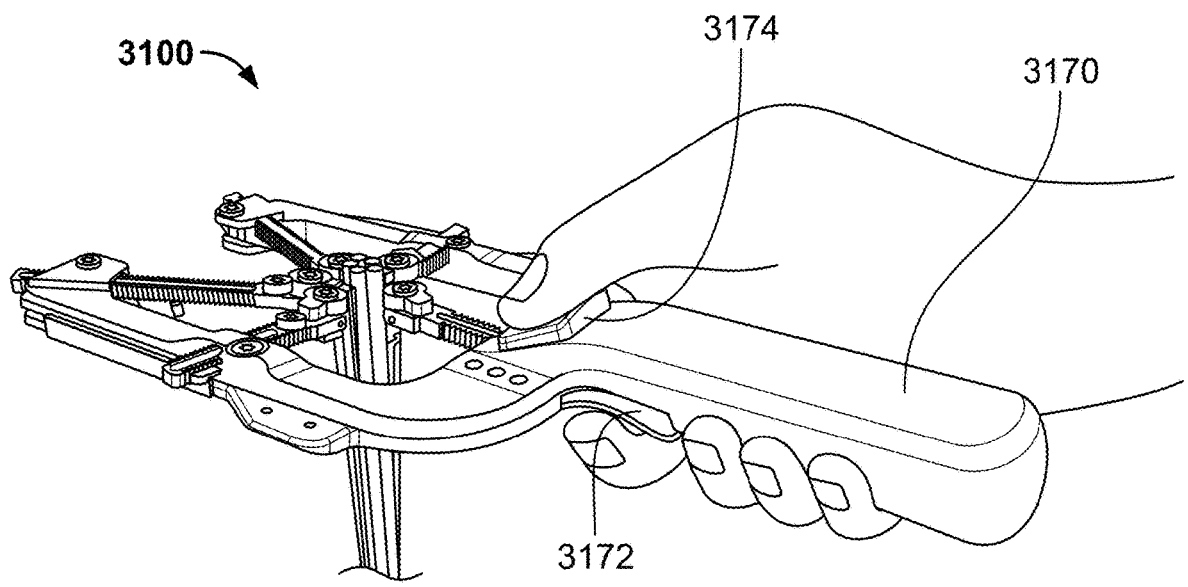
FIG. 47B is a perspective view of a variant of the retractor depicted in FIG. 47A.

In yet another embodiment, a retractor with handle is as shown in FIG. 47A. Retractor 3000 includes handle 3070 having a trigger ratchet mechanism 3072 and a release button 3074. Ratchet mechanism 3072 is adjustable in increments and incorporates audible feedback such as clicking so a user recognizes when and how much the ratchet mechanism is adjusted. Actuation of ratchet mechanism 3072 controls rapid opening of retractor arms. Release button 3074 is actuatable to undo the incremental closure of ratchet mechanism 3074 upon holding or otherwise pressing button 3074. Alternatively, release button 3074 may merely cause force pulling on respective arms to be relaxed or may function as a reverse switch. In a variant, a retractor 3100 is as shown in FIG. 47B, and trigger ratchet mechanism 3172 is more compact, although performs the same function.

In some embodiments, the retractors of the various embodiments of the disclosure may further include any one of the handles shown in FIGS. 27-30. Each handle shown in FIGS. 27-30 includes an engagement feature for attachment or detachment to a retractor so that the handle is removable. Further, color coding on each handle 970, 1070, 1170, 1270 may be used to identify which dial or trigger controls cranial-caudal retraction and which dial or trigger controls anterior-posterior retraction. Although reference is made below to a specific rotation of dials for retraction, it is contemplated that the handles may be configured to retract rods of a retractor with rotation in the opposite direction of that noted.

Figure 27:
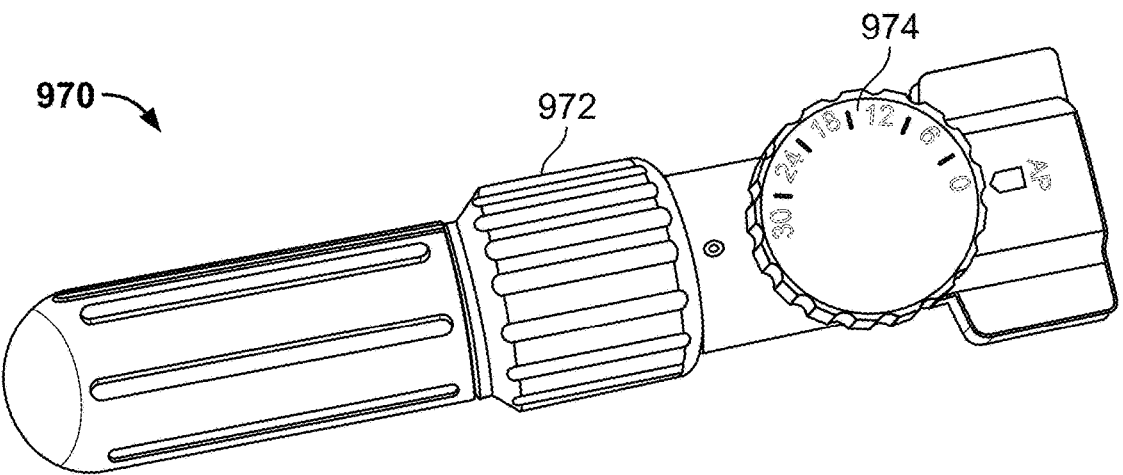
FIGS. 27-30 are perspective views of retractor handles according to unique embodiments of the disclosure.

Handle 970 is shown in FIG. 27 and includes an upper dial 974 and a rotary dial 972. Upper dial 974 controls anterior-posterior movement of the retractor arms, and, as depicted, controls such movement in 6 mm predetermined increments, with indicators provided on the dial. Rotary dial 972 controls the cranial-caudal movement of the retractor arms, and, as depicted, controls such movement in 4 mm predetermined increments. Counterclockwise movement of either dial 972, 974 expands the rods, while clockwise movement closes the rods. In variants, the number of settings or the increments for adjustment on either dial may be varied as a matter of design choice.

Figure 28:
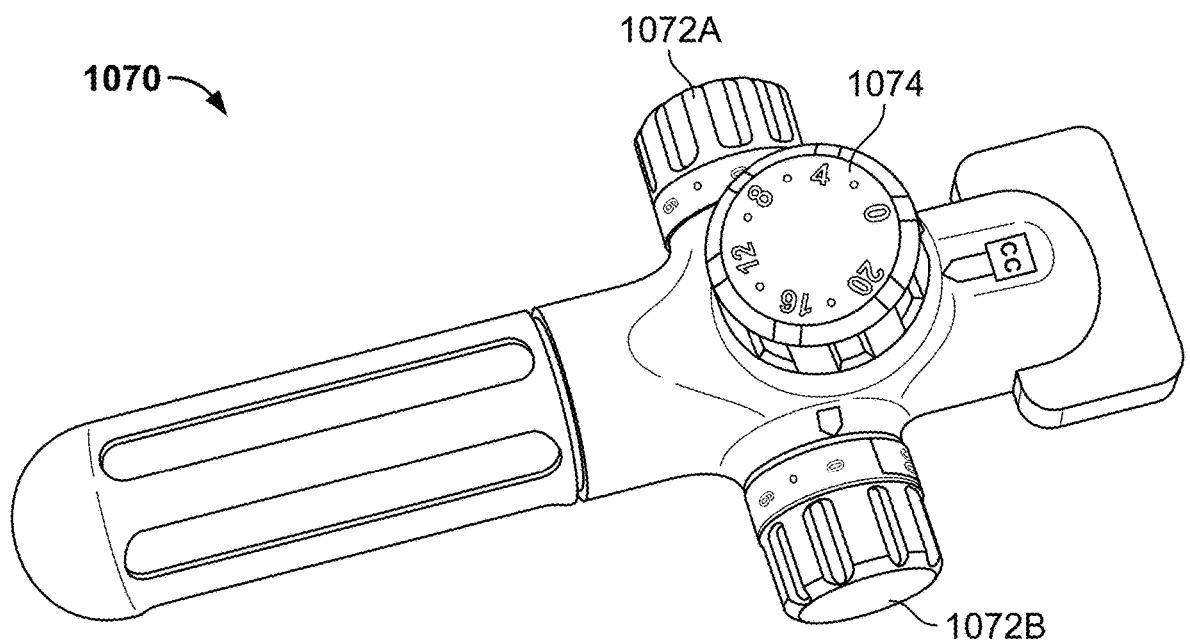

Handle 1070 is shown in FIG. 28 and includes side dials 1072A-B and an upper dial 1074. Side dials 1072A-B control anterior-posterior movement of the retractor arms, and, as depicted, control such movement in 6 mm predetermined increments, with indicators provided on the dial. Actuation of a side dial 1072A, 1072B causes the other side dial to actuate in unison. Clockwise movement of the dial expands the rods, while counterclockwise movement closes the rods. Upper dial 1074 controls the cranial-caudal movement of the retractor arms, and, as depicted, controls such movement in 4 mm predetermined increments. Clockwise movement of the upper dial expands the rods, while counterclockwise movement closes the rods. In variants, the number of settings or the increments for adjustment on either dial may be varied as a matter of design choice.

Figure 29:
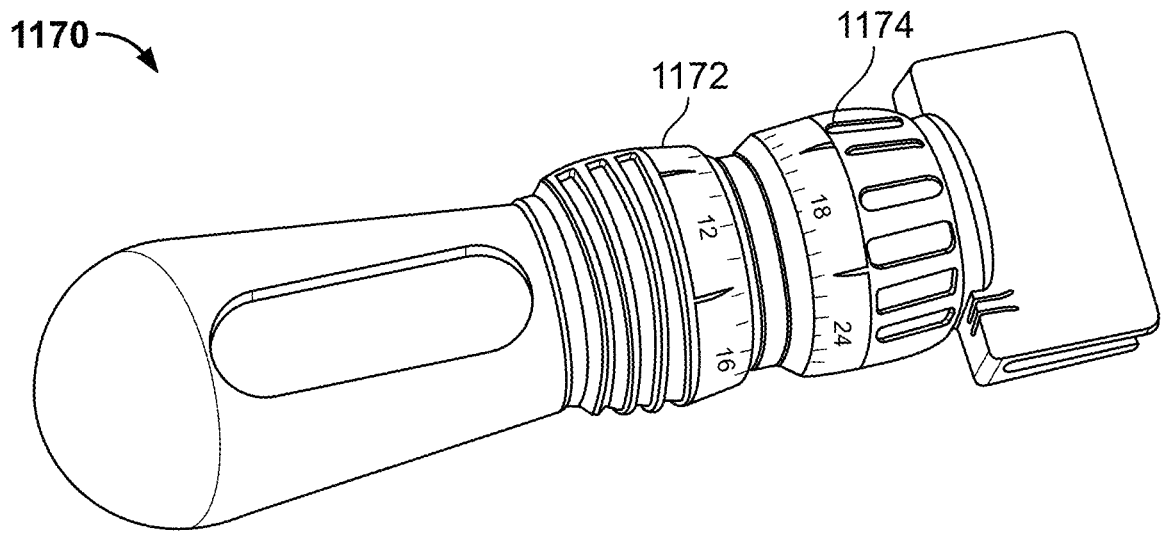

Handle 1170 is shown in FIG. 29 and includes an upper dial 1174 and a lower dial 1172. Upper dial 1174 controls anterior-posterior movement of the retractor arms, and, as depicted, controls such movement in 6 mm predetermined increments, with indicators provided on the dial. Clockwise movement of the dial expands the rods, while counterclockwise movement closes the rods. Lower dial 1172 controls the cranial-caudal movement of the retractor arms, and, as depicted, controls such movement in 4 mm predetermined increments. Clockwise movement of the lower dial retracts the rods, while counterclockwise movement closes the rods. In variants, the number of settings or the increments for adjustment on either dial may be varied as a matter of design choice.

Figure 30:
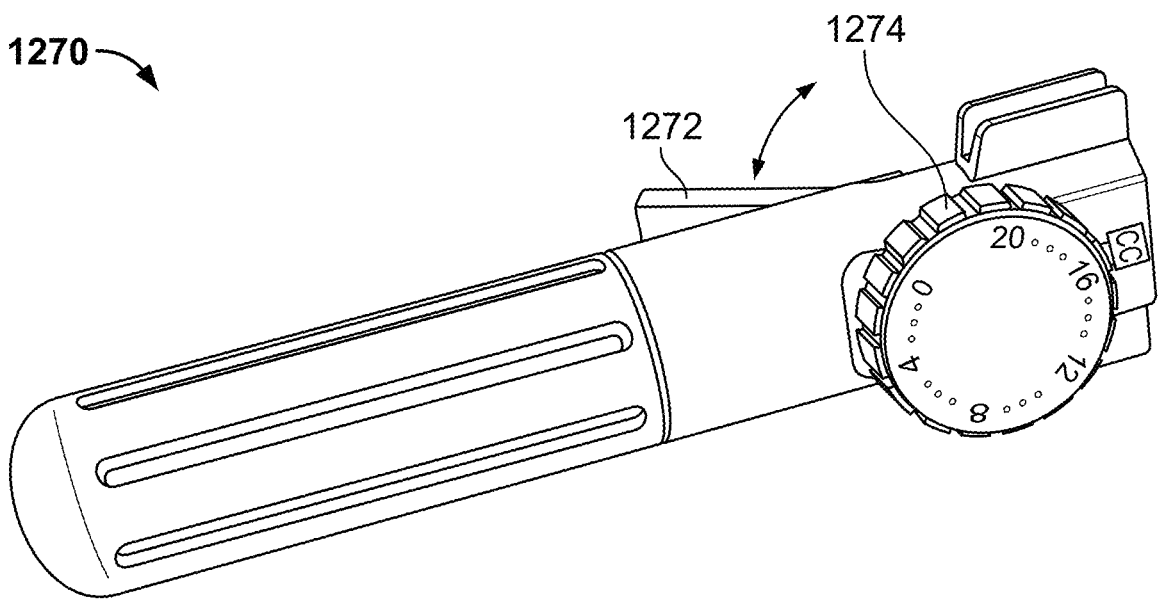

Handle 1270 is shown in FIG. 30 and includes an upper dial 1274 and a trigger 1272. Upper dial 1274 controls cranial-caudal movement of the retractor arms, and, as depicted, controls such movement in 6 mm predetermined increments, with indicators provided on the dial. Counterclockwise movement of the dial retracts the rods, while clockwise movement closes the rods. Trigger 1272 controls the anterior-posterior movement of the retractor arms, and, as depicted, controls such movement in 4 mm predetermined increments via a clicking mechanism. In variants, the number of settings or the increments for adjustment of the dial or trigger may be varied as a matter of design choice.

Figure 48:
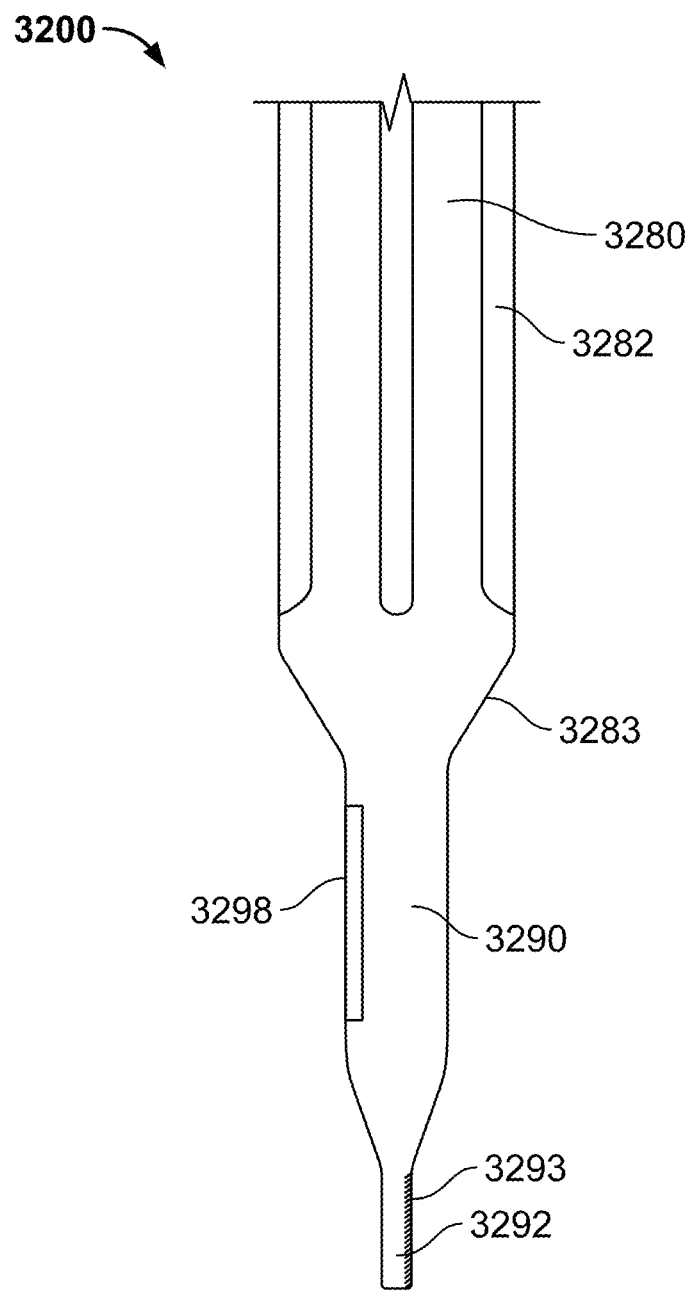
FIG. 48 is a side view of a combined central core and probe structure according to one embodiment of the disclosure.

In another embodiment, a retractor system may be complemented by a combined, all-in-one central core and probe structure 3200, as shown in FIG. 48. Employment of combined structure 3200 may eliminate the necessity of using a probe separately from initial retraction steps when creating a surgical portal. Structure 3200 includes a core section 3280, a tapering section 3283, a probe section 3290 and a tip section 3292. Core section 3280 includes grooves 3282 for the rods similarly to the core element shown in FIGS. 9 and 10, for example and may have a similar sectional dimension. The probe section includes a lighting element 3298 which may be an LED, on its side as shown. In one example, the probe has a diameter of 7.5 mm. Lighting may be powered by a wire running out of the portal or a wireless transmission coil may be incorporated into structure 3200 for use of a remote power source. The tip includes exposure of an electrode 3293 for neuromonitoring. The structure may be made of carbon fiber and, with lighting and neuromonitoring considered, may incorporate composite materials. In alternatives, the structure may include none or only one of the lighting and neuromonitoring features. In some alternatives, additional neuromonitoring patches may be included on other parts of the structure or on squid rods of an attached squid cap. As another option, extending from tip may be a 2 mm stiff guide wire which can also function to anchor the structure.

In some embodiments, a retractor system may incorporate a neuromonitoring patch 3300, as shown in FIGS. 49A-49C. Patch 3300 is advantageous as it provides a way to conduct neuromonitoring without having specially insulated coatings on the retractor rods. This is in addition to its core function of providing for electrical conductivity while also having an insulation layer contacting skin of the patient. Neuromonitoring matching includes a strong woven cloth layer 3302, conductive pro-stimulation layer 3304, and a conductive carbon film 3306. Incorporated with a retractor used to create a surgical portal, neuromonitoring match 3300 is wrapped around a retractor rod 3310 as shown in FIG. 49B, where the strong woven cloth 3302 forms an inner layer facing the rod surface. Effectively, the patch forms a sleeve type structure. A wire connection 3308 to facilitate the neuromonitoring is included. Toward an insertion end 3309 of the patch conductive pro-stimulation layer 3304 is exposed. On an outside of conductive carbon film 3306 is an insulation layer to control the direction of stimulation for neuromonitoring. Another advantage of the neuromonitoring patch is that it may be replaced while keeping the same rod for additional use.

Figure 50:
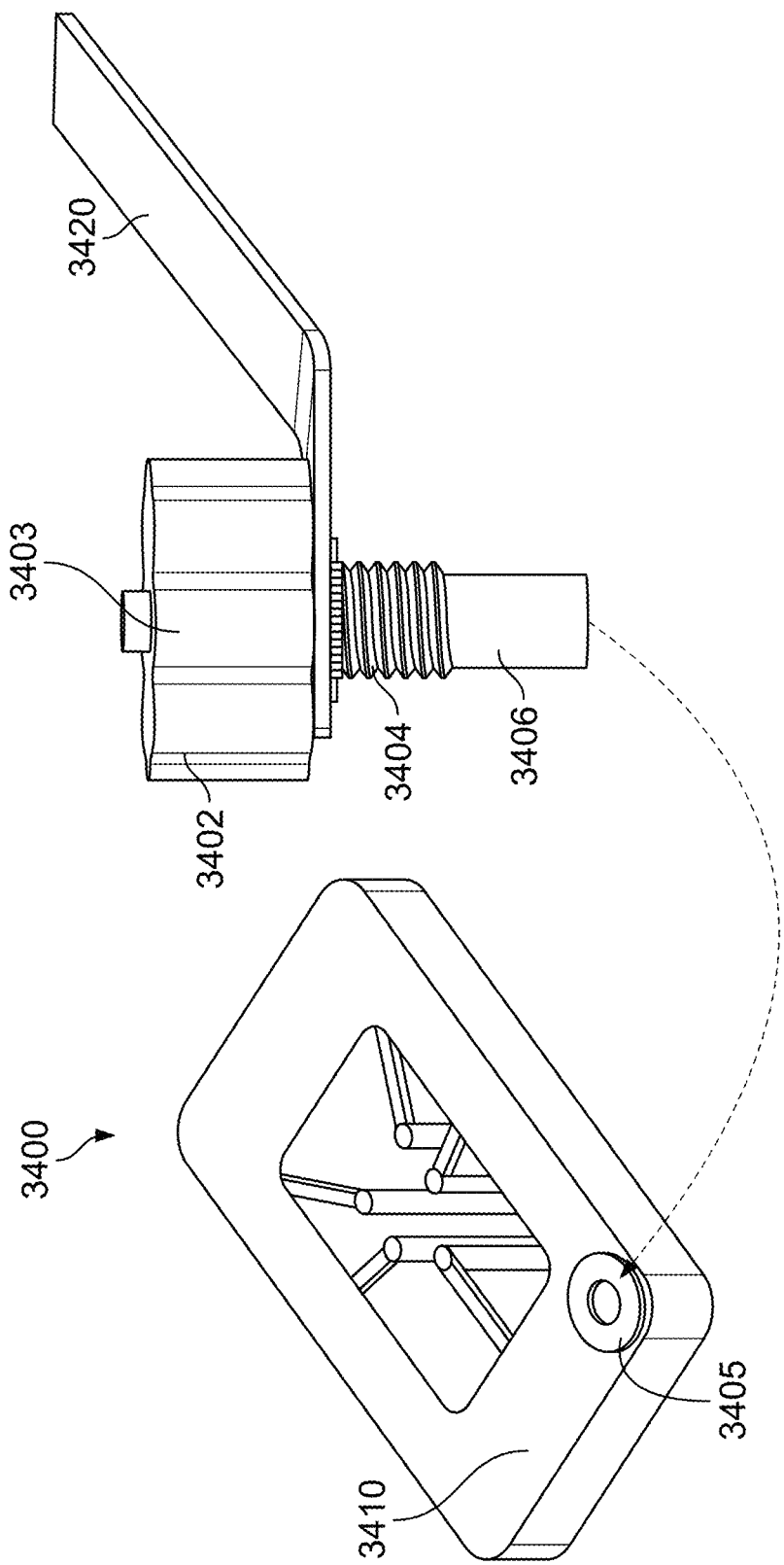
FIG. 50 is a side view of a quick connector according to one embodiment of the disclosure.

In yet another embodiment, a retractor system may be complemented by a quick connector 3400 for provisional engagement to a rigid arm as shown in FIG. 50. Quick connector includes a knob 3402, ball plunger release 3403, and a stem with a threaded portion 3404 and a provisional lock section 3406. A connection 3420 to a rigid arm or table extends from the stem as shown. Quick connector 3400 is advantageous in that it provides a simpler means of attaching the retractor to a rigid arm while also being adapted so that while engaged, the retractor may be aligned.

Another aspect of the present disclosure relates to a kit including one or more items, such as a set of retractor rods and a squid cap. In one embodiment, a kit includes five retractor rods and a squid cap. In variants, the kit may include five rods and a squid core combination structure, a central core element, or a squid cap with probe. In other embodiments, a kit may include ten rods, fifteen rods, or any other number of rods along with one or more of a squid cap, squid core combination structure, central core element or squid cap with probe. In further embodiments, any combination of retractor rods and the above described elements may be further complemented by a retractor handle. Similarly, such combinations may further include a retractor frame or both a retractor handle and a retractor frame.

In any one of the above embodiments, the kit or individual items and combinations thereof may be disposed within a packaging or a plurality of packages. For example, all of the items of the kit may be disposed within a single packaging. In another example, all of the rods may be in one packaging while all of the squid caps, central core elements and/or probes in another. It is contemplated that the elements of a given kit may be sorted into any subgroups desired, where each subgroup may be packaged separately. Of course, each item of a kit may also be individually packaged. For example, each rod and squid cap in a kit may be packaged separately. Through packaging each item in the kit separately or in separate combinations, sterility may be controlled for each item within the kit.

In another aspect, the present disclosure relates to a method of creating a surgical portal for accessing a surgical site in a patient. Although the embodiments herein are described with reference to a lateral trans-psoas approach to the spine, it is contemplated that such methods can be modified for other approaches to the spine or indeed surgery directed to other areas of the human anatomy, such as those described above.

Figure 21:
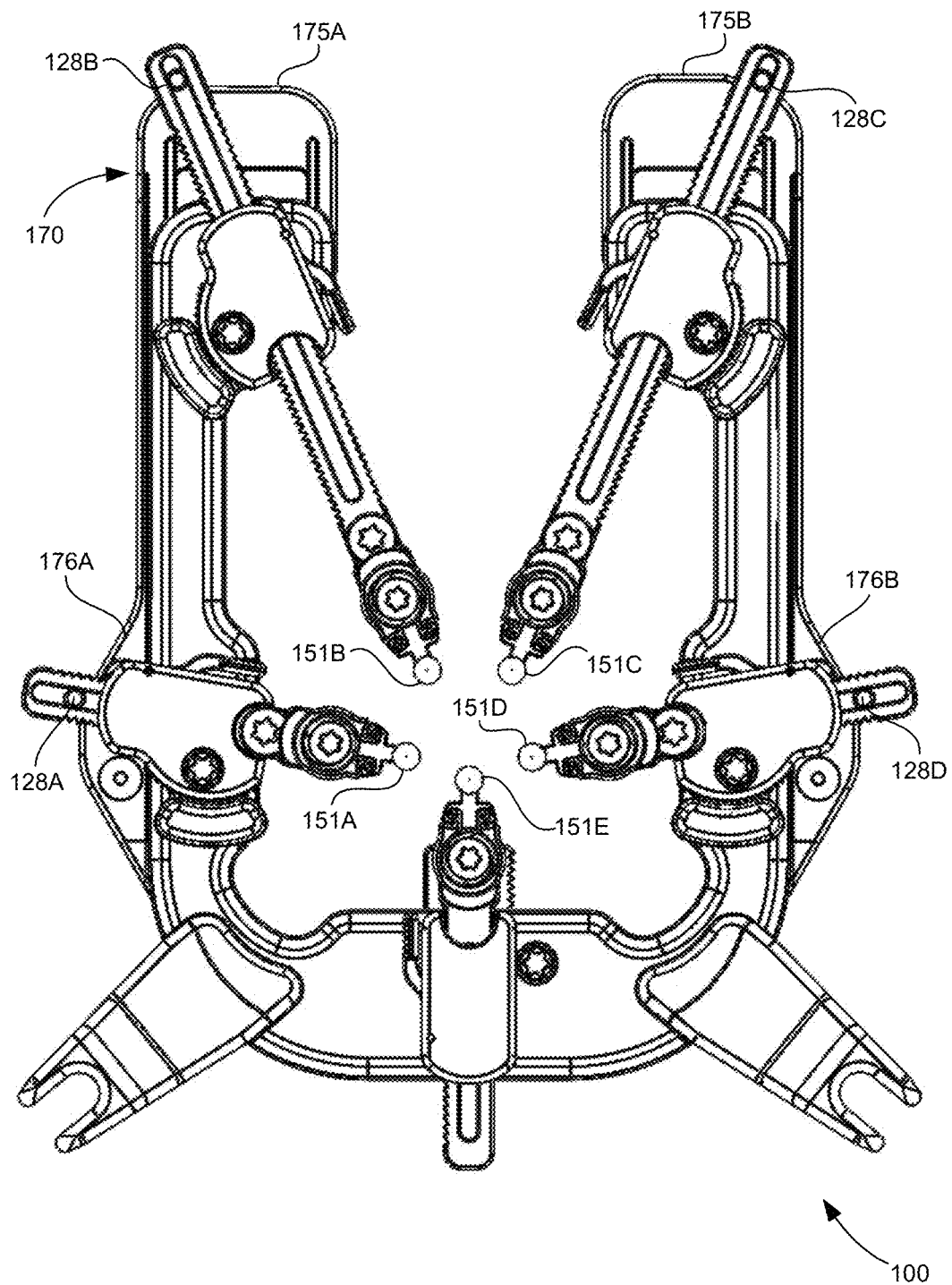
Figure 22:
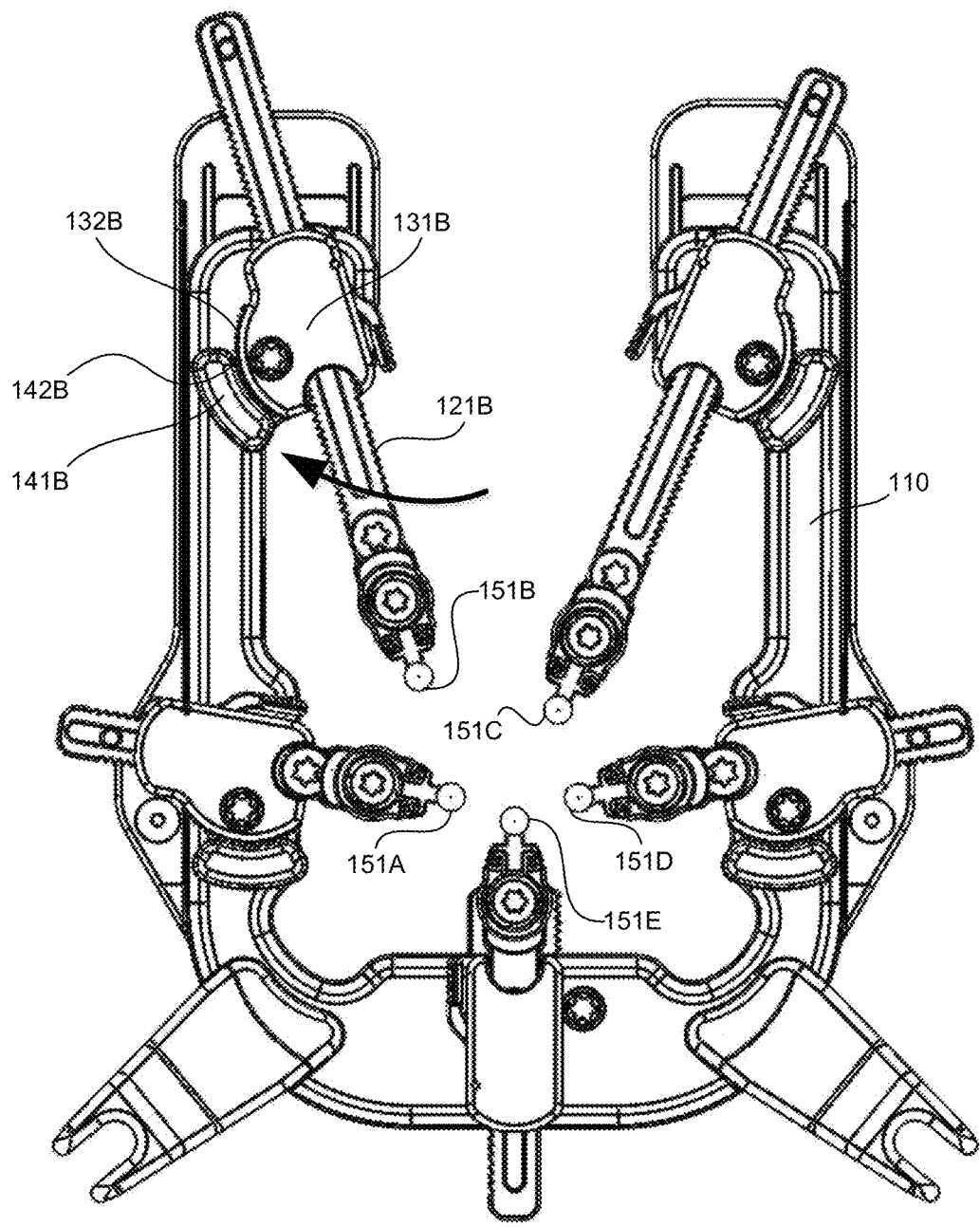

In one embodiment, a retractor 100 is used to open up a surgical portal through a sequence as shown in FIGS. 20-22. Initially, rods 151A-E of retractor 100 are in a closed position in contact with one another, and squid cap 280 (shown in phantom) is slid onto a top side of rods adjacent to the arms of the retractor as shown in FIG. 20. Engagement occurs between arm engagement portions 153A-E of the rods and slots 289A-E of the squid cap, respectively. This form of engagement is also contemplated as being compatible with other types of rods and may involve modification of the slots 289A-E on squid cap 280 for engagement with a surface on the rods. While squid cap 280 is positioned over rods 151A-E, the rods are held in position with respect to each other and in contact with each other so that the rods as a group are centered on a central cannulation or squid central core 290, as shown in FIG. 6, for example. In this arrangement, a circle around an outer envelope of the five closed rods in contact with one another has a diameter of 10.9 mm when the rods are 4 mm in diameter. With a guidewire (not shown) in place in a body of a patient and docked at a target site, the guidewire having been placed through a cannulated initial probe, for example, the retractor is brought into position to be placed over the guidewire and into the patient. For a lateral trans-psoas procedure, one rod is positioned oriented on a posterior side, two rods are anterior, and two are cranial-caudal for insertion.

Where squid cap 280 includes squid central core 290, retractor 100 is centered on a cannulation in squid central core 290 to place the core over the guidewire, thereby centering the retractor over the guidewire. The cannulation in the central core is sufficient to fit over the guidewire, which in some examples varies from 1 mm to 4 mm in diameter. Maintaining a position of squid cap 280 over and around rods 151A-E as shown in FIG. 20, the rods are advanced into the patient. During insertion, squid cap 280 holds the rods in place to control a size of the initial tissue expansion. Once a desired depth is reached, such as immediately adjacent to the spine in a lateral trans-psoas approach, the retractor frame is locked into position using the attached rigid arm. A rigid arm support may be as disclosed in U.S. Prov. Pat. App. No. 62/546,780. During advancement of the rods, or after full advancement, squid cap 280 is removed from its engagement with the retractor rods in preparation for retraction to create a surgical portal.

To create an initial surgical portal to access a surgical site, slide tool 170 secured directly beneath frame 110 is used. The surgical portal is formed through a rapid actuation action by pulling slide tool 170 from the frame 110, as shown in FIG. 21. As an alternative to pulling by hand, a tool, such as a torx tool, may be used to pull the slide tool from the frame. Each arm 151A-E includes an opening at an end remote from the rod with a rapid opening pin 128A-E disposed therein, the pin oriented perpendicular to a length of the arm. As the slide tool 170 is pulled, it catches pins in the arms that are in the path of the slide tool, and causes the arms to be retracted as the pins move with the moving edge of slide tool 170. This is illustrated in FIG. 21, where pins 128B and 128C catch onto end ramps 175A and 175B, respectively, and pins 128A and 128D catch onto lateral ramps 176A and 176B, respectively. As slide tool 170 moves further from frame 110, arms 121B, 121C move in the same direction, causing rods 151B, 151C to move away from posterior rod 151E. Similarly, arms 121A and 121D are pulled away from posterior rod 151E. In a lateral trans-psoas approach, rod 151E is located on a posterior side of the patient and operates as a fixed rod. Thus, four of the five rods actuate while one remains fixed as rapid opening is performed using slide tool 170. The retraction procedure is arranged so that expansion occurs in an anterior direction to prevent any impingement of nerves located posterior to posterior rod 151E. This is particularly critical in a lateral trans-psoas procedure since the area in the spinal region posterior to the posterior rod location has a significant presence of nerves.

A shape of a surgical portal created through rapid opening using slide tool is controlled by the orientation of the retractor arms, the ramp slope (rate) on the slide tool and the geometry of the slide tool generally, and the spacing of predetermined increments for adjustment of the arms relative to the frame. Adjustment of the ramps, using mechanisms such as those shown in FIG. 19B, provides a means to change the geometry of the opening created through rapid opening. Further, a length of central extension 173 on slide tool 170 may be modified in size to dictate a maximum translation of slide tool as a longer central extension 173 will contact a keel of rod 151E upon translation of the overall slide tool 170.

A size of a surgical portal opening created through the rapid opening using slide tool may be user specified. For example, if an implant intended to be implanted into the patient is 12 mm×22 mm in dimensions, a surgical portal 14 mm×24 mm may be created through rapid opening. Similarly, ramp angles of the slide tool may be customized to create a desired opening shape so that clearance around the implant in the surgical portal after rapid opening is limited to 1 mm (e.g., an opening 10 mm×20 mm for an implant of 8 mm×18 mm). In an example where the retractor frame measures 166 mm×112 mm, the rods can be retracted to create an opening measuring 20 mm×30 mm in dimensions. In examples where the posterior rod, i.e., rod at the base of the U-shaped frame, is adjustable, such rod may be adjusted up to 20 mm to increase or decrease the surgical portal size.

Once the rapid opening procedure using slide tool 170 has created an initial portal, the portal shape and/or size may be tailored through individual adjustment of one or more rods. This may be advantageous, for example, to create a larger surgical portal than that possible with rapid opening, or to tailor the shape of the surgical portal, among many other purposes. In FIG. 22, rod 151B, via arm 121B, is swung toward frame 110 and pulled away from posterior rod 151E through rotating support 131B to create a larger, irregular opening. Swinging occurs in predetermined increments, as teeth 132B on rotating support 131B are moved relative to teeth 142B on fixed support 141B. Arm 121B swings about an axis of rotation fixed on rotating support 131B, as is apparent in FIG. 22. Arms may swing up to thirty degrees to customize the working portal and move tissue out of the surgical portal.

Figure 23:
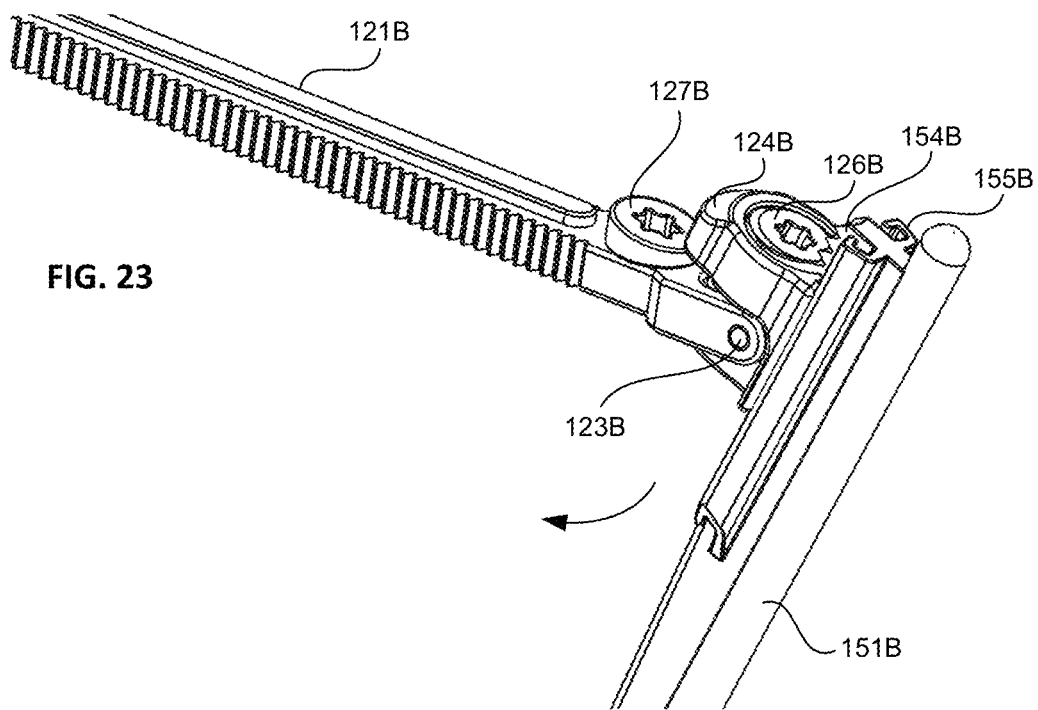
FIG. 23 is a perspective view of the arm and attached rod shown in FIG. 3 where the rod is toed out.
Figure 24:
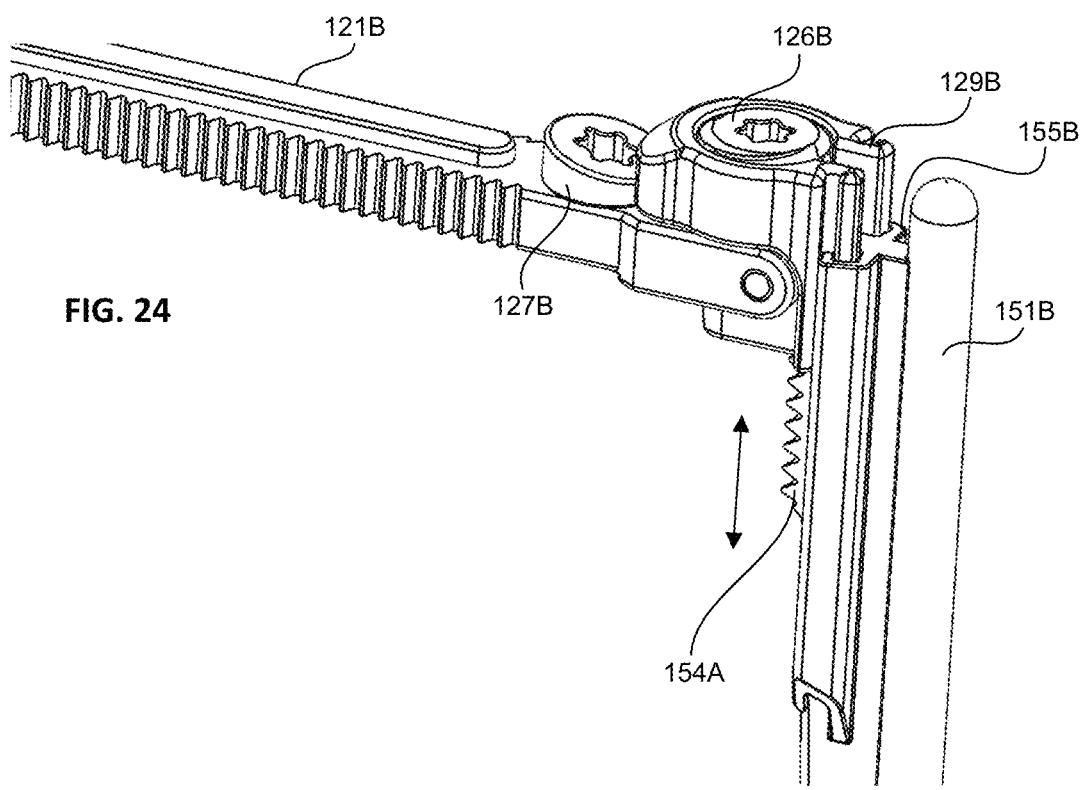
FIG. 24 is a perspective view of the arm and attached rod shown in FIG. 3 where the rod is advanced on its axis relative to the arm.

Additionally or alternatively, rod 151B may be toed out or in by pivoting the rod relative to arm 121B about pin 123B, as shown in FIG. 23, causing the surgical portal to flare outward toward the surgical site. As depicted, toeing is accomplished through rotation of toeing cam 127B. As toeing cam 127B is rotated, pivoting component 124B is caused to rotate upward or rotate downward depending on the direction of rotation of the cam. In FIG. 23, rotation of toeing cam 127B causes pivoting component 124B to rotate upward on its arm facing side so that rod toes outward. A 180 degree rotation of toeing cam 127B causes rod to toe 10 degrees about pin 123B. In a variant, a jack-screw may be used in place of a toeing cam to achieve the same function, where a jack-screw provides for toeing out of the rod up to 20 degrees relative to a rod orientation perpendicular to the arm. Thus, using one of the toeing cam or jack-screw, the rod may be toed up to twenty degrees outward, i.e., in an external direction, or up to two degrees inward, i.e., in an internal direction. Nonetheless, it is contemplated that other structures capable of similar function may also be used as an input to cause toeing in the rod. Certain locations in the body may require a larger surface at the target site, for example, accessing the L4-L5 disc space, and toeing out may be a technique for providing the requisite surface area. Internal toeing is advantageous for, among other reasons, its structure to reduce tissue resistance when the rods are inserted.

Also additionally or alternatively, a rod position relative to a bottom end of the surgical portal, i.e., relative to the arm, may be adjusted by sliding rod 151B relative to groove 129B on pivoting component 124B of arm 121B, as shown in FIG.

24. Rod 151B may be adjusted in predetermined increments based on a spacing of teeth 154B as they engage with threads of threaded insert 126B. In particular, threaded insert 126B is rotatable about its axis to cause rod 151B to translate relative to the arm via incremental engagement with consecutive teeth 154A on the rod. As depicted, rods may be adjusted at least up to 5 mm either into or out of the surgical portal and relative to a connected arm, providing an overall range of movement up to 10 mm. Adjustment of a rod position along a direction of its length is advantageous in that it may be used to restrict tissue creep if the rod is lowered further into the surgical portal, addressing a particular concern during lateral trans-psoas procedures. Such telescoping adjustments may also be used to avoid sensitive anatomy otherwise encountered by the rod during advancement or to provide an additional way to improve docking to an intervertebral disc.

It should be noted that although linear movement of retractor arms through actuation of slide tool is one way the arms may be linearly adjusted within the retractor frame, such movement may also be achieved with movement of individual rods. For example, arm 121B can be retracted or advanced along its longitudinal axis by ratcheting the arm within rotating support 131B. Teeth (not shown) inside rotating support 131B engage with teeth 122B on arm to move it in predetermined increments. Such arm adjustment may be at 1.4 mm increments between the teeth, for example.

Although the individual rod adjustment described above is specifically directed to arm 121B and rod 151B, such adjustments may also be performed with rods 151A and 151B-E. Further, for any given retractor, such individual rod adjustment is not limited to a single rod overall or to any given step in the surgical portal creation procedure. Any number of rods may be manipulated to reach a customized rod position relative to the retractor frame. For example, rods 151A and 151C may both be toed out. In another example, rod 151B is shifted downward on its longitudinal axis, while 151C is toed out and 151A is toed out and swung laterally. Any desired combination of adjustments may be employed among the rods of the retractor. As noted previously, the above description illustrates that five rods on the retractor provides great versatility with respect to surgical portal shapes particularly when compared to three or four blade retractors. Moreover, the retractor rods may be positioned to occupy a smaller footprint at the leading end of the surgical portal, thereby minimizing unnecessary intrusion into additional space within the body of the patient.

Another advantage of creating a surgical portal using retractor 100 is that the operation of the arms may be customized to move in two-dimensional space to achieve what is known as coning correction, correct cylinder, cylindrical portal or auto-toeing, allowing for the correction of detrimental toeing-in. This is an advantageous approach as the retractor rods holding tissue will have a tendency to toe-in at their insertion or distal ends due to tissue pressure, causing the surgical portal to decrease in size. Another reason for the application of this approach is to compensate for tolerance in the respective parts of the retractor, for example, natural movement of the arm relative to the frame within a 1 mm range in its at rest position. Two-dimensional movement of the arms is used to optimize rod positioning so that tissue loading on the rods is minimized. Examples of structural adjustments to compensate for toe-in tendency and/or tolerances include inclusion of arms having a length with a 500 to 1000 mm radius to compensate for a one to two degree angulation in the rod. With an arm having such a shape, movement of the arm may be in two dimensions. In another example, rods may be outwardly biased in an initial closed position, and may be secured in grooves of a central core where the grooves are deep enough to wrap around the rods (tight fit grooves). This allows the biased rods to be inserted into a patient in a parallel fashion surrounding and secured to the central core so that when the core is removed, the rod bias causes the rods to toe out automatically, offsetting at least some of the natural toeing in of the rods due to load from adjacent tissue.

Further advantages of this method include the significant flexibility in directing instruments into the surgical portal. On the open end of the U-shaped frame, for example, no barrier exists to directing an instrument at a shallow angle or from well beyond the portal into a desired location within the portal, as a space is available between the rods having a relatively small diameter or width. Similarly, because rods with a very small footprint are used to create the surgical portal, the spaces in between each rod provide a similar advantage for direction and advancement of an instrument. Indeed, the contemplated retractors include rods that generally only consume about 20% of a cross sectional area of the surgical portal created. These techniques for instrument placement may create what is sometimes called a tissue tent. As visible in FIG. 3, for example, access to the portal from areas outside it is also rendered easier due to the small amount of space taken up by the rods above the level of the retractor arm.

In another embodiment, a method of using a retractor to create a surgical portal includes use of squid cap 480 and probe 490, as shown in FIGS. 12-14. Unless otherwise stated, the method of use is the same as that described above with squid cap 280. Initially, probe 490 is inserted into the patient and directed to the target site. Once advancement of probe 490 is sufficient, a guidewire is inserted through cannulation 498 in probe 490. At this point in the procedure, squid cap 480 is inserted over rods 451A-E so as to engage and hold the rods in position within the squid cap. Squid cap 480 is then centered over probe and advanced over the probe through central opening 489, as shown in FIGS. 12 and 13. This allows squid cap 480 combined with rods 451A-E to be advanced to a target site for surgery within the patient while remaining centered on the guide wire. Alternatively, prior to advancing squid cap 480 and rods 451A-E into the patient, probe 490 may be removed, leaving only the guidewire (not shown) in place docked at the target site. Once the rods are at the desired depth within the patient, or at any time after initial placement of rods into the patient, squid cap 480 may be withdrawn from the rods. From this point, further steps may be performed to increase the size or otherwise change the shape of the portal using the slide tool or through individual actuation of one or more of the retractor arms, as described above.

In another embodiment, rods 351A-E are initially in position surrounding central core element 380 prior to advancement into the patient, as shown in FIG. 9. To position central core in this manner, handle 381 is held and core 380 is pushed through a space between the initially closed rods of the retractor. An envelope including central core element 380 and rods 351A-E is compact as the rods slide into grooves 382A-E on central core, as shown in FIG. 9, for example. Once central core 380 is in place between the rods, each rod 351A-E nests into a respective groove 382A-E so that a space in between the rods is approximately equal to a footprint of the central core. The retractor is then positioned over a previously docked guidewire and, centered on cannula 388 of central core element 380, retractor is advanced into the patient over the guidewire. Put another way, cannula 388 of central core 380 is placed and advanced over the guidewire. As the retractor rods are advanced, central core element 380 holds the rods in place. Once the retractor and rods are in a desired position in the body of the patient, the retractor is locked with a rigid arm or other stabilization device and handle 381 is pulled from between the rods to remove central core element 380 from the patient. This leaves a small surgical portal in the space previously occupied by the central core. From this point, further steps may be performed to increase the size or otherwise change the shape of the portal using the slide tool or through individual actuation of one or more of the retractor arms, as described above.

Where central core 380 includes loose-shaped grooves, such as those shown in FIG. 11, central core may also be left in place when rods are retracted. However, if central core 380 includes tight grooves that wrap around a majority of each rod circumference while central core is disposed between the rods (similar to what is shown for squid central core in FIG. 18B), rods are in a "snap fit" type of connection, and may be more difficult to laterally retract from the central core without first removing the central core from the surgical portal. In some variants of the retraction procedure using central core 380, the retractor may be rotated when handle is in place between the rods. Because the rods are nested in the central core, turning of the handle causes the core to rotate, which in turn rotates the rods as they are held by the core. This allows the retractor to rotate based on rotation of the handle.

In yet another embodiment, squid core combination structure 500 is used in a method of creating a surgical portal. As an initial step, a guidewire is docked at the target site of the surgery using a technique as preferred by the user. For example, employing techniques as described elsewhere in the disclosure. Then, squid core combination structure 500 is advanced over the guidewire via opening 588 (structure shown in FIG. 16). In some examples, the combined structure has an 11 mm outer diameter, even with squid rods 598A-E nested in central core 580 grooves 582A-E. When advancement is complete, squid enclosure 590 is removed from central core 580 by pulling on unifying cap 595, leaving only central core 580 in place within the patient, as squid rods 598A-E are connected to unifying cap 595 and thus are removed with unifying cap 595. In a variant, initial steps in the method may be performed by first inserting central core 580, then inserting squid rods 598A-E over the core prior to once again removing squid rods. A retractor with rods attached is then introduced to the surgical site by advancing the rods over central core 580 so that the rods (e.g., 551A-E) nest within respective grooves 582A-E of central core 580. As the rods are advanced, the volume of tissue displaced within the patient increases because the rods occupy space outside of the central core envelope, as shown in FIG. 18A, for example. At this step, an envelope of the central core plus rods ranges from 11.5 mm-13 mm in diameter, when measured based on the cylindrical portion of the rods. Thus, these steps involving an initial insertion with squid rods followed by replacement with retractor rods provides a means for gradually increasing a size of the surgical portal. Additionally, central core 580 holds the rods in place while they are advanced into the patient.

When the rods are advanced a desired amount, the retractor frame is locked or otherwise docked using a rigid arm or other supporting structure. Central core 580 is then removed revealing an initial surgical portal with a view to the target site at an end remote from the retractor frame. Thus, where the target site is the spine, vertebrae and/or an intervertebral disc are visible at this juncture. This visualization is advantageous in that it provides additional information to the user regarding actual conditions at the site which, in turn, may provide guidance on specific approaches to use for further retraction. From this point, further steps may be performed to increase the size or otherwise change the shape of the portal using the slide tool or through individual actuation of one or more of the retractor arms, as described above. Alternatively, the central core may be left in place in the portal during initial retraction of the rods, if desired.

Figure 37A:
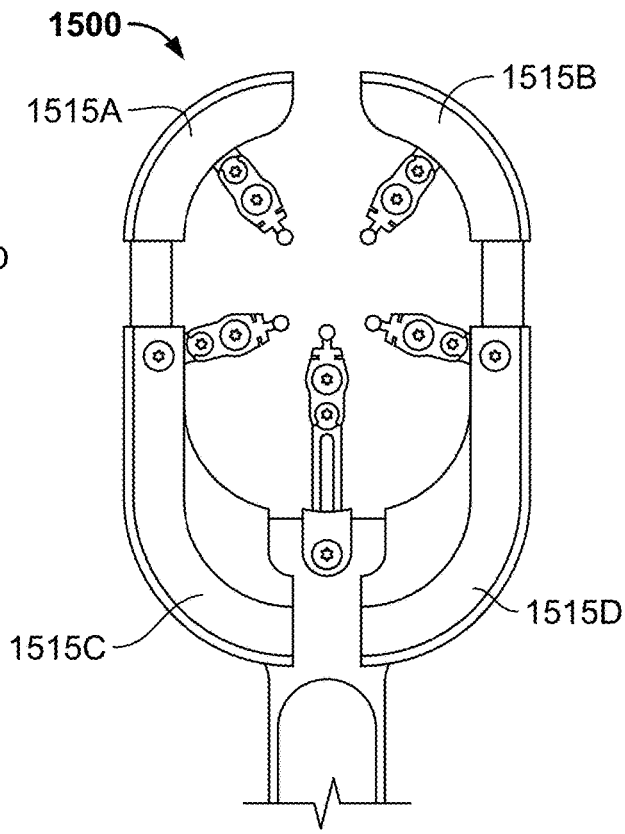
FIGS. 37A-37B are different views of the retractor of FIGS. 36A-36B in an open position.
Figure 37B:
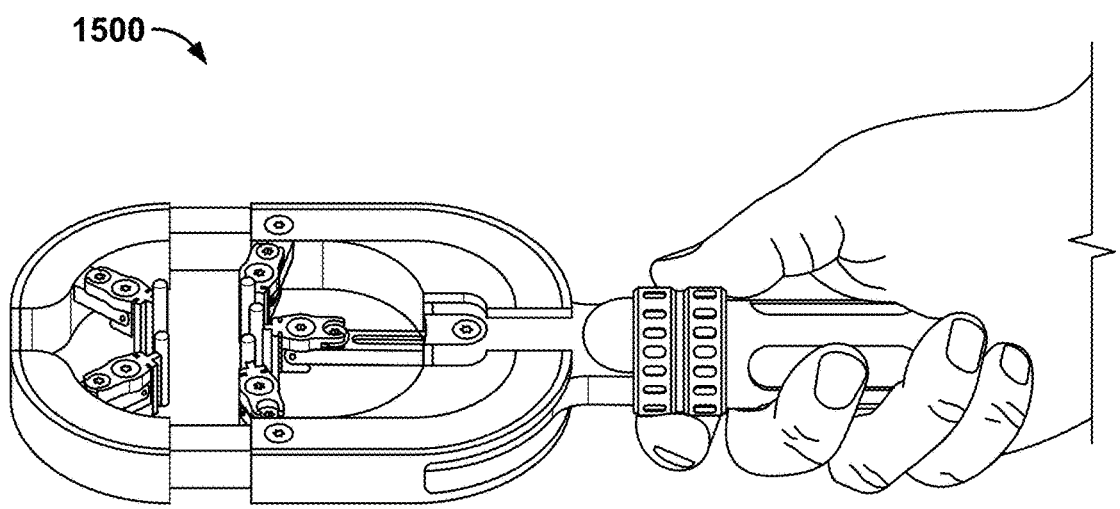

In some embodiments, a handle may be secured to the retractor and used to control opening of the rods. Thus, rods may be opened in an anterior-posterior direction first, a cranial-caudal direction first, or both simultaneously, using dials, triggers, and other controlling mechanisms as described for the various handles contemplated herein, such as those shown in FIGS. 25-35, 36A, 36B, 37A, 37B, 38-44, and 47A-B. Handle is secured to the retractor frame in a manner so as to achieve a mechanical connection between the actuating mechanisms, e.g., dial, trigger, etc., and the frame or arms holding the rods. In some of these embodiments, such as those shown in FIGS. 31-35, the handle of the retractor (e.g., handle 1480) is interconnected with a slide tool 1370 or 1470 so that rotation of the handle causes slide tool to translate relative to the frame of the retractor to provide rapid opening of the retractor rods. For example, a closed position of retractors is shown in FIGS. 31 and 33, respectively, while an open position after rapid opening is shown in FIGS. 32 and 34, respectively. FIG. 35 depicts another view of the open retractor shown in FIG. 34. In FIGS. 36A-37B, another retractor 1500 is shown in closed and open positions. A connection between handle 1570 and arms 1521A-E is built into the retractor through mechanisms such as rack and pinion for cephalad-caudal movement and a worm drive gear for anterior-posterior movement. This allows rotation of each handle component 1572, 1574 to convert into an output in the form of rod retraction as shown in FIGS. 37A-37B. Similar elements and functionality are present in the retractors shown in FIGS. 38-40. In the retractor of FIGS. 38-39, frame extension arms 1612A, 1612B include markers denoting distance so that an amount of retraction may be monitored during use.

In any one of the above embodiments, the retractor, when in position in the tissue of the patient and centered over the central core, probe or other space between the rods through which the guidewire runs, may be removed and then reinserted again over the guidewire, but centered on one of the rods of the retractor having a cannulation sized to accommodate the guidewire. When reinserted, a center of the retractor is offset from the guidewire by a distance between the rod now inserted over the guidewire and the center of the retractor. An advantage of employing this technique is that it provides controlled repositioning of the retractor while maintaining the initial guidewire placement. To obtain a similar type of offset effect, albeit to a lesser magnitude, the central core or probe may incorporate a cannulation of a size sufficient so that the retractor may shift laterally while the guidewire remains comfortably within the bounds of the cannulation.

In another embodiment, a combination central core and probe structure 3200 as shown in FIG. 48 may be used as part of a surgical procedure involving retraction of tissue using a retractor as contemplated in this disclosure. As an initial step, structure 3200 may be inserted to create an initial opening. Added safety is provided through the neuromonitoring electrode 3293 provided on the tip and the gradual taper reduces the potential for damaging tissue upon insertion. Upon full advancement, an opening the size of central core 3280 is formed over most of the surgical depth, advancing the surgical procedure over what would otherwise be multiple steps with a single step.

In any of the above embodiments, a surgical portal can be created without the use of a central core, probe or squid cap and may rely solely on the retractor rods being inserted in a closed position and then being retracted as desired once the retractor is locked in place. In other variants of the method, a surgical portal can be created solely through manual actuation of retractor arms, without the use of the slide tool. The method may also further include the insertion of bridges or shims to retain tissue and to provide lighting into the surgical portal once it has been opened. Bridges or shims may include built in lighting, such as an LED(s). Bridges and shims may include at least one groove so that they are slidable over the rod to be advanced into and held within the surgical portal. Power for the lighting may be built into the shim or bridge or may be wired in from an external source. Bridges and shims may be as disclosed in U.S. Prov. Pat. App. No. 62/546,796, the disclosure of which is hereby incorporated by reference herein in its entirety. Rings may also be advanced between the rods to provide tissue retention and lighting and may be structured as described in WO2018/039228.

The methods of retraction described above are generally made with reference to a lateral trans-psoas approach. As noted initially, the retractors contemplated herein may be used in many surgical contexts. In some instances, certain features of the retractor or other associated components may be altered or vary to suit other surgical procedures either in the spine or elsewhere in the body. For example, in an anterior to psoas approach to the spine, a fixed rod on a five rod retractor will be anterior, not posterior. Due to interference with different organs, rod length may be different in such an approach. In another example, where an L5-lumbar procedure is performed, less space may be available. In such instances, shorter rods or perhaps even smaller diameter rods may be used. Other examples of specific alterations to a procedure that may be made include varying a rod tip location when fully advanced to a surgical target site, swapping one or more rods on a retractor to suit an intended approach, using particular rods, probes, central cores, bridges, rings or shims to optimize with a working area at a maximum depth of the surgical portal near a target site, and using a variable slide tool to alter the ramps to change the type and size of surgical portal opening created through the rapid opening feature. In other examples, all rods may retract rather than keeping a single rod fixed. Similarly, two or more rods may remain fixed during retraction.

In any of the above methods, as briefly mentioned above, rods on a retractor may be substituted with rods having different features. Substitution may be performed simply by sliding out a rod from an attached arm through withdrawal of the rod along its longitudinal axis. Examples highlighting when such substitution may be desirable include replacing a solid rod with one having a cannulation sized for guidewire placement or replacing a rod with one adapted for lighting the surgical portal. Rods adapted for lighting may be rods with an internal bore for running fiber optic cables therethrough or may be rods with an LED attached, among others. Other substitutions may involve replacing a dome-tipped rod such as that shown in FIG. 2 with a pointed tip rod to function as an anchor rod. This type of rod may be particularly advantageous where the opening benefits from having a fixed rod among a plurality of rods.

In any of the above embodiments, the method of retraction may incorporate neuromonitoring, as previously described. For example, when an electrode is affixed to a probe, the probe may be inserted and rotated during insertion to evaluate the presence of nerves in the path to be expanded into a surgical portal in multiple directions. The probe may also include multiple probes, if desired. Similarly, the method may be performed using electrodes on one or more rods of the retractor or both the probe and the rods. In still other examples, neuromonitoring technology may be included in any element inserted into the portal, such as bridges or shims. In some embodiments, neuromonitoring patch 3300 (FIGS. 49A-49C) may be used to conduct neuromonitoring. Patch 3300 may be attached to a retractor rod prior to insertion of the retractor or after insertion. Any number of rods may be complemented by a patch during the procedure.

In any of the above embodiments, navigation technology as previously described may be incorporated into the procedure to improve directional control of the retractor rods and associated elements when advancing toward a target site and during retraction.

In any of the above embodiments, a retractor may be provisionally engaged with a rigid arm or table using quick connector 3400 as shown in FIG. 50. First, quick connector ball plunger 3403 is held down and placed over a threaded mount 3405 on a retractor frame 3410. Then, provisional lock section 3406 is placed through the threaded mount on the frame. This provides provisional locking of the retractor. To further tighten the lock, knob 3402 is rotated so that threads 3404 engage with corresponding threads in mount 3405.

Figure 52A:
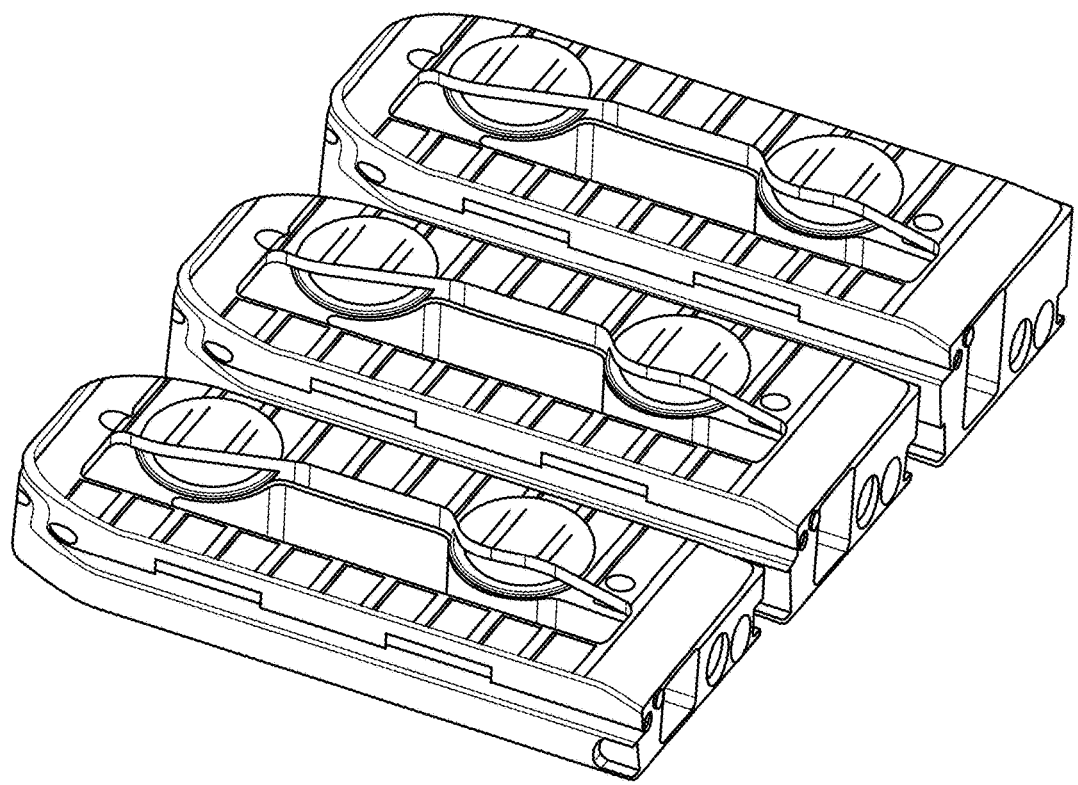
FIGS. 52A and 52B are perspective views of implants according to one embodiment of the disclosure.
Figure 52B:
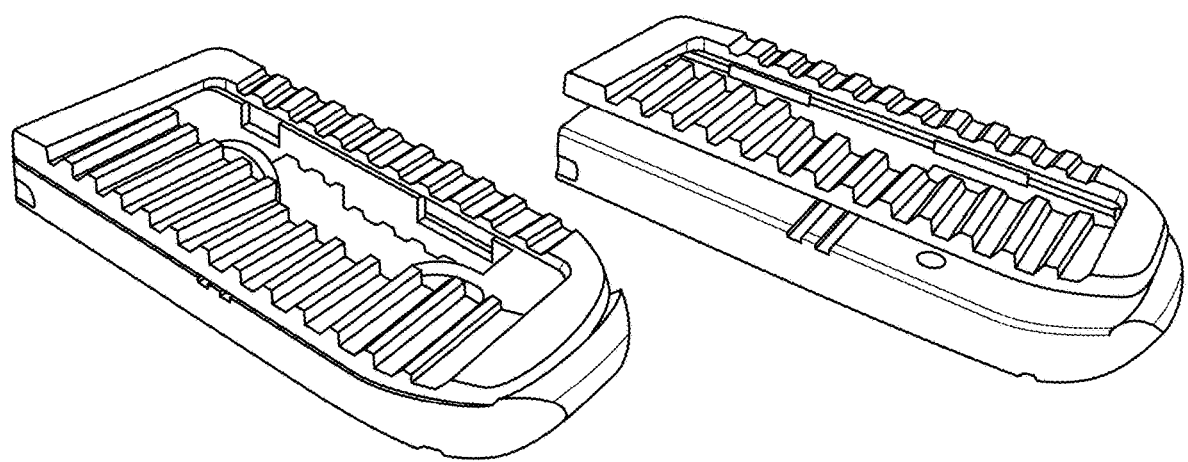
Figure 53:
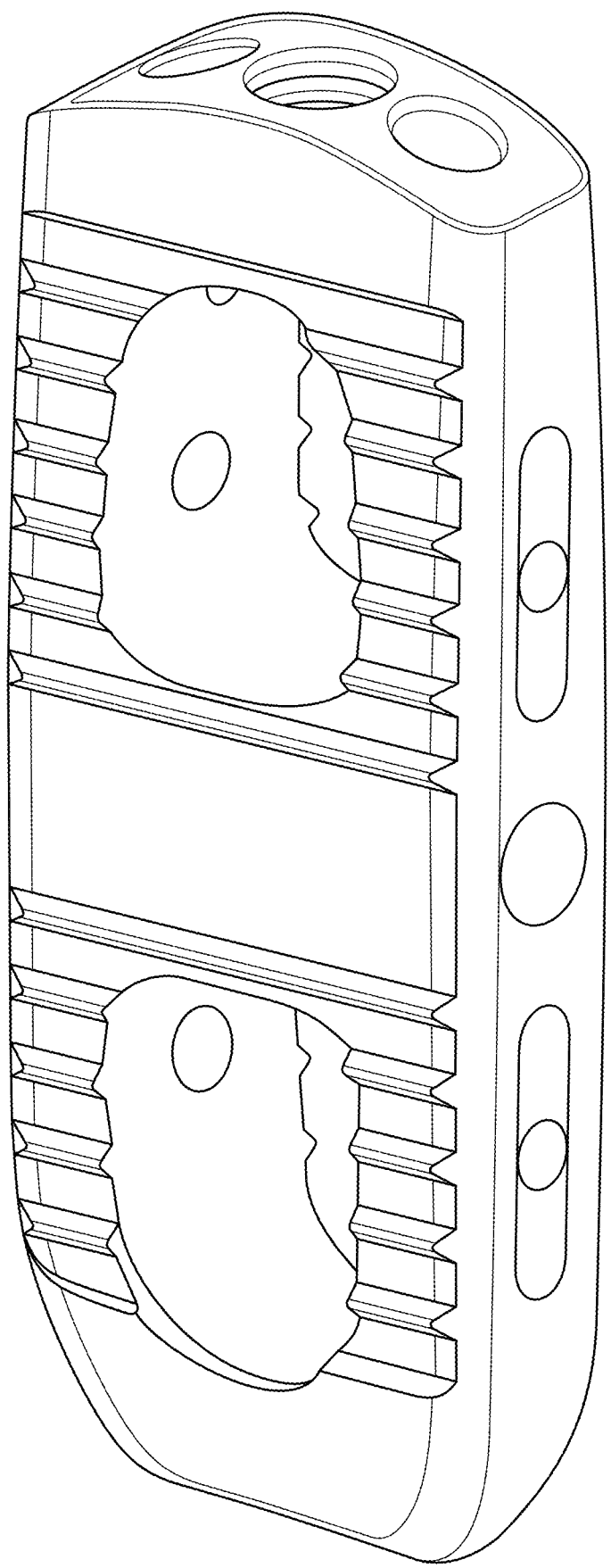
FIG. 53 is a perspective view of implants according to one embodiment of the disclosure.

The foregoing instrumentation, apparatuses, devices, systems and methodologies can be utilized to implant various spinal implants and prosthesis. For instance, it is contemplated that any of the inventions disclosed herein can be utilized in conjunction with the implants disclosed in U.S. patent application Ser. No. 14/994,749 and U.S. Provisional Application Nos. 62/103,276 and 62/560,910, the disclosures of which are hereby incorporated by reference herein. Moreover, FIGS. 52A, 52B and 53 depict further implants suitable for implantation in accordance with the present invention. FIGS. 52A-B depict an expandable implant, while FIG. 53 depicts a static implant. It is noted that all such implants exhibit combination porous and solid constructions, although it is certainly contemplated to implant entirely solid or entirely porous implants in accordance with the present invention. Of course, it is contemplated to utilize implants that vary widely with respect to any of the foregoing implants when employing instrumentation, apparatuses, devices, systems and methodologies according to the various aspects and embodiments of the present disclosure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A retractor comprising:
a frame including a central body, a first lateral extension and a second lateral extension, the first lateral extension including a first inner segment abutting the central body and a first outer segment extending from the first inner segment;
a first arm extending from the central body and a first rod attached to the first arm;
a second arm attached to the first inner segment of the first lateral extension and a third arm attached to the first outer segment of the first lateral extension, a second rod attached to the second arm and a third rod attached to the third arm;
a fourth arm and a fifth arm attached to the second lateral extension, a fourth rod attached to the fourth arm and a fifth rod attached to the fifth arm,
wherein the first rod is translatable along a first axis through a length of the first arm and the first rod is pivotable about a second axis transverse to the first axis,
wherein the first inner segment of the first lateral extension is movable relative to the central body and the first outer segment of the first lateral extension is movable relative to the first inner segment.

2. The retractor of claim 1, wherein the first inner segment and the first outer segment of the first lateral extension are moveable independently of the first rod.

3. The retractor of claim 2, wherein the second lateral extension includes a second inner segment abutting the central body and a second outer segment extending from the second inner segment, the second inner segment being configured to move simultaneously with the first inner segment.

4. The retractor of claim 3, wherein the first outer segment is configured to move simultaneously with the second outer segment.

5. The retractor of claim 1, wherein the first lateral extension and the second lateral extension are movable with respect to each other along an axis parallel to the second axis.

6. The retractor of claim 1, wherein the first outer segment of the first lateral extension is moveable relative to the first inner segment of the first lateral extension along an axis parallel to the first axis.

7. A retractor comprising:
a frame;
first, second, third, fourth, and fifth arms, each arm attached to the frame;
first, second, third, fourth, and fifth rods attached to the first, second, third, fourth, and fifth arms, respectively, each of the first, second, third, fourth, and fifth rods being telescopically adjustable along respective longitudinal axes of the rods and rotatable about respective pivot axes perpendicular to the longitudinal axes, and
a first actuation mechanism configured to control simultaneous movement of at least two rods of the second, third, fourth, and fifth rods,
wherein the first rod is independently translatable along a longitudinal axis of the first arm and the first actuation mechanism is configured to control simultaneous movement of the third and fifth rods relative to the second and fourth rods.

8. The retractor of claim 7, wherein the first actuation mechanism is not operatively connected to the first rod.

9. The retractor of claim 7, further comprising a second actuation mechanism configured to control simultaneous movement of the second, third, fourth and fifth rods.

10. The retractor of claim 9, wherein the second actuation mechanism is configured to control simultaneous movement of the second and third rods in a first direction and the fourth and fifth rods in a second direction opposite the first direction.

11. The retractor of claim 7, wherein the second arm further comprises a threaded insert disposed within the arm, the threaded insert operatively engaged to teeth on a surface of the second rod, the threaded insert being rotatable to control the telescoping adjustment of the second rod relative to the second arm.

12. The retractor of claim 7, further comprising a toeing cam disposed in at least a portion of the second arm such that the toeing cam is rotatable to control rotation of the second rod about the pivot axis through the second arm.

13. The retractor of claim 7, wherein the first, second, third, fourth and fifth rods each have a first outer surface area constituting a majority of a total outer surface area of the respective rod, the first outer surface area being a convex outer surface.

14. The retractor of claim 7, wherein the first rod includes a pointed distal tip configured for engagement with tissue.

15. The retractor of claim 7, wherein the first arm further comprises a threaded insert disposed within the first arm and a toeing cam disposed in the first arm, the threaded insert operatively engaged to teeth on a surface of the first rod to control the telescoping adjustment of the first rod and the toeing cam rotatable to control rotation of the first rod about an axis perpendicular to a longitudinal axis of the first arm, the threaded insert and the toeing cam being translatable along the longitudinal axis of the first arm.

16. A method of using a retractor comprising:
retrieving the retractor of claim 7;
positioning the retractor over a surgical site; and
changing a position of at least one of the first, second, third, fourth and fifth rods relative to the frame.

17. A retractor comprising:
a frame;
first, second third, fourth and fifth arms, each arm attached to the frame;
first, second, third, fourth and fifth rods attached to the first, second, third, fourth and fifth arms, respectively;
a first actuation mechanism configured to control simultaneous movement of the third and fifth rods relative to the second and fourth rods; and
a second actuation mechanism configured to control simultaneous movement of the second and third rods relative to the fourth and fifth rods,
wherein the first rod is independently translatable along a central longitudinal axis of the first arm and is unmoved by manipulation of either the first or second actuation mechanism.

18. The retractor of claim 17, wherein the second and third arms have respective first ends attached to a lateral extension of the frame, the second and third rods being at a first distance from the respective first ends of the second and third arms irrespective of actuation of the first or second actuation mechanism.

19. The retractor of claim 17, wherein the frame includes a central body that holds the first arm, a first lateral extension that holds the second and third arms, and a second lateral extension that holds the fourth and fifth arms, each of the first and second lateral extensions extending to a free end.

* * * * *